United States Patent
Sawada et al.

(10) Patent No.: US 6,582,351 B1
(45) Date of Patent: Jun. 24, 2003

(54) IMIDAZOPYRIDINONE DERIVATIVES AND THEIR USE AS PHOSPHODIESTERASE INHIBITORS

(75) Inventors: Kozo Sawada, Tsukuba (JP); Takayuki Inoue, Tsukuba (JP); Yuki Sawada, Ushiku (JP); Tsuyoshi Mizutani, Tsukuba (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/030,979

(22) PCT Filed: Jul. 12, 2000

(86) PCT No.: PCT/JP00/04687

§ 371 (c)(1), (2), (4) Date: Jan. 16, 2002

(87) PCT Pub. No.: WO01/05770

PCT Pub. Date: Jan. 25, 2001

(30) Foreign Application Priority Data

Jul. 21, 1999 (AU) .............................................. PQ1747
Sep. 9, 1999 (AU) .............................................. PQ2730

(51) Int. Cl.[7] ....................... A61K 31/435; C07D 47/04
(52) U.S. Cl. ....................... 596/118; 546/118
(58) Field of Search ........................... 546/118; 514/300

(56) References Cited

FOREIGN PATENT DOCUMENTS

| DE | 489 459 | 12/1929 |
|----|---------|---------|
| EP | 0 694 536 | 1/1996 |
| EP | 0 882 718 | 12/1998 |
| GB | 1 505 173 | 3/1978 |
| JP | 05 222000 | 8/1993 |

OTHER PUBLICATIONS

Database Crossfire Online! Beilstein Instutut zur Foerderung der Chemischen Wissenschaften; XP002148865, Beilstein Registry No. 648830 & ZH. Vses. Khhim. O'Va Im. Mendeleeva, vol. 13, No. 3, pp. 352–353 1968.

M. Hori et al.: "Design and syntheses of a series of novel serotonin 3 antagonists." Chemical and Pharmaceutical Bulletin, vol. 41, No. 10, pp. 1832–1841 10/93.

S. Lindstrom et al.: "Synthesis of the mutagenic 2–amino–1, 6–dimethyl–imidazo '4, 5–b!lpyridine (1,6DMIP) and five of its isomers" Heterocycles, vol. 38, No. 3, pp. 529–540 Mar. 01, 1994.

S. Grivas et al.: "Palladium(0)–catalyzed phenylation on imidao 4, 5–B!pyridines" Journal of Heterocyclic Chemistry, vol. 32, No. 2, pp. 467–471 1995.

J. Davoll et al.: "Some N–substituted 2_oxobenzimidazolines" Journal of the Chemical Society, pp. 314–318 1960.

M. Bianchi et al.: "Compounds with antiulcer and antisecretory activity. I." European Journal of Medicinal Chemistry–Chimica Therapeutica, vol. 16, No. 4, pp. 321–326 1981.

Pw Guo et al.: "Solid Phase Synthesis of Benzimidazolones" Tetrahedron Letters, vol. 39, No. 3–4 Jan. 15, 1998.

*Primary Examiner*—Bernard Dentz
(74) *Attorney, Agent, or Firm*—Oblon, Spivak, McClelland, Maier & Neustadt, P.C.

(57) ABSTRACT

A compound (Ia):

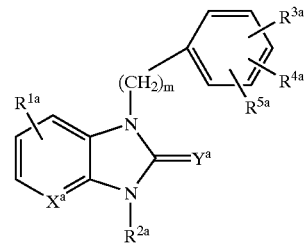

wherein the variables are defined in the specification, its prodrug or a pharmaceutically acceptable salt thereof useful in the treatment of angina, hypertension etc.

7 Claims, No Drawings

… (1) …

IMIDAZOPYRIDINONE DERIVATIVES AND THEIR USE AS PHOSPHODIESTERASE INHIBITORS

TECHNICAL FIELD

This invention relates to heterocyclic compounds having pharmacological activities, their pharmaceutical compositions and their use as a medicament for treatment or prevention of diseases mediated by cGMP-PDE.

BACKGROUND ART

It is known that a cyclic guanosine-3',5'-monophosphate (hereinafter referred to as cGMP) derived from a guanosine-5'-triphosphate possesses a relaxant activity of smooth muscle and that a cyclic guanosine-3',5'-monophosphate phosphodiesterase (hereinafter refereed to as cGMP-PDE) acts to catalyze the degradation of cGMP to a guanosine-5'-monophosphate. cGMP-PDE is a family of enzymes consists from PDE-I, II, V and so on. The compounds having an inhibitory activity of cGMP-PDE are disclosed in European Patent Publication Nos. 579,496; 534,443; 526,004; 636,626; U.S. Pat. Nos. 3,819,631; 5,294,612; 5,488,055; International Patent Publication Nos. 93/07,124; 94/19,351; 95/18,097; 96/32,379; Japan Patent Publication Nos. 05-222,000; 07-330,777; and so on.

Further, some kinds of benzimidazolone compounds having affinity for receptors of vasopressin and/or oxytocin are disclosed in Japanese Patent Kokai No. Hei 8(1996)-73439.

DISCLOSURE OF INVENTION

According to one aspect of this invention, it provides novel heterocyclic compounds represented by the below formula (Ia) and their pharmaceutical compositions.

According to another aspect of the invention, it provides a pharmaceutical composition for treatment or prevention of diseases mediated by cGMP-PDE (especially PDE-V) containing a heterocyclic compound represented by the below formula (I) as an active ingredient.

Specifically, the present invention provides a compound of the formula (Ia):

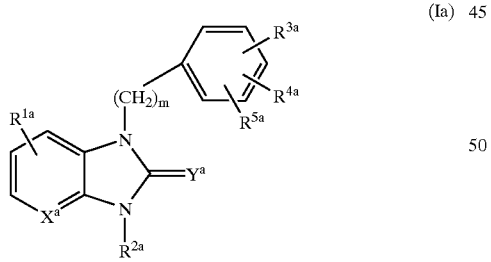

(Ia)

wherein
$X^a$ is CH or nitrogen atom;
$Y^a$ is oxygen atom or sulfur atom;
$R^{1a}$ is a halogen atom; cyano group; nitro group; carbamoyl group; a lower alkylcarbamoyl group which may be substituted with a heterocyclic group; carboxy group; a protected carboxy group; a lower alkyl group; a halo (lower)alkyl group; a lower alkoxy group; an acyl group; or a lower alkanesulfonyl group,
$R^{2a}$ is a lower alkyl group, a cycloalkyl group or a heterocyclic group, among which the lower alkyl group may have one to three substituents selected from the group consisting of hydroxy, protected hydroxy, acyl, lower-alkoxy-substituted aralkyloxy, amino, lower alkylamino, acylamino, lower alkoxycarbonylamino, lower alkanesulfonylamino, ureido, lower alkylureido, sulfamoylamino, protected carboxy, carboxy, lower alkanesulfonyl, lower alkylenedioxy, carbamoyl, lower alkyl carbamoyl and sulfamoyl; and
the cycloalkyl group and the heterocyclic group may have one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, lower alkanesulfonyl, lower alkyl, hydroxy(lower)alkyl, protected hydroxy(lower)alkyl, lower alkylenedioxy, carbamoyl and sulfamoyl,
$R^{3a}$, $R^{4a}$ and $R^{5a}$ are, the same or different, hydrogen atom, a halogen atom, a lower alkanoyl group, carboxy group, a protected carboxy group, carbamoyl group, nitro group, cyano group, a lower alkyl group optionally substituted by hydroxy, a lower alkoxy group or a lower-alkoxy-substituted aralkyl group; or two of $R^{3a}$, $R^{4a}$ and $R^{5a}$ may combine together to form a lower alkylenedioxy group,
m is an integer of 1 or 2,
provided that when $R^{3a}$ is hydrogen atom, $R^{4a}$ is a lower alkoxy group and $R^{5a}$ is hydrogen atom, a halogen atom, cyano group, a lower alkyl group, a lower alkoxy group, a protected carboxy group, carboxy group or nitro group then
1) the lower alkyl group for $R^{2a}$ has one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, carboxy, lower alkanesulfonyl, lower alkylenedioxy, carbamoyl, lower alkyl carbamoyl and sulfamoyl,
2) the cycloalkyl group for $R^{2a}$ has one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, lower alkanesulfonyl, lower alkyl, hydroxy(lower)alkyl, protected hydroxy(lower)alkyl, lower alkylenedioxy, carbamoyl and sulfamoyl,
3) the heterocyclic group for $R^{2a}$ is selected from pyrrolidinyl group, dioxanyl group and piperidyl group which groups may be substituted with protected carboxy, acyl, lower alkanesulfonyl, carbamoyl or sulfamoyl,
(4) $R^{1a}$ is carbamoyl group; a lower alkylcarbamoyl group which may be substituted with a heterocyclic group; carboxy group; a protected carboxy group; an acyl group; or a lower alkanesulfonyl group;
(5) $X^a$ is nitrogen atom;
(6) m is an integer of 2; or
(7) $Y^a$ is sulfur atom,
its prodrug or a pharmaceutically acceptable salt thereof.

According to the present invention, it also provides a pharmaceutical composition directed to treatment or prevention of diseases mediated by cGMP-PDE which comprises a compound of the formula (I):

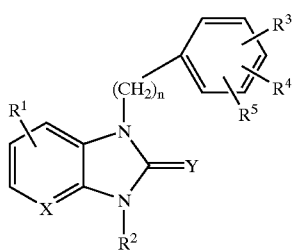

(I)

wherein

X is CH or nitrogen atom;

Y is oxygen atom or sulfur atom;

R$^1$ is a halogen atom, cyano group, nitro group, carbamoyl group, a lower alkylcarbamoyl group which may be substituted with a heterocyclic group, carboxy group, a protected carboxy group, a lower alkyl group, a halo (lower)alkyl group, a lower alkoxy group, an acyl group or a lower alkanesulfonyl group, R$^2$ is a lower alkyl group, a cycloalkyl group or a heterocyclic group, among which the lower alkyl group may have one to three substituents selected from the group consisting of hydroxy, protected hydroxy, acyl, lower-alkoxy-substituted aralkyloxy, amino, lower alkylamino, acylamino, lower alkoxycarbonylamino, lower alkanesulfonylamino, ureido, lower alkylureido, sulfamoylamino, protected carboxy, carboxy, lower alkanesulfonyl, lower alkylenedioxy, carbamoyl, lower alkyl carbamoyl and sulfamoyl; and the cycloalkyl group and the heterocyclic group may have one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, lower alkanesulfonyl, lower alkyl, hydroxy(lower)alkyl, protected hydroxy(lower)alkyl, lower alkylenedioxy, carbamoyl and sulfamoyl, R$^3$, R$^4$ and R$^5$ are, the same or different, hydrogen atom, a halogen atom, a lower alkanoyl group, carboxy group, a protected carboxy group, carbamoyl group, nitro group, cyano group, a lower alkyl group optionally substituted by hydroxy, a lower alkoxy group or a lower-alkoxy-substituted aralkyl group, or two of R$^3$, R$^4$ and R$^5$ may combine together to form a lower alkylenedioxy group, n is an integer of 1 or 2, its prodrug or a pharmaceutically acceptable salt thereof in admixture with a pharmaceutically acceptable carrier or diluent.

The present invention further provides an intermediate compound of the following formula (II) or its salt for preparing a compound (I).

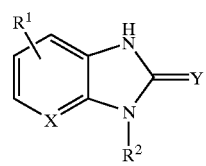

(II)

wherein

X is CH or nitrogen atom;

Y is oxygen atom or sulfur atom;

R$^1$ is a halogen atom; cyano group; nitro group; carbamoyl group; a lower alkylcarbamoyl group which may be substituted with a heterocyclic group; carboxy group; a protected carboxy group; a lower alkyl group; a halo (lower)alkyl group; a lower alkoxy group; an acyl group; or a lower alkanesulfonyl group, and R$^2$ is a lower alkyl group, a cycloalkyl group or a heterocyclic group, among which the lower alkyl group may have one to three substituents selected from the group consisting of hydroxy, protected hydroxy, acyl, lower-alkoxy-substituted aralkyloxy, amino, lower alkylamino, acylamino, lower alkoxycarbonylamino, lower alkanesulfonylamino, ureido, lower alkylureido, sulfamoylamino, protected carboxy, carboxy, lower alkanesulfonyl, lower alkylenedioxy, carbamoyl, lower alkyl carbamoyl and sulfamoyl; and the cycloalkyl group and the heterocyclic group may have one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, lower alkanesulfonyl, lower alkyl, hydroxy(lower)alkyl, protected hydroxy(lower)alkyl, lower alkylenedioxy, carbamoyl and sulfamoyl.

In the above and subsequent descriptions of the present specification, preferable examples and illustrations of the various definitions which the present invention includes within the scope are explained in detail in the following.

In this respect, it is to be noted that the following explanations are given by referring to R$^1$ to R$^5$, X and Y and that R$^{1a}$ to R$^{5a}$, X$^a$ and Y$^a$ are the same as R$^1$ to R$^5$, X and Y or included therein, respectively.

The term "lower" is intended to mean a group having 1 to 6 carbon atoms, unless otherwise indicated.

Preferably, the halogen atoms for R$^1$, R$^3$, R$^4$ and R$^5$ are fluorine, chlorine, bromine and iodine.

Preferably, the lower alkyl groups for R$^1$, R$^2$, R$^3$, R$^4$ and R$^5$ are straight or branched ones having 1 to 6 carbon atoms such as methyl, ethyl, propyl, isopropyl, butyl, isobutyl, sec-butyl, tert-butyl, pentyl, isopentyl, hexyl and the like.

Preferably, the halo(lower)alkyl group for R$^1$ is lower alkyl groups substituted with one or more halogen atoms, in which the lower alkyl moiety and the halogen atom may be the same as exemplified in the above, respectively. Preferred examples of the halo(lower)alkyl group include fluoromethyl, difluoromethyl, trifluoromethyl, chloromethyl, dichloromethyl, trichloromethyl, bromomethyl, iodomethyl, fluoroethyl, 2,2,2-trifluoroethyl, chloroethyl, 2,2,2-trichloroethyl, bromoethyl, iodoethyl, chloropropyl, bromopropyl, chlorobutyl, bromobutyl, chloropentyl, bromopentyl, chlorohexyl, bromohexyl and the like.

Preferably, the lower alkoxy groups for $R^1$, $R^3$ $R^4$ and $R^5$ are straight or branched chain ones having 1 to 6 carbon atoms such as methoxy, ethoxy, propoxy, isopropoxy, n-butoxy, isobutoxy, tert-butoxy, pentyloxy, hexyloxy and the like.

Preferably, the acyl group for $R^1$ is lower alkanoyl (e.g., formyl, acetyl, propionyl, butyryl, isobutyryl, valeryl, isovaleryl and pivaloyl), aroyl (e.g., benzoyl, toluoyl, xyloyl and naphthoyl), heterocyclic carbonyl (e.g., nicotinoyl, isonicotinoyl, thenoyl and furoyl) and the like.

Preferably, the lower alkanoyl groups for $R^3$, $R^4$ and $R^5$ are the same as those illustrated as lower alkanoyl included in the acyl group for $R^1$.

Preferably, the lower alkanesulfonyl group for $R^1$ is straight or branched one having 1 to 6 carbon atoms such as methanesulfonyl(mesyl), ethanesulfonyl, propanesulfonyl, butanesulfonyl, pentanesulfonyl, hexanesulfonyl, 2-methylpropanesulfonyl and the like.

Preferably, the protected carboxy group for $R^1$, $R^3$, $R^4$ and $R^5$ is carboxy groups protected by a conventional protecting group. Examples of the protected carboxy group include lower alkoxycarbonyl (e.g., methoxycarbonyl, ethoxycarbonyl, propoxycarbonyl, n-butoxycarbonyl, tert-butoxycarbonyl, pentyloxycarbonyl, hexyloxycarbonyl and isopropoxycarbonyl), ar(lower)alkyloxycarbonyl (e.g., benzyloxycarbonyl, trityloxycarobonyl, 4-methoxybenzyloxycarobnyl, 4-nitrobenzyloxycarbonyl, phenethyloxycarbonyl, bis(methoxyphenyl) methyloxycarbonyl, 3,4-dimethoxybenzyloxycarbonyl and benzhydryloxycarbonyl) and the like.

The lower alkyl moiety of the lower alkylcarbamoyl group for $R^1$ is the same as the lower alkyl group as illustrated in the above, and said lower alkyl moiety may be substituted with a heterocyclic group as illustrated below. Examples of the lower alkylcarbamoyl group are methylcarbamoyl, ethylcarbamoyl, propylcarbamoyl and the like. Examples of the lower alkylcarbamoyl group substituted with a heterocyclic group are furfurylcarbamoyl, thenylcarbamoyl, pyridylmethylcarbamoyl, pyrrolylmethylcarbamoyl, and the like.

Preferably, the cycloalkyl group for $R^2$ is cyclic saturated hydrocarbon residues having 3 to 8 carbon atoms such as cyclopropyl, cyclobutyl, cyclopentyl, cyclohexyl, cycloheptyl, cyclooctyl and the like.

Preferably, the heterocyclic group for $R^2$ is saturated or unsaturated, monocyclic or condensed one containing one or more hetero atoms selected from nitrogen, sulfur and oxygen atoms, such as saturated or unsaturated 3 to 7-membered heteromonocyclic group containing 1 to 4 nitrogen atoms, for example, aziridinyl, azetidinyl, pyrrolidinyl, imidazolidinyl, pirazolidinyl, piperidino, piperidyl, piperazinyl, pyrrolyl, imidazolyl, imidazolinyl, pyrazolyl, pyrazolinyl, pyridyl, pyrimidinyl, pyrazinyl, pyridazinyl, triazolyl [e.g., 4H-1,2,4-triazolyl, 1H-1,2,3-triazolyl or 2H-1,2,3-triazolyl], tetrazolyl [e.g., 1H-tetrazoly or 2H-tetrazolyl] or the like;

saturated or unsaturated 3 to 7-membered heteromonocyclic group containing 1 to 2 oxygen atoms, for example, pyranyl, furyl, dioxanyl, tetrahydropyranyl, tetrahydrofuryl or tetrahydrodioxanyl;

saturated or unsaturated 3 to 7-membered heteromonocyclic group containing 1 to 2 sulfur atoms, for example, thienyl, thiopyranyl or the like;

saturated or unsaturated 3 to 7-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl or 1,2,5-oxadiazolyl] or the like;

saturated or unsaturated 3 to 7-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl or 1,2,5-thiadiazolyl] or the like;

saturated or unsaturated 3 to 7-membered heteromonocyclic group containing 1 to 2 oxygen atoms and 1 to 3 nitrogen atoms, for example, morpholino or morpholinyl;

saturated or unsaturated 3 to 7-membered heteromonocyclic group containing 1 to 2 sulfur atoms and 1 to 3 nitrogen atoms, for example, thiazolidinyl, thiomorpholino or thiomorpholinyl;

unsaturated condensed heterocyclic group containing 1 to 3 nitrogen atoms, for example, benzopyrrolyl, benzimidazolyl, benzopyrazolyl, benzotriazolyl, quinolyl, isoquinolyl, indolyl or the like;

unsaturated condensed heterocyclic group containing 1 to 2 oxygen atoms, for example, benzofuryl or the like;

unsaturated condensed heterocyclic group containing 1 to 2 oxygen atoms and 1 to 3 nitrogen atoms, for example, benzoxazolyl, benzoxadiazolyl, phenoxazinyl or the like;

unsaturated condensed heterocyclic group containing 1 to 2 sulfur atoms, for example, benzo[b]thienyl or the like;

unsaturated condensed heterocyclic group containing 1 to 2 sulfur atoms and 1 to 3 nitrogen atoms, for example, benzothiazolyl, benzisothiazolyl, phenothiazinyl or the like.

Preferably, the aralkyl groups for $R^3$, $R^4$ and $R^5$ are lower alkyl group substituted with one or more aryl groups. Examples of the aralkyl group include benzyl, phenethyl, phenylpropyl, phenylbutyl, phenylpentyl, phenylhexyl, benzhydryl, trityl, naphthylmethyl, tolylmethyl, xylylmethyl, mesitylmethyl and the like.

Further, preferable examples of each substituents on the lower alkyl group, cycloalkyl group and heterocyclic group for $R^2$ and the aralkyl group for $R^2$, $R^3$ and $R^4$ are explained in the following.

Examples of the acyloxy group are lower alkanoyloxy (e.g., formyloxy, acetyloxy, propionyloxy and butyryloxy), aroyloxy (e.g., benzoyloxy, toluoyloxy and naphthoyloxy), heterocyclic carbonyloxy (e.g., nicotinoyloxy, isonicotinoyloxy and furoyloxy) and the like.

Examples of the acyloxy(lower)alkyl group are lower alkanoyloxy(lower)alkyl (e.g., formyloxymethyl, acetoxymethyl, propionyloxymethyl and butyryloxymethyl), aroyloxy(lower)alkyl (e.g., benzoyloxymethyl, toluoyloxymethyl and naphthoyloxymethyl), heterocyclic carbonyloxy(lower) alkyl (e.g., nicotinoyloxymethyl, isonicotinoyloxymethyl and furoyloxymethyl), and the like.

The acyl group and acyl moiety in the acyloxy, acylamino and acyloxy(lower)alkyl groups are the same as those illustrated as the acyl group for $R^1$.

Examples of the acylamino group are lower alkanoylamino (e.g., formylamino, acetylamino, propionylamino and butyrylamino), aroylamino (e.g., benzoylamino, toluoylamino and naphthoylamino), heterocyclic carbonylamino (e.g., nicotinoylamino, isonicotinoylamino and furoylamino) and the like.

Suitable protective group in the protected hydroxy and protected hydroxy(lower)alkyl groups may include acyl, mono (or di or tri)phenyl(lower)alkyl which may have one or more suitable substituent(s) (e.g., benzyl, 4-methoxybenzyl, trityl, etc.), tri-substituted silyl [e.g., tri(lower)alkylsilyl (e.g., trimethylsilyl, tert-butyldimethylsilyl, etc.), etc.], tetrahydropyranyl and the like.

The protected carboxy group is the same as those illustrated as the protected carboxy group for $R^1$.

The lower alkoxycarbonylamino group is methoxycarbonylamino, ethoxycarbonylamino, propoxycarbonylamino, isopropoxycarbonylamino, butoxycarbonylamino, isobutoxycarbonylamino, tert-butoxycarbonylamino, pentyloxycarbonylamino, hexyloxycarbonylamino and the like.

The lower alkanesulfonyl group and the lower alkanesulfonyl moiety in the lower alkanesulfonylamino group are the same as those illustrated as the lower alkanesulfonyl group for $R^1$. Examples of the lower alkanesulfonylamino group are methanesulfonylamino, ethanesulfonylamino and propanesulfonylamino.

The lower alkylureido group is methylureido, ethylureido, propylureido, isopropylureido, butylureido, isobutylureido, tert-butylureido, pentylureido, hexylureido and the like.

The lower alkyl group and lower alkyl moieties in the hydroxy(lower)alkyl, acyloxy(lower)alkyl, protected hydroxy(lower)alkyl, lower alkyl ureido, lower alkyl amino, lower alkyl carbamoyl groups are the same as those illustrated as the lower alkyl group for $R^1$ to $R^5$. Examples of hydroxy(lower)alkyl group are hydroxymethyl, hydroxyethyl, hydroxypropyl and hydroxybutyl. Examples of protected hydroxy(lower)alkyl are acetoxymethyl, acetoxyethyl, acetoxypropyl, acetoxybutyl, benzyloxymethyl, benzyloxyethyl, 4-methoxybenzyloxymethyl, 4-methoxybenzyloxyethyl, trityloxymethyl, trityloxyethyl, trimethylsilyloxymethyl, trimethylsilyloxyethyl, tert-butyldimethylsilyloxymethyl, tert-butyldimethylsilyloxymethyl, tetrahydropyranyloxymethyl and tetrahydropyranyloxyethyl. Examples of lower alkyl ureido group are methylureido, ethylureido, propylureido and butylureido. Examples of lower alkyl amino group are mono- or di-lower alkylamino group such as methylamino, dimethylamino, ethylamino, diethylamino, propylamino, butylamino. Examples of lower alkyl carbamoyl group are methylcarbamoyl, ethylcarbamoyl, propylcarbamoyl and butylcarbamoyl.

The lower alkyl group is substituted with one or more protected hydroxy groups having the acyl moiety as illustrated before.

The lower alkylenedioxy group is methylenedioxy, ethylenedioxy, propylenedioxy, isopropylidenedioxy and the like.

The aralkyloxy group is benzyloxy, phenethyloxy, phenylpropoxy, phenylbutoxy, phenylpentyloxy, phenylhexyloxy, benzhydryloxy, trityloxy, naphthylmethoxy, tolylmethoxy and the like.

The lower alkoxy group in the lower-alkoxy-substituted aralkyloxy group is the same as those illustrated as the lower alkoxy group for $R^1$, $R^3$, $R^4$ and $R^5$. Examples of the lower-alkoxy-substituted aralkyloxy group include 3,4-dimethoxybenzyloxy, 3,4-dimethoxyphenethyloxy, 3,4-dimethoxyphenylpropoxy, 3,4-dimethoxyphenylbutoxy, 3,4-dimethoxyphenylpentyloxy, 3,4-dimethoxyphenylhexyloxy, 4,4'-dimethoxybenzhydryloxy, 4,4',4''-trimethoxytrityloxy and the like.

The lower alkoxy groups in the lower-alkoxy-substituted aralkyl group for $R^3$, $R^4$ and $R^5$ are the same as those illustrated as the lower alkoxy group for $R^1$, $R^3$ to $R^5$. Examples of the lower-alkoxy-substituted aralkyl group include 3,4-dimethoxybenzyl, 3,4-dimethoxyphenethyl, 3,4-dimethoxyphenylpropyl, 3,4-dimethoxyphenylbutyl, 3,4-dimethoxyphenylpentyl, 3,4-dimethoxyphenylhexyl, 4,4'-dimethoxybenzhydryl, 4,4',4''-trimethoxytrityl and the like.

Furthermore, the lower alkylenedioxy group formed by the combination of two adjacent alkoxy groups for $R^3$ to $R^5$ is methylenedioxy, ethylenedioxy, propylenedioxy, isopropylidenedioxy and the like.

When the lower alkyl group, cycloalkyl group or heterocyclic group for $R^2$ is substituted with two or three substitutes, those substitutes may be the same or different each other.

Further, in the lower-alkoxy-substituted aralkyloxy group for $R^2$ or the lower-alkoxy-substituted aralkyl group for $R^3$ to $R^5$, the aralkyloxy or aralkyl group may be substituted with the two lower alkoxy which are the same or different each other.

It is to be noted that a hydrogen atom of CH for X can be also replaced with the substituent $R^1$ to form $CR^1$.

The pharmaceutically acceptable salts may be, for example, a salt with an alkali metal (e.g., sodium or potassium) and an alkaline earth metal (e.g., calcium or magnesium), an ammonium, an organic base (e.g., trimethylamine, triethylamine, pyridine, picoline, dicyclohexylamine or dibenzylethylenediamine), an organic acid (e.g., acetic acid, benzoic acid, succinic acid, fumaric acid, maleic acid, lactic acid, citric acid, tartaric acid, gluconic acid, methanesulfonic acid, benzenesulfonic acid, formic acid, p-toluenesulfonic acid or trifluoroacetic acid), inorganic acid (e.g., hydrogen chloride, hydrogen bromide, sulfuric acid or phosphoric acid), an amino acid (e.g., arginine, aspartic acid or glutamic acid) or the like.

The compounds of the formula (I) and (Ia), their prodrugs and pharmaceutically acceptable salts thereof may contain one or more asymmetric centers and thus they can exist as enantiomers or diastereoisomers.

The compounds of the formula (I) and (Ia), their prodrugs and pharmaceutically acceptable salts thereof may also exist in tautomeric forms and this invention includes both mixtures and separate individual tautomers.

It is further to be noted that isomerization or rearrangement of the compounds (I) and (Ia), their prodrugs and pharmaceutically acceptable salts thereof may occur by the effect of light, acid, base or the like, and the compounds obtained as the result of said isomerization or rearrangement are also included within the scope of the present invention.

The compounds of the formula (I) and (Ia), their prodrugs and pharmaceutically acceptable salts thereof can be in the form of solvates, which are included within the scope of the present invention. The solvate preferably include a hydrate and an ethanolate.

Also included in the scope of the invention are radiolabelled derivatives of compounds of formula (I) and (Ia), their prodrugs and pharmaceutically acceptable salts thereof which are suitable for biological studies.

Preferred embodiments of the compound are represented by the formula (Ia), wherein $X^a$ is nitrogen atom and $R^{1a}$–$R^{5a}$, $Y^a$ and m are the same as those defined before, its prodrug or a pharmaceutically acceptable salt thereof.

Another preferred embodiments of the compounds are represented by the formula (Ia), wherein $R^{1a}$ is cyano group; nitro group; carbamoyl group; a lower alkylcarbamoyl group which may be substituted with a heterocyclic group; carboxy group; a lower alkoxycarbonyl group; a lower alkyl group; a halo(lower)alkyl group; a lower alkanoyl group; an aroyl group; or a lower alkanesulfonyl group, $R^{2a}$ is a cycloalkyl group which has one to three substituents selected from the group consisting of hydroxy, acyloxy, acyl, lower-alkoxy-substituted aralkyloxy, amino, acylamino, lower alkoxycarbonylamino, lower alkanesulfonylamino, ureido, lower alkylureido, sulfamoylamino, lower alkoxycarbonyl, lower alkanesoulfonyl, lower alkyl, hydroxy(lower)alkyl, acyloxy(lower)alkyl, lower alkylenedioxy, carbamoyl, and sulfamoyl; and $X^a$, $Y^a$, $R^{3a}$, $R^{4a}$, $R^{5a}$ and m are the same as those defined before, its prodrug or a pharmaceutically acceptable salt thereof.

Another preferred embodiments of the compounds are represented by the formula (Ia), wherein $R^{1a}$ is cyano group; nitro group; carbamoyl group; a lower alkylcarbamoyl group which may be substituted with a heterocyclic group; carboxy group; a lower alkoxycarbonyl group; a lower alkyl group; a halo(lower)alkyl group; a lower alkanoly group; an aroyl group; or a lower alkanesulfonyl group, $R^{2a}$ is a cyclohexyl group which has one to three substituents selected from the group consisting of hydroxy, lower alkanoyloxy, acyl, lower-alkoxy-substituted aralkyloxy, amino, lower alkanoylamino, lower alkoxycarbonylamino, lower alkanesulfonylamino, ureido, lower alkylureido, sulfamoylamino, lower alkoxycarbonyl, lower alkanesulfonyl, lower alkyl, hydroxy(lower)alkyl, lower alkanoyloxy(lower)alkyl, lower alkylenedioxy, carbamoyl and sulfamoyl; and $X^a$, $Y^a$, $R^{3a}$, $R^{4a}$, $R^{5a}$ and m are the same as those defined before, its prodrug or a pharmaceutically acceptable salt thereof.

Another preferred embodiments of the compounds are represented by the formula (Ia), wherein $R^{1a}$ is cyano group, $R^{2a}$ is a cyclohexyl group which has hydroxy or lower alkanoyloxy, $R^{3a}$ is a hydrogen atom, $R^{4a}$ is a halogen atom, $R^{5a}$ is a lower alkoxy group, $X^a$, $Y^a$ and m are the same as those defined before, its prodrug or a pharmaceutically acceptable salt thereof.

Another preferred embodiments of the compound are represented by the formula (Ia), wherein $X^a$ is CH;

$Y^a$ is oxygen atom or sulfur atom;

$R^{1a}$ is cyano group; nitro group; carbamoyl group; a lower alkylcarbamoyl group which may be substituted with a heterocyclic group; carboxy group; a protected carboxy group; a lower alkyl group; a halo(lower)alkyl group; an acyl group; or a lower alkanesulfonyl group, $R^{2a}$ is a lower alkyl group, a cycloalkyl group or a heterocyclic group, each of which has one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, carboxy, lower alkanesulfonyl, lower alkylenedioxy, carbamoyl, lower alkyl carbamoyl and sulfamoyl;

$R^{3a}$, $R^{4a}$ and $R^{5a}$ are, the same or different, hydrogen atom, a halogen atom, a lower alkanoyl group, carboxy group, a protected carboxy group, carbamoyl group, nitro group, cyano group, a lower alkyl group optionally substituted by hydroxy, a lower alkoxy group or a lower-alkoxy-substituted aralkyl group; or two of $R^{3a}$, $R^{4a}$ and $R^{5a}$ may combine together to form a lower alkylenedioxy group, m is an integer of 1, its prodrug or a pharmaceutically acceptable salt thereof.

The most preferred embodiments of the compounds are 1-(3-chloro-4-methoxybenzyl)-6-cyano-3-(trans-4-hydroxycyclohexyl)-2,3-dihydro-1H-imidazo[4,5-b] pyridin-2-one, 1-(3-bromo-4-methoxybenzyl)-6-cyano-3-(trans4-hydroxycyclohexyl)-2,3-dihydro-1H-imidazo[4,5-b] pyridin-2-one, and 1-(3-chloro-4-methoxybenzyl)-6-cyano-3-(cis-4-hydroxycyclohexyl)-2,3-dihydro-1H-imidazo[4,5-b] pyridin-2-one.

According to the present invention, the above mentioned compound (I), its prodrug or pharmaceutically acceptable salt thereof is used as a pharmaceutical composition or medicament usually in admixture with a pharmaceutically acceptable carrier or diluent.

Preferred embodiments of the pharmaceutical composition of the present invention contain a compound of the formula (I), wherein X is nitrogen atom and $R^1$–$R^5$, Y and n are the same as those defined before, its prodrug or a pharmaceutically acceptable salt thereof as an active ingredient in admixture with a pharmaceutically acceptable carrier or diluent.

Another preferred embodiments of the pharmaceutical composition contain a compound of the formula (I), wherein $R^2$ is a cycloalkyl group which may have one to three substituents selected from the group consisting of hydroxy, protected hydroxy, acyl, lower-alkoxy-substituted aralkyloxy, amino, acylamino, lower alkoxycarbonylamino, lower alkanesulfonylamino, ureido, lower alkylureido, sulfamoylamino, protected carboxy, lower alkanesulfonyl, lower alkyl, hydroxy(lower)alkyl, protected hydroxy(lower) alkyl, lower alkylenedioxy, carbamoyl and sulfamoyl, and X, Y, $R^1$, $R^3$, $R^4$, $R^5$ and n are the same as those defined in the above, its prodrug or a pharmaceutically acceptable salt thereof as an active ingredient in admixture with a pharmaceutically acceptable carrier or diluent.

The prodrug of the compound (Ia) is intended to mean a chemically modified derivative of the compound (Ia) which itself does not show a pharmacological activity but may be catalytically or non-catalytically decomposed or metabolized in human or animal bodies into its pharmacologically active form. Examples of the prodrugs of the compounds (Ia) are easily hydrolyzeable esters of the compounds (Ia).

According to this invention, the compound (I) or its salts can be prepared by the following process.

Process 1

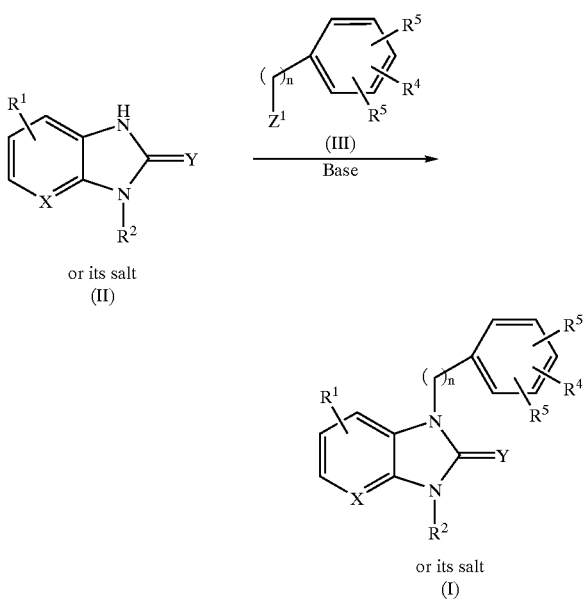

In the above formula, $R^1$, $R^2$, $R^3$, $R^4$, $R^5$, X, Y and n are the same as above and $Z^1$ is a halogen atom.

Some of the starting materials are novel and can be prepared by the following process.

Process A

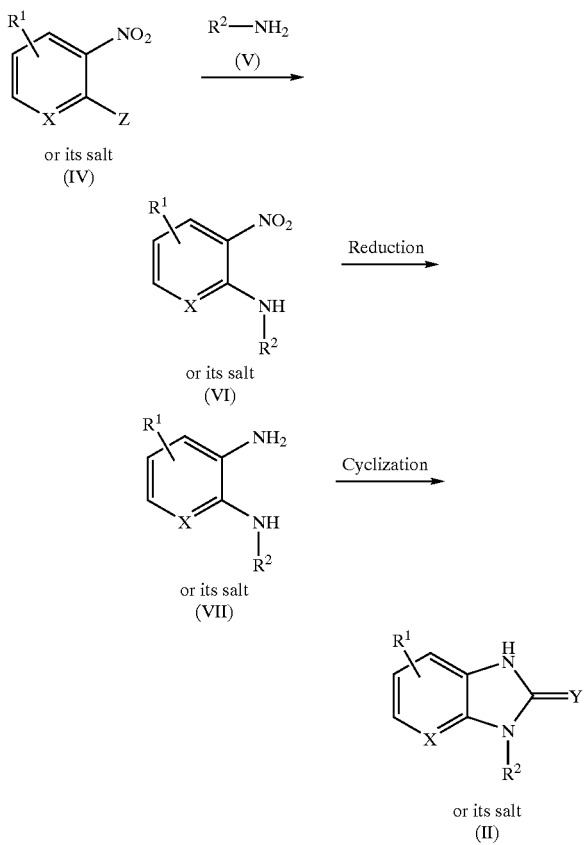

In the above formula, $R^1$, $R^2$, X and Y are the same as above, and Z is a halogen atom or hydroxy group.

The processes for preparing the starting compounds and the final compounds (I) and (Ia) of the present invention are explained in detail in the following.

Process 1

A compound (I) or its salt can be prepared by reacting a compound (II) or its salt with a compound (III).

This reaction is usually carried out in the presence of an inorganic or organic base.

Preferable inorganic bases include an alkali metal [e.g., sodium or potassium], an alkali metal hydroxide [e.g., sodium hydroxide or potassium hydroxide], an alkali metal hydrogen carbonate [e.g., sodium hydrogen carbonate or potassium hydrogen carbonate], an alkali metal carbonate [e.g., sodium carbonate], an alkaline earth metal carbonate [e.g., calcium carbonate], an alkali metal hydride [e.g., sodium hydride or potassium hydride] and the like.

Preferable organic bases include tri(lower)alkylamines [e.g., triethylamine or N,N-diisopropylethylamine], alkyl lithiums [e.g., methyl lithium or butyl lithium], lithium diisopropylamide, lithium hexamethyldisilazido and the like.

The reaction is usually carried out in a conventional solvent such as tetrahydrofuran, dioxane, toluene, methylene chloride, chloroform, N,N-dimethylformamide or any other organic solvent which does not adversely affect the reaction, or a mixture thereof.

In the case where the compound (I) contains a group for $R^1$ and/or $R^2$ which can be converted to another group belonging to $R^1$ and/or $R^2$ respectively, said compound (I) can be optionally converted to another compound (I) by a conventional method.

For example, a compound (I) containing a protected carboxy group can be hydrolyzed with an alkali metal hydroxide [e.g., sodium hydroxide or potassium hydroxide] to give a compound (I) containing carboxy group. Further, a compound (I) containing amino group can be reacted with metal isocyanate (e.g., potassium isocyanate) to give a compound (I) containing ureido group.

Concretely, such conversions can be carried out in accordance with a method described in Examples or by a similar method thereto.

A pharmaceutically acceptable salt of the compound (I) and (Ia) and their prodrugs can be prepared by treating a compound (I) and (Ia) and their prodrugs with an appropriate base or acid in accordance with the conventional method, respectively.

Process A

A compound (II) or its salt can be prepared by
1) aminating a compound (IV) or its salt with a compound (V) to give a compound (VI) or its salt,
2) reducing a nitro group of the compound (VI) or its salt to give a compound (VII) or its salt, and then
3) intramolecular-cyclizing two amino groups of the compound (VII) or its salt by using a coupling agent as illustrated in Preparations or by a similar method thereto.

Process A-1)

A compound (IV) or its salt can be aminated with an amine compound (V) to give a compound (VI) or its salt. Amination condition can vary depend on the group Z of the compound (IV) or its salt. When Z is a halogen atom such as fluorine or chlorine, amination can occur between the compound (IV) or its salt and the amine compound (V) under mild heating without any particular activation of the group Z of the compound (IV) or its salt. When the group Z is hydroxy, the hydroxy group for Z needs to be activated by the reaction with $SOCl_2$ or mesyl chloride. Then, activated compound (IV) or its salt can be aminated with the amine compound (V) at room temperature or under cooling. The reaction is usually carried out in a conventional solvent such as tetrahydrofuran, dioxane, toluene, methylene chloride, chloroform, N,N-dimethylformamide or any other organic solvent which does not adversely affect the reaction, or a mixture thereof.

Process A-2)

A compound (VI) or its salt can be reduced by a well-known method in the art such as catalytic reduction. The reduction is carried out in a conventional manner, including a chemical reduction and a catalytic reduction.

Suitable reducing agents to be used in the chemical reduction are a combination of metals (e.g., tin, zinc or iron) or metallic compounds (e.g., chromium chloride or chromium acetate) and organic or inorganic acids (e.g., formic acid, acetic acid, propionic acid, trifluoroacetic acid, p-toluenesulfonic acid, hydrochloric acid or hydrobromic acid).

Suitable catalysts to be used in the catalytic reduction are conventional ones such as platinum catalysts (e.g., platinum plate, spongy platinum, platinum black, colloidal platinum, platinum oxide or platinum wire), palladium catalysts (e.g., spongy palladium, palladium black, palladium oxide, palladium on carbon, colloidal palladium, palladium on barium sulfate or palladium on barium carbonate), nickel catalysts (e.g., reduced nickel, nickel oxide or Raney nickel), cobalt catalysts (e.g., reduced cobalt or Raney cobalt), iron catalysts (e.g., reduced iron or Raney iron), copper catalysts (e.g., reduced copper, Raney copper or Ullman copper) and the like. The reduction is usually carried out in a conventional solvent which does not adversely influence the reaction such as water, methanol, ethanol, propanol, N,N-dimethylformamide, tetrahydrofuran or a mixture thereof. Additionally, in the case where the above-mentioned acid to be used in the chemical reduction is in liquid, it can also be used as a solvent.

The reaction is usually carried out under cooling to warming since the reaction temperature of the reduction is not critical.

In the case where the compound (VI) or its salt contains a group for $R^1$ and/or $R^2$ which can be converted to another group belonging to $R^1$ and/or $R^2$ respectively, said compound (VI) or its salt can be optionally converted to another compound (VI) or its salt by a conventional method. For example, a compound (VI) or its salt containing a hydroxy group can be acylated with acyl chloride [e.g., acetyl chloride] to give a compound (VI) or its salt containing an acetoxy group. Further, a compound (VI) or its salt containing an amino group can be reacted with di-tert-butyl dicarbonate to give a compound (VI) or its salt containing a tert-butoxycarbonyl group.

Process A-3)

A compound (VII) or its salt can be intramolecular-cyclized by a coupling agent such as 1,1'-carbonyldiimidazole, triphosgene or 1,1'-thiocarbonyldiimidazole. The reaction is usually carried out in a conventional solvent such as tetrahydrofuran, dioxane, toluene, methylene chloride, chloroform, N,N-dimethylformamide or any other organic solvent which does not adversely affect the reaction, or a mixture thereof. The reaction is usually carried out under cooling to heating since the reaction temperature is not critical.

The compounds (I) including the compounds (Ia) and pharmaceutically acceptable salts thereof possess inhibitory activity of cGMP-PDE (especially PDE-V) known to be involved in relaxant activity of smooth muscle, bronchodilator activity, vasodilative activity, relaxant activity of the penile corpus cavernosum, inhibitory activity of smooth muscle cells proliferation, inhibitory activity of allergy, and so on.

Therefore, the compounds (I) including the compounds (Ia) and pharmaceutically acceptable salts thereof may be useful for the treatment or prevention of various diseases, such as angina, hypertension, pulmonary hypertension, congestive heart failure, glomerular diseases (e.g., diabetic glomerulosclerosis), renal tubulo-intestinal diseases (e.g., nephropathy induced by tacrolimus, cyclosporin or the like), renal failure, atherosclerosis, conditions of reduced blood vessel patency (e.g., post-percutaneous transluminal coronary angioplasty), peripheral vascular disease, stroke, chronic reversible obstructive lung diseases (e.g., bronchitis or asthma (chronic asthma, allergic asthma)), allergic rhinitis, urticaria, glaucoma, diseases characterized by disorders of gut motility (e.g., irritable bowel syndrome), erectile dysfunction (e.g., organic erectile dysfunction or psychic erectile dysfunction), female sexual dysfunction, impotence, or diabetic complications (e.g., diabetic gangrene, diabetic arthropathy, diabetic glomerulosclerosis, diabetic dermopathy, diabetic neuropathy, diabetic cataract or diabetic retinopathy).

Specifically, the compounds (I) and (Ia) and pharmaceutically acceptable salts thereof are also useful for the treatment and/or prevention of micturition disorder, incontinence or storage of urine disorder (such as the ones ascribed to nerve regressive affection, inflammation, injury, neoplasm, diabetes mellitus, cerebral vascular accident, surgery, prostatomegaly, urethra relaxation incompetence, dysuria).

It is to be noted that improvement of sexual performance is also included in the treatment of erectile dysfunction or impotence.

The compounds (I) and (Ia) and their salts of the present invention have much advantages, such as stronger activity, more suitable half-life, decreased adverse effect, or the lie, compared to the known anthranilic acid derivatives having an inhibitory activity of cGMP-PDE, which are shown in the prior arts.

In order to exhibit the usefulness of the present invention, the activities of the compounds (I) are shown in the following.

[I] Test Compound

The test compounds were obtained in each Example shown in Table 1.

[II] Test Method: cGMP-Phosphodiesterase (PDE) Assay

Human platelet cGMP-PDE was separated from other isozymes in human platelets by a modification of the method of Thompson et. al. (see Cyclic Nucleotide Phosphodiesterase (PDE), in Methods of Enzymatic analysis, Vol 4, p127–234, 1984). Specific inhibitory activity of PDE-V was measured by following procedure. In enzyme inhibition assays, the test compounds were dissolved in DMSO and then diluted with assay buffer (50 mM Tris-HCl, 0.077 mg/ml dithiothreitol and 10 mg/ml snake venom, 1 mM EGTA, pH 8.0), at final concentrations ranging from $10^{-10}$ to $10^{-6}$ M. Assays were performed at 0.1 μM substrate ([$^3$H]-cGMP) concentration, at 30° C. for 10 minutes using enzyme dilutions which gave 10–20% hydrolysis of substrate. Each assay was initiated by addition of substrate and terminated by addition of anion exchange resin (Dowex® 1-X8, 250 mg/mg) followed by centrifugation for 10 minutes (3000 rpm, at 4° C.). Radioactivity of supernatant ([$^3$H]-GMP) was assayed by liquid scintillation counting.

The results in enzymatic inhibitory test against human platelet PDE-V are shown in Table 1.

TABLE 1

| Test Compound (Example No.) | Inhibitory activity IC$_{50}$ (nM) |
|---|---|
| Example 2(21) | <10 |
| Example 2(60) | <10 |
| Example 2(81) | <10 |
| Example 2(95) | <10 |
| Example 2(109) | <10 |
| Example 4(2) | <10 |
| Example 28 | <10 |
| Example 33 | <10 |

As shown in the above Table 1, the compounds (I) of the present invention have superior inhibitory activity against cGMP-PDE.

The compound (Ia), its prodrug and its salt can be administered alone and the compound (Ia) and (I), their prodrugs and their salts can be administered in a form of a composition in admixture of a pharmaceutical acceptable carrier or diluent.

The active ingredient of this invention can be used in a form of a pharmaceutical preparation, for example, in solid, semisolid or liquid form, which contains a compound (Ia) or (I), its prodrug or a pharmaceutically acceptable salt thereof as an active ingredient, in admire with an organic or inorganic carrier or diluent suitable for external, enteral, intravenous, intramuscular, parenteral or intramucous applications. The active ingredient may be compounded, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use.

The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient may be compounded into, for example, preparations for oral application, preparations for injection, preparations for external application, preparations for inhalation, preparations for application to mucous membranes (oral mucous membrane, fascia penis, facies urethralis penis, etc.).

Mammals which may be treated by the present invention include livestock mammals such as cows, horses, etc., domestic animals such as dogs, cats, rats, etc. and humans, preferably humans.

While the dosage of therapeutically effective amount of a compound (I) or (Ia), its salt or a pharmaceutically acceptable salt thereof varies from and also depends upon the age and condition of each individual patient to be treated, in case of the systemic administration, a daily dose of about 0.01–1000 mg, preferably 0.1–500 mg and more preferably 0.5–100 mg of the active ingredient is generally given for treating the diseases, and an average single dose of about 0.2–0.5 mg, 1 mg, 5 mg, 10 mg, 50 mg, 100 mg, 250 mg and 500 mg is generally administered. Daily doses for chronic administration in humans will be in the range of about 0.3 mg/body to 1,000 mg/body.

The patents, patent applications and publications cited herein above are incorporated by reference.

BEST MODE FOR CARRYING OUT THE INVENTION

The following Examples are given only for the purpose of illustrating the present invention in more detail.

PREPARATION 1

A mixture of 2-hydroxy-3-nitro-5-(trifluoromethyl) pyridine (5.0 g), thionyl chloride(28 mL) and N,N-dimethylformamide (3 mL) was heated under reflux for 5 hours. The reaction mixture was concentrated in vacuo, and ice was added to the residue. The mixture was extracted with a mixture of ethyl acetate and tetrahydrofuran. The separated organic layer was washed with brine, dried over.magnesium sulfate, and evaporated in vacuo. The residue was subjected to a silica gel column chromatography eluting with a mixture of n-hexane and ethyl acetate (5:1) and then to an aluminum oxide (activated, basic) column chromatography eluting with ethyl acetate to give 2-chloro-3-nitro-5-(trifluoromethyl)pyridine (4.89 g) as a yellow oil.

NMR(DMSO-d$_6$, δ): 9.08(1H, d, J=2.0 Hz), 9.21(1H, d, J=2.0 Hz).

PREPARATION 2

Fuming nitric acid (10.4 mL) was added dropwise to a mixture of 6-hydroxynicotinic acid (15 g) and concentrated sulfuric acid(45 mL) at 0° C. The reaction mixture was slowly heated to 45° C. and maintained at the same temperature for 3 hours. The mixture was poured into a mixture of ice and water. The resultant precipitate was collected by suction filtration, washed with water, and air-dried to give 6-hydroxy-5-nitronicotinic acid (8.63 g) as a pale yellow solid.

mp. 277–278° C.

NMR(DMSO-d$_6$, δ): 8.37(1H, d, J=2.5 Hz), 8.65(1H, d, J=2.5 Hz).

MS m/z: 183(M$^+$–1).

PREPARATION 3

A mixture of 6-hydroxy-5-nitronicotinic acid (7.58 g) and thionyl chloride (48.1 mL) were refluxed under nitrogen atmosphere for 2 hours. After cooling to room temperature, the reaction mixture was concentrated in vacuo. The residue was dissolved in dichloromethane (10 mL). The resultant solution was added dropwise to a mixture of ammonium hydroxide (28% NH$_3$ in water, 20 mL) and dichloromethane (10 mL) at 0° C. with stirring. The resulting precipitate was collected by suction filtration and washed with water to give 6-hydroxy-5-nitronicotinamide (4.97 g) as a yellow solid.

mp. 280–281° C.

NMR(DMSO-d$_6$, δ): 6.98(1H, br), 7.67(1H, br), 8.51(1H, d, J=2.5 Hz), 8.58(1H, d, J=2.5 Hz).

MS m/z: 182(M$^+$–1).

PREPARATION 4

Phosphorus oxychloride (2.99 mL) was added dropwise to N,N-dimethylformamide (49 mL) at 0° C., and the mixture was stirred at the same temperature for 15 minutes. Then 6-hydroxy-5-nitronicotinamide (4.9 g) was added portionwise to the mixture, and the reaction mixture was stirred at 50° C. for an hour. Water was added to the reaction mixture at 0° C., and the resulting precipitate was collected by filtration in vacuo. The obtained solid was washed with water to give 5-cyano-2-hydroxy-3-nitropyridine (3.17 g) as a pale brown solid.

mp. 294.5–295° C.

NMR(DMSO-$d_6$, δ) 8.69(1H, d, J=2.5 Hz), 8.79(1H, d, J=2.5 Hz).

MS m/z: 164M$^+$–1).

PREPARATION 5

To a suspension of 4-chloro-3-nitrobenzoic acid (10 g) and potassium carbonate (7.54 g) in N,N-dimethylformamide (100 mL) was added methyl iodide (3.24 mL) at room temperature under nitrogen atmosphere. The reaction mixture was stirred at room temperature for 3.5 hours. The reaction mixture was diluted with ethyl acetate and washed successively with 1 N-hydrochloric acid, water, an aqueous saturated sodium hydrogencarbonate solution and brine. The organic layer was dried over anhydrous magnesium sulfate and concentrated in vacuo. The residual solid was washed with diisopropyl ether to give methyl 4-chloro-3-nitrobenzoate (9.51 g) as a yellow solid.

mp. 78–80° C.

NMR(DMSO-$d_6$, δ): 3.91(3H, s), 7.95(1H, d, J=8.5 Hz), 8.20(1H, dd, J=8.5, 2.0 Hz), 8.54(1H, d, J=2.0 Hz).

PREPARATION 6

To a solution of 4-fluoro-3-nitrobenzotrifluoride (4 g) in N,N-dimethylformamide (40 mL) was added trans-4-aminocyclohexanol (6.61 g), and the mixture was stirred at 90° C. for 4 hours under nitrogen atmosphere. After cooling to room temperature, water was added to the mixture. The resulting precipitate was collected by filtration and washed with water to give 4-(trans-4-hydroxycyclohexylamino)-3-nitrobenzotrifluoride (5.4 g) as a yellow solid.

mp. 136–137° C.

NMR(DMSO-$d_6$, δ): 1.27–1.53(4H, m), 1.78–1.89(2H, m), 1.94–2.05(2H, m), 3.41–3.55(1H, m), 3.61–3.75(1H, m), 4.65(1H, d, J=4.5 Hz), 7.33(1H, d, J=9.0 Hz), 7.78(1H, dd, J=9.0, 2.0 Hz), 8.14(1H, d, J=7.5 Hz), 8.31(1H, d, J=2.0 Hz).

MS m/z: 303(M$^+$–1).

PREPARATION 7

The following compounds described in (1) to (25) were obtained in a manner similar to Preparation 6.

(1) 4-(trans-4-Hydroxycyclohexylamino)-3-nitrobenzonitrile mp. 181–183° C.

NMR(DMSO-$d_6$, δ): 1.26–1.51(4H, m), 1.76–1.87(2H, m), 1.90–2.01(2H, m), 3.40–3.54(1H, m), 3.61–3.75(1H, m), 4.64(1H, d, J=4.0 Hz), 7.28(1H, d, J=9.0 Hz), 7.82(1H, dd, J=8.0, 2.5 Hz), 8.20(1H, d, J=8.0 Hz), 8.51(1H, d, J=2.5 Hz).

MS m/z: 260(M$^+$–1).

(2) 4-(trans-4-Hydroxycyclohexylamino)-3-nitroacetophenone mp. 182.5–183° C.

NMR(DMSO-$d_6$, δ): 1.27–1.52(4H, m), 1.78–1.88(2H, m), 1.95–2.04(2H, m), 2.52(3H, s), 3.39–3.54(1H, m), 3.63–3.76(1H, m), 4.65(1H, d, J=4.0 Hz), 7.23(1H, d, J=9.0 Hz), 8.01(1H, dd, J=9.0, 2.5 Hz), 8.24(1H, d, J=7.5 Hz), 8.63(1H, d, J=2.5 Hz).

MS m/z: 277(M$^+$–1).

(3) 2-(trans-4-Hydroxycyclohexylamino)-5-(methylsulfonyl)nitrobenzene mp. 211.5–213° C.

NMR(DMSO-$d_6$, δ): 1.28–1.53(4H, m), 1.78–1.88(2H, m), 1.93–2.04(2H, m), 3.21(3H, s), 3.42–3.55(1H, m), 3.64–3.77(1H, m), 4.65(1H, d, J=4.0 Hz), 7.36(1H, d, J=9.5 Hz), 7.90(1H, dd, J=9.5, 2.5 Hz), 8.24(1H, d, J=8.0 Hz), 8.50(1H, d, J=2.5 Hz).

MS m/z : 313(M$^+$–1).

(4) 4-(trans-4-Hydroxycyclohexylamino)-3-nitrobenzophenone mp. 184–185° C.

NMR(DMSO-$d_6$, δ): 1.29–1.55(4H, m), 1.80–1.90(2H, m), 1.95–2.06(2H, m), 3.42–3.55(1H, m), 3.65–3.79(1H, m), 4.65(1H, d, J=4.0 Hz), 7.32(1H, d, J=9.5 Hz), 7.57(1H, t, J=7.5 Hz), 7.58(1H, d, J=7.5 Hz), 7.63–7.73(3H, m), 7.94(1H, dd, J=9.5, 2.0 Hz), 8.29(1H, d, J=7.5 Hz), 8.43(1H, d, J=2.0 Hz).

MS m/z: 339(M$^+$–1).

(5) 4-[((R)-2-Hydroxy-1-methylethyl)amino]-3-nitrobenzonitrile

NMR(DMSO-$d_6$, δ): 1.21 (3H, d, J=7.5 Hz), 3.45–3.63 (2H, m), 3.90–4.05 (1H, m), 5.14 (1H, t, J=5 Hz), 7.25 (1H, d, J=8 Hz), 7.82 (1H, dd, J=8, 2 Hz), 8.45–8.56 (2H, m).

(6) 4-[((S)-2-Hydroxy-1-methylethyl)amino]-3-nitrobenzonitrile

NMR(DMSO-$d_6$, δ): 1.21 (3H, d, J=7.5 Hz), 3.45–3.63 (2H, m), 3.90–4.05 (1H, m), 5.14 (1H, t, J=5 Hz), 7.25 (1H, d, J=8 Hz), 7.82 (1H , dd, J=8, 2 Hz), 8.45–8.56 (2H, m).

(7) 4-[(trans-4-Formamidocyclohexyl)amino]-3-nitrobenzonitrile

NMR(DMSO-$d_6$, δ): 1.30–1.60 (4H, m), 1.76–1.92 (2H, m), 1.92–2.06 (2H, m), 3.55–3.78 (2H, m), 7.32 (1H, d, J=8 Hz), 7.82 (1H, dd, J=8, 2 Hz), 7.95 (1H, s), 8.06 (1H, d, J=8 Hz), 8.21 (1H, d, J=8 Hz), 8.52 (1H, d, J=2 Hz).

(8) 4-[2-Hydroxy-1-(hydroxymethyl)ethylamino]-3-nitrobenzonitrile

NMR(DMSO-$d_6$, δ): 3.51–3.66 (4H, m), 3.78–3.90 (1H, m), 5.06 (2H, t, J=5 Hz), 7.30 (1H, d, J=8 Hz), 7.83 (1H, dd, J=8, 2 Hz), 8.52 (1H, d, J=2 Hz), 8.67 (1H, d, J=8 Hz).

(9) 4-(1,1-Dimethyl-2-hydroxyethylamino)-3-nitrobenzonitrile

NMR(CDCl$_3$, δ): 1.51 (6H, s), 1.88 (1H, br), 3.72 (2H, d, J=5 Hz), 7.17 (1H, d, J=8 Hz), 7.54 (1H, dd, J=8, 2 Hz), 8.53 (1H, d, J=2 Hz), 8.96 (1H, br).

(10) 4-(1,1-Dimethyl-2-hydroxyethylamino)-3-nitrobenzotrifluoride

NMR(CDCl$_3$, δ): 1.51 (6H, s), 1.84 (1H, t, J=5 Hz), 3.74 (2H, d, J=5 Hz), 7.20 (1H, d, J=8 Hz), 7.56 (1H, dd, J=8, 2 Hz), 8.48 (1H, d, J=2 Hz), 8.78 (1H, br s).

(11) 4-[(S)-1-tert-Butoxycarbonylpyrrolidin-3-ylamino]-3-nitrobenzonitrile

NMR(CDCl$_3$, δ):1.48 (9H, s), 2.05 (1H, br), 2.28–2.42 (1H, m), 3.26–3.48 (1H, m), 3.48–3.64 (2H, m), 3.75–3.86 (1H, m), 4.24 (1H, br), 6.94 (1H, d, J=8 Hz), 7.64 (1H, d, J=8 Hz), 8.46 (1H, d, J=5 Hz), 8.53 (1H, s-like).

(12) 4-[(R)-1-tert-Butoxycarbonylpyrrolidin-3-ylamino]-3-nitrobenzonitrile

NMR(CDCl$_3$, δ): 1.48 (9H, s), 2.05 (1H, br), 2.28–2.42 (1H, m), 3.26–3.48 (1H, m), 3.48–3.64 (2H, m), 3.75–3.86 (1H, m), 4.24 (1H, br), 6.94 (1H, d, J=8 Hz), 7.64 (1H, d, J=8 Hz), 8.46 (1H, d, J=5 Hz), 8.53 (1H, s-like).

(13) 4-[1-(Hydroxymethyl)cyclopentylamino]-3-nitrobenzonitrile

NMR(CDCl$_3$, δ): 1.66–1.93 (5H, m), 1.93–2.11 (4H, m), 3.80 (2H, d, J=4 Hz), 7.06 (1H, d, J=8 Hz), 7.53 (1H, dd, J=8, 2 Hz), 8.53 (1H, d, J=2 Hz), 8.77 (1H, br s).

(14) 4-Cyclopentylamino-3-nitrobenzonitrile

NMR(CDCl$_3$, δ): 1.59–1.91 (6H, m), 2.06–2.23 (2H, m), 3.94–4.06 (1H, m), 6.95 (1H, d, J=8 Hz), 7.57 (1H, dd, J=8, 2 Hz), 8.44 (1H, br s), 8.51 (1H, d, J=2 Hz).

(15) 3-Nitro-4-(tetrahydro-4H-pyran-4-ylamino) benzonitrile

NMR(CDCl$_3$, δ): 1.63–1.83 (2H, m), 2.01–2.14 (2H, m), 3.51–3.64 (2H, m), 3.70–3.86 (1H, m), 3.98–4.10 (2H, m), 6.94 (1H, d, J=8 Hz), 7.60 (1H, dd, J=8, 2 Hz), 8.45 (1H, br d, J=8 Hz), 8.53 (1H, d, J=2 Hz).

(16) 4-Cyclohexylamino-3-nitrobenzonitrile

NMR(CDCl$_3$, δ): 1.23–1.51 (5H, m), 1.61–1.75 (1H, m), 1.75–1.92 (2H, m), 1.96–2.14 (2H, m), 3.54 (1H, br s), 6.92 (1H, d, J=8 Hz), 7.55 (1H, d, J=8 Hz), 8.45 (1H, br), 8.50 (1H, s).

MS m/z: 244.2(M$^+$–1).

(17) 4-tert-Butylamino-3-nitrobenzonitrile

NMR(CDCl$_3$, δ): 1.54 (9H, s), 7.15 (1H, d, J=8 Hz), 7.54 (1H, dd, J=8, 2 Hz), 8.53 (1H, d, J=2 Hz), 8.73 (1H, br s).

MS m/z: 218.2(M$^+$–1).

(18) 4-Cycloheptylamino-3-nitrobenzonitrile

NMR(CDCl$_3$, δ): 1.46–1.82 (10H, m), 1.94–2.11 (2H, m), 3.64–3.79 (1H, m), 6.84 (1H, d, J=8 Hz), 7.56 (1H, dd, J=8, 2 Hz), 8.41–8.56 (2H, m).

(19) 4-[((S)-1-Ethyl-2-hydroxyethyl)amino]-3-nitrobenzonitrile

NMR(CDCl$_3$, δ): 1.03 (3H, t, J=7.5 Hz), 1.61–1.91 (3H, m), 3.65–3.90 (3H, m), 7.02 (1H, d, J=8 Hz), 7.56 (1H, dd, J=8, 2 Hz), 8.52 (1H, d, J=2 Hz), 8.56 (1H, br).

(20) 4-[((R)-1-Ethyl-2-hydroxyethyl)amino]-3-nitrobenzonitrile

NMR(CDCl$_3$, δ): 1.03 (3H, t, J=7.5 Hz), 1.61–1.91 (3H, m), 3.65–3.89 (3H, m), 7.02 (1H, d, J=8 Hz), 7.56 (1H, dd, J=8, 2 Hz), 8.52 (1H, d, J=2 Hz), 8.55 (1H, br).

(21) 4-[1-(tert-Butoxycarbonyl)piperidin-4-ylamino]-3-nitrobenzonitrile

NMR(CDCl$_3$, δ): 1.48 (9H, s), 1.50–1.71 (2H, m), 1.99–2.13 (2H, m), 2.96–3.11 (2H, m), 3.61–3.77 (1H, m), 3.99–4.13 (2H, m), 6.94 (1H, d, J=8 Hz), 7.60 (1H, dd, J=8, 2 Hz), 8.44 (1H, d, J=8 Hz), 8.53 (1H, d, J=2 Hz).

MS m/z: 345.2(M$^+$–1).

(22) 4-(t-3,t-4-Dihydroxy-r-1-cyclohexylamino)-3-nitrobenzonitrile

NMR(DMSO-d$_6$, δ): 1.37–1.86 (4H, m), 1.86–2.06 (2H, m), 3.44–3.55 (1H, m), 3.75–3.85 (1H, m), 3.85–4.03 (1H, m), 4.50 (1H, d, J=5 Hz), 4.58 (1H, d, J=3 Hz), 7.16 (1H, d, J=8 Hz), 7.84 (1H, dd, J=8, 2 Hz), 8.20 (1H, d, J=8 Hz), 8.51 (1H, s).

(23) 4-(c-3,c-4-Dihydroxy-r-1-cyclohexylamino)-3-nitrobenzonitrile

NMR(DMSO-d$_6$, δ): 1.47–1.50 (1H, m), 1.50–1.91 (5H, m), 3.50–3.60 (1H, m), 3.72–3.80 (1H, m), 3.87–3.97 (1H, m), 4.50 (1H, d, J=5 Hz), 4.94 (1H, d, J=5 Hz), 7.20 (1H, d, J=8 Hz), 7.80 (1H, dd, J=8, 2 Hz), 8.51 (1H, d, J=2 Hz) 9.25 (1H, br).

(24) 4-(3-Hydroxypropylamino)-3-nitrobenzonitrile

NMR (CDCl$_3$, δ): 1.95–2.07 (2H, m), 3.54 (2H, q, J=5 Hz), 3.88 (2H, q, J=5 Hz), 6.96 (1H, d, J=8 Hz), 7.60 (1H, d, J=8 Hz), 8.51 (1H, s), 8.69 (1H, br peak).

MS (ES-) m/z: 220.1(M$^+$–1).

(25) 4-[2-(N,N-Dimethylamino)ethylamino]-3-nitrobenzonitrile

NMR (CDCl$_3$, δ): 2.65 (2H, t, J=5 Hz), 3.37 (2H, q, J=5 Hz), 6.88 (1H, d, J=8 Hz), 7.58 (1H, dd, J=8, 2 Hz,) 8.51 (1H, d, J=2 Hz), (1H, br peak).

PREPARATION 8

To a solution of 2-chloro-3-nitro-5-(trifluoromethyl) pyridine (1 g) in N,N-dimethylformamide (10 mL) was added 2-amino-2-methyl-1-propanol (1.18 g) at 0° C. The mixture was stirred at room temperature for 3.5 hours under nitrogen atmosphere. The mixture was diluted with ethyl acetate and washed successively with water and brine. The organic layer was dried over anhydrous magnesium sulfate and concentrated in vacuo to give 2-(1,1-dimethyl-2-hydroxyethylamino)-3-nitro-5-(trifluoromethyl)pyridine (1.23 g) as a yellow oil.

NMR(DMSO-d$_6$, δ): 1.46(6H, s), 3.53(2H, d, J=5.5 Hz), 5.33(1H, t, J=5.5 Hz), 8.63(1H, d, J=2.0 Hz), 8.81(1H, d, J=2.0 Hz), 8.82(1H, s).

MS m/z: 278(M$^+$–1).

PREPARATION 9

The following compound described in (1) to (6), (8) and (9) were obtained in a manner similar to Preparation 8.

(1) 2-[((R)-2-Hydroxy-1-methylethyl)amino]-3-nitro-5-(trifluoromethyl)pyridine

NMR(DMSO-d$_6$, δ): 1.24(3H, d, J=6.5 Hz), 3.56(2H, t, J=4.5 Hz), 4.39–4.51(1H, m), 5.07(1H, t, J=4.5 Hz), 8.60 (1H, d, J=8.0 Hz), 8.65(1H, d, J=2.0 Hz), 8.82(1H, d, J=2.0 Hz).

MS m/z: 264(M$^+$–1).

(2) 2-[(trans-4-Formamidocyclohexyl)amino]-3-nitro-5-(trifluoromethyl)pyridine mp. 225–226° C.

NMR(DMSO-d$_6$, δ): 1.24–1.40(2H, m), 1.51–1.68(2H, m), 1.79–2.02(4H, m), 3.55–3.70(1H, m), 4.12–4.27(1H, m), 7.95(1H, d, J=1.0 Hz), 8.00(1H, dd, J=7.5, 1.0 Hz), 8.40(1H, d, J=7.5 Hz), 8.63(1H, d, J=2.5 Hz), 8.82(1H, d, J=2.5 Hz).

MS m/z: 331(M$^+$–1).

(3) 5-Cyano-2-[((R)-2-hydroxy-1-methylethyl)amino]-3-nitropyridine mp. 114–115° C.

NMR(DMSO-d$_6$, δ): 1.23(3H, d, J=7.0 Hz), 3.54(2H, t, J=5.0 Hz), 4.38–4.51(1H, m), 5.07(1H, t, J=5.0 Hz), 8.69 (1H, d, J=7.5 Hz), 8.83(1H, d, J=2.0 Hz), 8.90(1H, d, J=2.0 Hz).

MS m/z : 221(M$^+$–1).

(4) 2-(trans-4-hydroxycyclohexylamino)-3-nitro-5-methoxycarbonylpyridine mp. 117–118° C.

NMR(DMSO-d$_6$, δ): 1.20–1.37(2H, m), 1.45–1.61(2H, m), 1.79–1.98(4H, m), 3.39–3.52(1H, m), 3.85(3H, s), 4.11–4.25(1H, m), 4.62(1H, d, J=4.0 Hz), 8.45(1H, d, J=8.0 Hz), 8.73(1H, d, J=2.0 Hz), 8.92(1H, d, J=2.0 Hz).

MS m/z: 294(M$^+$–1)

(5) 5-Cyano-2-(trans-4-hydroxycyclohexylamino)-3-nitropyridine mp. 157–158° C.

NMR(DMSO-d$_6$, δ): 1.20–1.35(2H, m), 1.45–1.61(2H, m), 1.80–1.95(4H, m), 3.39–3.50(1H, m), 4.08–4.23(1H, m), 4.63(1H, d, J=4.0 Hz), 8.47(1H, d, J=8.0 Hz), 8.83(1H, d, J=2.0 Hz), 8.88(1H, d, J=2.0 Hz).

MS m/z: 261 (M$^+$–1).

(6) 2-((R)-1-tert-Butoxycarbonylpyrrolidin-3-ylamino)-3-nitro-5-(trifluoromethyl)pyridine NMR(DMSO-d$_6$, δ): 1.38(9H, s), 2.00–2.12(1H, m), 2.16–2.29(1H, m), 3.24–3.49(3H, m), 3.60–3.69(1H, m), 4.71–4.86(1H, m), 8.50(1H, d, J=4.5 Hz), 8.64(1H, s), 8.86(1H, s).

MS m/z: 375(M$^+$–1).

(7) To a solution of 2-chloro-5-cyano-3-nitropyridine (3.5 g)(obtained according to International Patent Application No.WO9410171) in N,N-dimethylformamide (35 mL) was added trans-4-aminocyclohexanol (4.39 g) at 0° C. The mixture was stirred at room temperature under nitrogen atmosphere for 45 minutes and diluted with ethyl acetate.

The mixture was washed with water (3 times) and brine, dried over anhydrous magnesium sulfate, and concentrated in vacuo. The residual solid was washed with diethyl ether to give 5-cyano-2-(trans-4-hydroxycyclohexylamino)-3-nitropyridine (3.38 g) as a yellow sold.

mp. 157–158° C.

NMR(DMSO-$d_6$, δ): 1.20–1.35 (2H, m), 1.45–1.61 (2H, m), 1.80–1.95 (4H, m), 3.39–3.50 (1H, m), 4.08–4.23 (1H, m), 4.63 (1H, d, J=4.0 Hz), 8.47 (1H, d, J=8.0 Hz), 8.83 (1H, d, J=2.0 Hz), 8.88 (1H, d, J=2.0 Hz).

MS m/z: 261($M^+$–1).

(8) 6-(Benzimidazol-5-yl)amino-5-nitronicotinonitrile

NMR(DMSO-$d_6$, δ): 7.64(1H, dd, J=8, 1 Hz), 8.83(1H, d, J=8Hz), 8.09(1H, d, J=1 Hz), 8.83(1H, d, J=1 Hz), 9.05(1H, d, J=1 Hz), 9.40(1H, s).

(9) 6-(1H-Indol-5-ylamino)-5-nitronicotinonitrile mp. 198–198.5° C.

NMR(DMSO-$d_6$, δ): 6.42–6.46(1H, m), 7.17(1H, d, J=8.5 Hz), 7.37–7.34(1H, m), 7.40(1H, d, J=8.5 Hz), 7.68–7.71 (1H, m), 8.76(1H, s), 8.98(1H, s), 10.40(1H, s), 11.19(1H, brs).

MS m/z: 278($M^+$–1).

PREPARATION 10

To a solution of 5-cyano-2-hydroxy-3-nitropyridine (600 mg) in 6 mL of dichloromethane containing triethylamine (0.557 mL) was added methanesulfonyl chloride (0.295 mL) under stirring at 0° C. The reaction mixture was stirred at the same temperature for 30 minutes, and then trans-4-aminocyclohexanol (1.26 g) was added to the mixture at 0° C. After stirring at room temperature for 2 hours, the mixture was washed with water and brine, dried over magnesium sulfate and evaporated in vacuo. The residue was subjected to a preparative silica gel column chromatography eluting with 5% methanol in chloroform. The obtained substance was triturated with diisopropyl ether to give 5-cyano-2-(trans-4-hydroxycyclohexylamino)-3-nitropyridine (198.9 mg) as a yellow solid.

mp. 147–147.5° C.

NMR(DMSO-$d_6$, δ): 1.19–1.36(2H, m), 1.44–1.61(2H, m), 1.79–1.96(4H, m), 3.38–3.51(1H, m), 4.08–4.22(1H, m), 4.62(1H, d, J=4.0 Hz), 8.47(1H, d, J=7.5 Hz), 8.83(1H, d, J=2.5 Hz), 8.88(1H, d, J=2.5 Hz).

MS m/z: 261($M^+$–1).

PREPARATION 11

To a solution of 4-fluoro-3-nitrobenzotrifluoride (900 mg) in pyridine (9 mL) was added trans-4-formamidocyclohexylamine (734 mg). The mixture was stirred at 100° C. under nitrogen atmosphere for 5 hours. After cooling to room temperature, water was added to the mixture. The resulting precipitate was collected by filtration and washed with water to give 4-[(trans-4-formamidocyclohexyl)amino]-3-nitrobenzotrifluoride (1.24 g) as a yellow solid.

mp. 174–175° C.

NMR(DMSO-$d_6$, δ): 1.32–1.58(4H, m), 1.78–1.90(2H, m), 1.95–2.06(2H, m), 3.56–3.77(2H, m), 7.37(1H, d, J=9.5 Hz), 7.77(1H, dd, J=9.5, 2.5 Hz), 7.96(1H, s), 8.06(1H, d, J=7.5 Hz), 8.14(1H, d, J=7.5 Hz), 8.32(1H, d, J=2.5 Hz).

MS m/z: 330($M^+$–1).

PREPARATION 12

The following compounds described in (1) to (22) were obtained in a manner similar to Preparation 11.

(1) 3-Amino-4-cyclopentylamino-1-nitrobenzene mp. 137–138° C.

NMR(DMSO-$d_6$, δ): 1.47–1.77(6H, m), 1.94–2.07(2H, m), 3.80–3.93(1H, m), 5.23(2H, s), 5.73(1H, d, J=6.5 Hz), 6.49(1H, d, J=8.5 Hz), 7.38(1H, d, J=3.0 Hz), 7.51(1H, dd, J=8.5, 3.0 Hz).

MS m/z: 220($M^+$–1)

(2) 3-Amino-4-(trans-4-hydroxycyclohexylamino)-1-nitrobenzene mp. 156–157° C.

NMR(DMSO-$d_6$, δ): 1.19–1.40(4H, m), 1.81–2.00(4H, m), 3.29–3.48(2H, m), 4.60(1H, d, J=4.0 Hz), 5.18(2H, s), 5.59(1H, d, J=7.5 Hz), 6.52(1H, d, J=9.0 Hz), 7.38(1H, d, J=2.5 Hz), 7.50(1H, dd, J=9.0, 2.5 Hz).

MS m/z: 250($M^+$–1).

(3) 5-Chloro-2-(trans-4-hydroxycyclohexylamino)-1-nitrobenzene mp. 124.5–126° C.

NMR(DMSO-$d_6$, δ): 1.26–1.46(4H, m), 1.76–1.87(2H, m), 1.93–2.03(2H, m), 3.41–3.51(1H, m), 3.54–3.66(1H, m), 4.63(1H, d, J=4.0 Hz), 7.20(1H, d, J=9.5 Hz), 7.55(1H, dd, J=9.5, 2.5 Hz), 7.90(1H, d, J=8.0 Hz), 8.05(1H, d, J=2.5 Hz).

(4) Methyl 4-(trans-4-hydroxycyclohexylamino)-3-nitrobenzoate mp. 177–179° C.

NMR(DMSO-$d_6$, δ): 1.27–1.54(4H, m), 1.78–1.90(2H, m), 1.94–2.05(2H, m), 3.41–3.55(1H, m), 3.60–3.74(1H, m), 3.83(3H, s), 4.65(1H, d, J=4.0 Hz), 7.24(1H, d, J=9.0 Hz), 7.96(1H, dd, J=9.0, 2.0 Hz), 8.22(1H, d, J=7.5 Hz), 8.62(1H, d, J=2.0 Hz).

(5) 4-(trans-4-Hydroxycyclohexylamino)-3-nitroanisole mp. 142–142.5° C.

NMR(DMSO-$d_6$, δ): 1.26–1.45(4H, m), 1.74–2.07(4H, m), 3.39–3.64(2H, m), 3.74(3H, s), 4.62(1H, d, J=4.0 Hz), 7.14(1H d, J=9.5 Hz), 7.26(1H, dd, J=9.5, 2.5 Hz), 7.47(1H, d, J=2.5 Hz), 7.88(1H, d, J=7.5 Hz).

(6) 2-(trans-4-Hydroxycyclohexylamino)-3-nitro-5-(trifluoromethyl)pyridine mp. 125–125.5° C.

NMR(DMSO-$d_6$, δ): 1.20–1.36(2H, m), 1.45–1.61(2H, m), 1.80–1.98(4H, m), 3.39–3.52(1H, m), 4.08–4.24(1H, m), 4.63(1H, d, J=4.0 Hz), 8.37(1H, d, J=7.5 Hz), 8.63(1H, d, J=1.0 Hz), 8.83(1H, d, J=1.0 Hz).

MS m/z: 304($M^+$–1).

(7) 2-Cyclopentylamino-3-nitro-5-(trifluoromethyl)pyridine

NMR(DMSO-$d_6$, δ): 1.50–1.78(6H, m), 1.97–2.09(2H, m), 4.52–4.64(1H, m), 8.46(1H, d, J=7.0 Hz), 8.63(1H, d, J=1.0 Hz), 8.83(1H, d, J=1.0 Hz).

MS m/z: 274($M^+$–1)

(8) 4-(trans-2-Hydroxycyclopentylamino)-3-nitrobenzotrifluoride mp. 92–92.5° C.

NMR(DMSO-$d_6$, δ): 1.49–1.96(5H, m), 2.16–2.30(1H, m), 3.77–3.88(1H, m), 3.95–4.06(1H, m), 5.17(1H, d, J=4.5 Hz), 7.39(1H, d, J=9.5 Hz), 7.82(1H, d, J=9.5 Hz), 8.20(1H, d, J=7.5 Hz), 8.32(1H, s).

MS m/z: 289($M^+$–1).

(9) 4-[(S)-1-tert-Butoxycarbonylpyrrolidin-3-ylamino]-3-nitrobenzotrifluoride mp. 95.5–97° C.

NMR(DMSO-$d_6$, δ): 1.40(9H, s), 1.93–2.07(1H, m), 2.20–2.33(1H, m), 3.23–3.47(3H, m), 3.65–3.74(1H, m), 4.36–4.48(1H, m), 7.36(1H, d, J=9.5 Hz), 7.84(1H, dd, J=9.5, 2.0 Hz), 8.18(1H, d, J=7.0 Hz), 8.33(1H, d, J=2.0 Hz).

MS m/z: 374($M^+$–1).

(10) 4-(1H-Benzimidazol-5-ylamino)-3-nitrobenzotrifluoride
mp. 229–230.5° C.
NMR(DMSO-d$_6$, δ): 7.07(1H, brs), 7.19(1H, d, J=8.0 Hz), 7.55(1H, brs), 7.65(1H, brs), 7.71(1H, dd, J=8.0, 2.0 Hz), 8.30(1H, s), 8.38(1H, d, J=2.0 Hz), 9.92(1H, s), 12.60 (1H, s).
MS m/z: 323(M$^+$–1).
(11) 4-(trans-4-Hydroxycyclohexylamino)-3-nitrotoluene
NMR(DMSO-d$_6$, δ): 1.25–1.43(4H, m), 1.76–1.89(2H, m), 1.92–2.05(2H, m), 2.22(3H, s), 3.39–3.63(2H, m), 4.63 (1H, d, J=4.0 Hz), 7.06(1H, d, J=9.0 Hz), 7.38(1H, dd, J=9.0, 2.5 Hz), 7.83(1H, d, J=7.5 Hz), 7.86(1H, d, J=2.5 Hz).
(12) 4-[1-(Hydroxymethyl)cyclopentylamino]-3-nitrobenzotrifluoride
NMR(DMSO-d$_6$, δ): 1.57–2.01(8H, m), 3.56(2H, d, J=5.5 Hz), 5.18(1H, t, J=5.5 Hz), 7.24(1H, d, J=9.5 Hz), 7.76(1H, dd, J=9.5, 2.5 Hz), 8.34(1H, d, J=2.5 Hz), 8.61(1H, s).
MS m/z: 303(M$^+$–1).
(13) 4-[((R)-2-Hydroxy-2-methylethyl)amino-3-nitrobenzotrifluoride
mp. 96–97° C.
NMR(DMSO-d$_6$, δ): 1.23(3H, d, J=6.5 Hz), 3.47–3.64 (2H, m), 3.90–4.01(1H, m), 5.14(1H, t, J=5.0 Hz), 7.31(1H, d, J=9.5 Hz), 7.79(1H, dd, J=9.5, 2.0 Hz), 8.32(1H, d, J=2.0 Hz), 8.43(1H, d, J=7.5 Hz).
MS m/z: 263(M$^+$–1).
(14) 4-(tert-Butylamino)-3-nitrobenzotrifluoride
mp. 167–168° C.
NMR(DMSO-d$_6$, δ): 1.49(9H, s), 7.47(1H, d, J=9.5 Hz), 7.74(1H, dd, J=9.5, 2.5 Hz), 8.34(1H, d, J=2.5 Hz), 8.45(1H, s).
MS m/z: 261(M$^+$–1).
15) 4-(2-Hydroxyethylamino)-3-nitrobenzotrifluoride
mp. 76–77° C.
NMR(DMSO-d$_6$, δ): 3.49(2H, q, J=5.5 Hz), 3.66(2H, q, J=5.5 Hz), 5.03(1H, t, J=5.5 Hz), 7.28(1H, d, J=9.5 Hz), 7.80(1H, dd, J=9.5, 2.5 Hz), 8.32(1H, d, J=2.5 Hz), 8.56(1H, t, J=5.5 Hz).
MS m/z: 249(M$^+$–1).
(16) 3-Nitro-4-(tetrahydro-4H-pyran-4-ylamino) benzotrifluoride
mp. 113–114° C.
NMR(DMSO-d$_6$, δ): 1.55–1.70(2H, m), 1.89–1.99(2H, m), 3.42–3.54(2H, m), 3.83–3.92(2H, m), 3.91–4.03(4H, m), 7.39(1H, d, J=9.0 Hz), 7.78(1H dd, J=9.0, 2.5 Hz), 8.17(1H, d, J=7.5 Hz), 8.33(1H, d, J=2.5 Hz).
MS m/z: 289(M$^+$–1).
(17) 4-Isopropylamino-3-nitrobenzotrifluoride
mp. 107–108° C.
NMR(DMSO-d$_6$, δ): 1.29(6H, d, J=6.5 Hz), 4.02(1H, m), 7.28(1H, d, J=9.5 Hz), 7.80(1H, dd, J=9.5, 2.5 Hz), 8.13(1H, d, J=6.5 Hz), 8.32(1H, d, J=2.5 Hz).
(18) 4-Butylamino-3-nitrobenzotrifluoride
NMR(DMSO-d$_6$, δ): 0.93(3H, t, J=7.0 Hz), 1.31–1.45 (2H, m), 1.55–1.66(2H, m), 3.37–3.46(2H, m), 7.24(1H, d, J=9.0 Hz), 7.78(1H, dd, J=9.0, 2.5 Hz), 8.31(1H, d, J=2.5 Hz), 8.49(1H, t, J=5.5 Hz).
MS m/z: 261(M$^+$–1)
(19) 4-Cyclohexylamino-3-nitrobenzotrifluoride
mp. 82–83° C.
NMR(DMSO-d$_6$, δ): 1.17–1.50(5H, m), 1.54–1.76(3H, m), 1.89–2.00(2H, m), 3.66–3.78(1H, m), 7.32(1H, d, J=9.0 Hz), 7.77(1H, dd, J=9.0, 2.5 Hz), 8.22(1H, d, J=7.5 Hz), 8.32(1H, d, J=2.5 Hz).
(20) 4-[(trans-4-Aminocyclohexyl)amino]-3-nitrobenzotrifluoride
NMR(DMSO-d$_6$, δ): 1.11–1.29 (2H, m), 1.35–1.51 (2H, m), 1.72–1.85 (2H, m), 1.90–2.03 (2H, m), 2.53–2.65 (1H, m), 3.56–3.72 (1H, m), 7.26 (1H, d, J=8 Hz), 7.81 (1H, dd, J=8, 2 Hz), 8.20 (1H, d, J=8 Hz), 8.51 (1H, d, J=2 Hz).
(21) 4-[(trans-4-Aminocyclohexyl)amino]-3-nitrobenzotrifluoride
mp. 86–87° C.
NMR(DMSO-d$_6$, δ): 1.12–1.29(2H, m), 1.34–1.50(2H, m), 1.74–1.85(2H, m), 1.93–2.04(2H, m), 2.54–2.65(1H, m), 3.56–3.70(1H, m), 7.32(1H, d, J=9.0 Hz), 7.76(1H, dd, J=9.0, 2.5 Hz), 8.13(1H, d, J=8.0 Hz), 8.30(1H, d, J=2.5 Hz).
MS m/z: 302(M$^+$–1).
(22) 4-(Benzimidazol-5-ylamino)-3-nitrobenzonitrile
NMR(DMSO-d$_6$, δ): 3.17 (1H, s), 6.96 (1H, d, J=8 Hz), 7.16 (1H, dd, J=8,2 Hz), 7.57 (1H, s), 7.66–7.74 (2H, m), 8.30 (1H, s), 8.59 (1H, d, J=2 Hz).

PREPARATION 13

To a solution of 4-(trans-4-hydroxycyclohexylamino)-3-nitrobenzonitrile (1.0 g), acetic acid (345 mg) and diethyl azodicarboxylate (2.17 g, 40% solution in toluene) in anhydrous tetrahydrofuran (25 mL) was added portionwise triphenylphosphine (1.31 g) at 0° C., and the mixture was stirred at ambient temperature for 2 hours. The mixture was evaporated in vacuo and the residue was subjected to a silica gel column chromatography eluting with a mixture of n-hexane and ethyl acetate (5:1 to 3:1) and then chloroform. The obtained substance was triturated with methanol to give 4-(cis-4-acetoxycyclohexylamino)-3-nitrobenzonitrile (530 mg) as yellow powders.
NMR(CDCl$_3$, δ) 1.66–1.86 (4H, m); 1.86–2.01 (4H, m), 2.10 (3H, s), 3.66 (1H, br), 5.00 (1H, br), 6.93 (1H, d, J=8 Hz), 7.60 (1H, dd, J=8, 2 Hz), 8.50 (1H, br), 8.53 (1H, d, J=2 Hz).

PREPARATION 14

A mixture of 4-(trans-4-hydroxycyclohexylamino)-3-nitrobenzotrifluoride (4.0 g) and 10% palladium on activated carbon (400 mg) in a mixture of methanol (20 mL) and dioxane(20 mL) was stirred under hydrogen atmosphere (3 atm) at ambient temperature for 4 hours. The reaction mixture was filtered through a celite pad, and the filtrate was concentrated in vacuo. The residue was subjected to a silica gel column chromatography eluting with a mixture of chloroform and methanol (20:1). The obtained substance was triturated with petroleum ether to give 3-amino-4-(trans-4-hydroxycyclohexylamino)benzotrifluoride (3.5 g) as a pale orange solid.
mp. 112–113.5° C.
NMR(CDCl$_3$, δ): 1.19–1.55(5H, m), 1.99–2.22(4H, m), 3.21–3.39(3H, m), 3.56(1H, brs), 3.64–3.77(1H, m), 6.64 (1H, d, J=8.5 Hz), 6.94(1H, d, J=2.0 Hz), 7.08(1H, dd, J=8.5, 2.0 Hz).
MS m/z: 275(M$^+$–1).

PREPARATION 15

The following compounds described in (1) to (56) and (58) to (62) were obtained in a manner similar to Preparation 14.
(1) 3-Amino-4-(trans-4-hydroxycyclohexylamino) benzonitrile
mp. 116–117° C.
NMR(DMSO-d$_6$, δ): 1.14–1.40(4H, m), 1.78–2.03(4H, m), 3.18–3.30(1H, m), 3.38–3.49(1H, m), 4.58(1H, d, J=4.0 Hz), 4.98(2H, s), 5.05(1H, d, J=7.0 Hz), 6.49(1H, d, J=8.5 Hz), 6.75(1H, d, J=1.5 Hz), 6.90(1H, dd, J=8.5, 1.5 Hz).

(2) 3-Amino-4-[((R)-2-hydroxy-1-methylethyl)amino]benzotrifluoride
mp. 113–114.5° C.
NMR(DMSO-$d_6$, δ): 1.15(3H, d, J=6.5 Hz), 3.25–3.56 (3H, m), 4.66–4.79(2H, m), 4.93(2H, s), 6.52(1H, d, J=9.0 Hz), 6.79(1H, d, J=9.0 Hz), 6.80(1H, s).
MS m/z: 233($M^+$−1).

(3) 3-Amino-4-(trans-4-hydroxycyclohexylamino)acetophenone
mp. 177–178° C.
NMR(DMSO-$d_6$, δ): 1.15–1.38(4H, m), 1.80–2.00(4H, m), 2.35(3H, s), 3.21–3.34(1H, m), 3.38–3.48(1H, m), 4.58 (1H, d, J=4.5 Hz), 4.74(2H, s), 4.99(1H, d, J=7.5 Hz), 6.45(1H, d, J=8.5 Hz), 7.13(1H, d, J=2.0 Hz), 7.21(1H, dd, J=8.5, 2.0 Hz).
MS m/z: 249($M^+$+1).

(4) 3-Amino-4-[(trans-4-formamidocyclohexyl)amino]benzotrifluoride
NMR(DMSO-$d_6$, δ): 1.17–1.47(4H, m), 1.79–1.90(2H, m), 1.96–2.07(2H, m), 3.17–3.34(1H, m), 3.54–3.68(1H, m), 4.77(1H, d, J=8.0 Hz), 4.94(2H, s), 6.53(1H, d, J=8.5 Hz), 6.77(1H, d, J=8.5 Hz), 6.78(1H, s), 7.95(1H, s), 8.03 (1H, d, J=7.5 Hz).
MS m/z: 302($M^+$+1).

(5) 1-Amino-5-chloro-2-(trans-4-hydroxycyclohexylamino)benzene
mp. 150–151° C.
NMR(DMSO-$d_6$, δ): 1.07–1.35(4H, m), 1.76–2.03(4H, m), 3.02–3.19(1H, m), 3.30–3.49(1H, m), 4.19(1H, d, J=7.5 Hz), 4.55(1H, d, J=4.0 Hz), 4.82(2H, s), 6.38(1H, d, J=8.5 Hz), 6.44(1H, dd, J=8.5, 2.5 Hz), 6.52(1H, d, J=2.5 Hz).

(6) Methyl 3-amino-4-(trans-4-hydroxycyclohexylamino)benzoate
mp. 172–172.5° C.
NMR(DMSO-$d_6$, δ): 1.15–1.39(4H, m), 1.80–2.00(4H, m), 3.19–3.30(1H, m), 3.38–3.49(1H, m), 3.71(3H, s), 4.58 (1H, d, J=4.0 Hz), 4.75(2H, s), 4.89(1H, d, J=7.5 Hz), 6.46(1H, d, J=8.5 Hz), 7.15(1H, d, J=2.5 Hz), 7.18(1H, dd, J=8.5, 2.5 Hz).
MS m/z: 265($M^+$+1)

(7) 3-Amino-4-(trans-4-hydroxycyclohexylamino)anisole
NMR(DMSO-$d_6$, δ): 1.04–1.30(4H, m), 1.75–1.97(4H, m), 2.89–3.04(1H, m), 3.32–3.46(1H, m), 3.53–3.64(1H, m), 3.58(3H, s), 4.52(1H, d, J=4.0 Hz), 4.58(2H, s), 6.04 (1H, dd, J=8.5, 2.5 Hz), 6.19(1H, d, J=2.5 Hz), 6.37(1H, d, J=8.5 Hz).

(8) 2-(trans-4-Acetoxycyclohexylamino)-3-amino-5-(trifluoromethyl)pyridine
mp. 162.5–164° C.
NMR(DMSO-$d_6$, δ): 1.26–1.54(4H, m), 1.87–2.08(4H, m), 2.00(3H, s), 3.84–3.99(1H, m), 4.56–4.69(1H, m), 5.20 (2H, s), 6.00(1H, d, J=7.0 Hz), 6.82(1H, d, J=1.5 Hz), 7.67(1H, d, J=1.5 Hz).
MS m/z: 318(M++1).

(9) 3-Amino-2-cyclopentylamino-5-(trifluoromethyl)pyridine
NMR(DMSO-$d_6$, δ): 1.39–1.77(6H, m), 1.87–2.04(2H, m), 4.24–4.37(1H, m), 5.20(2H, s), 6.07(1H, d, J=7.0 Hz), 6.80(1H, d, J=2.0 Hz), 7.66(1H, d, J=2.0 Hz).
MS m/z: 246($M^+$+1).

(10) 3-Amino-4-(trans-2-acetoxycyclopentylamino)benzotrifluoride
NMR(DMSO-$d_6$, δ): 1.50–1.85(4H, m), 1.91–2.23(2H, m), 2.03(3H, s), 3.70–3.82(1H, m), 4.87–4.95(1H, m), 4.97 (1H, d, J=6.0 Hz), 5.01(2H, s), 6.60(1H, d, J=8.5 Hz), 6.78(1H, d, J=8.5 Hz), 6.80(1H, s).
MS m/z: 303($M^+$+1).

(11) 3-Amino-4-[(S)-1-tert-butoxycarbonylpyrrolidin-3-ylamino]benzotrifluoride
NMR(DMSO-$d_6$, δ): 1.40(9H, s), 1.77–1.91(1H, m), 2.08–2.21(1H, m), 3.09–3.23(1H, m), 3.30–3.45(2H, m), 3.55–3.63(1H, m), 3.97–4.10(1H, m), 5.03(2H, s), 5.09(1H, d, J=6.0 Hz), 6.53(1H, d, J=8.5 Hz), 6.78(1H, d, J=8.5 Hz), 6.79(1H, s).
MS m/z: 346($M^+$+1).

(12) 3-Amino-4-(1H-benzimidazol-5-ylamino)benzotrifluoride
NMR(DMSO-$d_6$, δ): 5.19(2H, s), 6.78(1H, dd, J=8.5, 2.0 Hz), 6.92(1H, d, J=8.5 Hz), 6.98(1H, d, J=2.0 Hz), 7.00–7.28(3H, m), 7.49(1H, d, J=8.5 Hz), 8.07(1H, brs).
MS m/z: 291($M^+$+1).

(13) 2-(2-Acetoxy-1,1-dimethylethylamino)-3-amino-5-(trifluoromethyl)pyridine
NMR(DMSO-$d_6$, δ): 1.41(6H, s), 2.01(3H, s), 4.39(2H, s), 5.30(2H, s), 5.55(1H, s), 6.85(1H, d, J=2.0 Hz), 7.65(1H, d, J=2.0 Hz).
MS m/z: 292($M^+$+1).

(14) 4-(trans-4-Acetoxycyclohexylamino)-3-aminotoluene
mp. 119–120° C.
NMR(DMSO-$d_6$, δ): 1.16–1.32(2H, m), 1.37–1.52(2H, m), 1.86–2.04(4H, m), 1.99(3H, s), 2.07(3H, s), 3.08–3.21 (1H, m), 3.90(1H, d, J=8.0 Hz), 4.42(2H, s), 4.55–4.67(1H, m), 6.27(1H, dd, J=8.0, 2.5 Hz), 6.32(1H, d, J=2.5 Hz), 6.36(1d, J=8.0 Hz).
MS m/z: 263($M^+$+1).

(15) 4-[1-(Acetoxymethyl)cyclopentylamino]-3-aminobenzotrifluoride
NMR(DMSO-$d_6$, δ): 1.55–1.75(4H, m), 1.77–2.00(4H, m), 2.00(3H, s), 4.20(2H, s), 4.60(1H, s), 5.04(2H, s), 6.61(1H, d, J=8.0 Hz), 6.75(1H, dd, J=8.0, 2.5 Hz), 6.80(1H, d, J=2.5 Hz).
MS m/z: 315($M^+$−1).

(16) 2-[((R)-2-Acetoxy-1-methylethyl)amino]-3-amino-5-(trifluoromethyl)pyridine
NMR(DMSO-$d_6$, δ): 1.20(3H, d, J=6.5 Hz), 2.00(3H, s), 4.05(2H, d, J=5.5 Hz), 4.34–4.46(1H, m), 5.22(2H, s), 6.11(1H, d, J=7.0 Hz), 6.85(1H, d, J=2.0 Hz), 7.67(1H, d, J=2.0 Hz).
MS m/z: 278($M^+$+1).

(17) 1-(trans-4-Acetoxycyclohexylamino)-2-amino-4-(methylsulfonyl)benzene
mp. 230–231° C.
NMR(DMSO-$d_6$, δ): 1.25–1.59(4H, m), 1.89–2.07(4H, m), 2.00(3H, s), 2.98(3H, s), 3.25–3.44(1H, m), 4.56–4.69 (1H, m), 5.02(1H, d, J=7.5 Hz), 5.04(2H, s), 6.58(1H, d, J=8.5 Hz), 6.99(1H, d, J=2.5 Hz), 7.00(1H, dd, J=8.5, 2.5 Hz).
MS m/z: 325($M^+$−1).

(18) 4-((R)-2-Acetoxy-1-methylethyl)amino]-3-aminobenzotrifluoride
NMR(DMSO-$d_6$, δ): 1.19(3H, d, J=6.5 Hz), 2.02(3H, s), 3.72–3.83(1H, m), 3.91(1H, dd, J=10.0, 7.0 Hz), 4.10(1H, dd, J=10.0, 5.5 Hz), 4.85(1H, d, J=7.5 Hz), 4.97(2H, s), 6.58(1H, d, J=8.0 Hz), 6.78(1H, d, J=8.0 Hz), 6.80(1H, s).
MS m/z: 277($M^+$+1).

(19) 2-(trans-4-Acetoxycyclohexylamino)-3-amino-5-cyanopyridine
mp. 237.5–238° C.
NMR(DMSO-$d_6$, δ): 1.27–1.54(4H, m), 1.88–2.05(4H, m), 2.00(3H, s), 3.85–3.99(1H, m), 4.56–4.68(1H, m), 5.23 (2H, s), 6.27(1H, d, J=7.0 Hz), 6.79(1H, d, J=2.0 Hz), 7.79(1H, d, J=2.0 Hz).
MS m/z: 275($M^+$+1).

(20) 4-(trans-4-Acetoxycyclohexylamino)-3-aminobenzophenone
mp. 215–215.5° C.

NMR(DMSO-d$_6$, δ): 1.27–1.58(4H, m), 1.90–2.08(4H, m), 2.00(3H, s), 3.34–3.46(1H, m), 4.57–4.69(1H, m), 4.85 (2H, s), 5.15(1H, d, J=7.5 Hz), 6.53(1H, d, J=8.5 Hz), 6.97(1H, dd, J=8.5, 2.0 Hz), 7.09(1H, d, J=2.0 Hz), 7.45–7.61(5H, m).
MS m/z: 353(M$^+$+1).

(21) 3-Amino-4-(tertbutylamino)benzotrifluoride
NMR(DMSO-d$_6$, δ): 1.34(9H, s), 4.31(1H, s), 4.96(2H, s), 6.77(2H, s), 6.83(1H, s).
MS m/z: 233(M$^+$+1).

(22) 4-(2-Acetoxyethylamino)-3-aminobenzotrifluoride
NMR(DMSO-d$_6$, δ): 2.03(3H, s), 3.37(2H, q, J=5.5 Hz), 4.18(2H, t, J=5.5 Hz), 4.95(2H, s), 5.20(1H, t, J=5.5 Hz), 6.55(1H, d, J=8.5 Hz), 6.80(1H, d, J=8.5 Hz), 6.81(1H, s).
MS m/z: 263(M$^+$+1).

(23) 3-Amino-4-(tetrahydro-4H-pyran-4-ylamino)benzotrifluoride
NMR(DMSO-d$_6$, δ): 1.35–1.50(2H, m), 1.86–1.95(2H, m), 3.37–3.46(2H, m), 3.49–3.59(1H, m), 3.84–3.93(2H, m), 4.83(1H, d, J=7.5 Hz), 4.97(2H, s), 6.57(1H, d, J=9.5 Hz), 6.77(1H, d, J=9.5 Hz), 6.79(1H, s).
MS m/z: 261(M$^+$+1).

(24) 3-Amino-4-(isopropylamino)benzotrifluoride
NMR(DMSO-d$_6$, δ): 1.17(6H, d, J=6.5 Hz), 3.62(1H, m), 4.74(1H, d, J=7.5 Hz), 4.94(2H, s), 6.48(1H, d, J=8.5 Hz), 6.79(1H, s), 6.79(1H, d, J=8.5 Hz).
MS m/z: 219(M$^+$+1).

(25) 3-Amino-4-(butylamino)benzotrifluoride
NMR(DMSO-d$_6$, δ): 0.92(3H, t, J=7.5 Hz), 1.33–1.46 (2H, m), 1.53–1.64(2H, m), 3.02–3.11(2H, m), 4.93(2H, s), 4.98(1H, t, J=5.5 Hz), 6.45(1H, d, J=9.0 Hz), 6.77(1H, s), 6.79(1H, d, J=9.0 Hz).
MS m/z: 233(M$^+$+1).

(26) 3-Amino-4-(cyclohexylamino)benzotrifluoride
mp. 73.5–75° C.
NMR(DMSO-d$_6$, δ): 1.10–1.44(5H, m), 1.56–1.79(3H, m), 1.90–2.02(2H, m), 3.18–3.35(1H, m), 4.73(1H, d, J=7.5 Hz), 4.94(2H, s), 6.49(1H, d, J=9.0 Hz), 6.77(1H, d, J=9.0 Hz), 6.78(1H, s).
MS m/z: 259(M$^+$+1)

(27) 2-[(trans-4-Formamidocyclohexyl)amino]-3-amino-5-(trifluoromethyl)pyridine
mp. 262.5–263° C.
NMR(DMSO-d$_6$, δ): 1.21–1.39(4H, m), 1.75–1.88(2H, m), 1.94–2.05(2H, m), 3.55–3.67(1H, m), 3.79–3.94(1H, m), 5.19(2H, s), 6.00(1H, d, J=7.5 Hz), 6.81(1H, d, J=2.5 Hz), 7.66(1H, s), 7.95(1H, s), 7.99(1H, m).
MS m/z: 303(M$^+$+1).

(28) 3-Amino-4-[((R)-2-hydroxy-1-methylethyl)amino]benzonitrile
NMR(DMSO-d$_6$, δ): 1.16 (3H, d, J=7.5 Hz), 3.23–3.40 (1H, m), 3.40–3.60 (2H, m), 4.76 (1H, t, J=5 Hz), 4.97 (2H, s), 5.03 (1H, d, J=7.5 Hz), 6.50 (1H, d, J=8 Hz), 6.77 (1H, d, J=2 Hz), 6.91 (1H, dd, J=8, 2 Hz).

(29) 3-Amino-4-[((S)-2-hydroxy-1-methylethyl)amino]benzonitrile
NMR(DMSO-d$_6$, δ): 1.15 (3H, d, J=7.5 Hz), 3.25–3.40 (1H, m), 3.40–3.60 (2H, m), 4.76 (1H, t, J=5 Hz), 4.97 (2H, s), 5.02 (1H, d, J=7.5 Hz), 6.50 (1H, d, J=8 Hz), 6.77 (1H, d, J=2 Hz), 6.91 (1H, dd, J=8, 2 Hz).

(30) 3-Amino-4-[(trans-4-formamidocyclohexyl)amino]benzonitrile
NMR(DMSO-d$_6$, δ): 1.18–1.44 (4H, m), 1.74–1.91 (2H, m), 1.91–2.08 (2H, m), 3.14–3.35 (1H, m), 3.50–3.70 (1H, m), 4.98 (2H, s), 5.10 (1H, d, J=8 Hz), 6.52 (1H, d, J=8 Hz), 6.76 (1H, d, J=2 Hz), 6.89 (1H, dd, J=8, 2 Hz), 7.94 (1H, s), 8.04 (1H, d, J=8 Hz).

(31) 3-Amino-4-[(2,2-dimethyl-1,3-dioxan-5-yl)amino]benzonitrile
NMR(DMSO-d$_6$, δ): 1.36 (3H, s), 1.40 (3H, s), 3.56–3.72 (3H, m), 3.90–4.00 (2H, m), 5.01 (2H, s), 5.18 (1H, d, J=8 Hz), 6.58 (1H, d, J=8 Hz), 6.81 (1H, d, J=2 Hz), 6.90 (1H, dd, J=8, 2 Hz).

(32) 4-(2-Acetoxy-1,1-dimethylethylamino)-3-aminobenzonitrile
NMR(DMSO-d$_6$, δ): 1.34 (6H, s), 2.03 (3H, s), 4.10 (2H, s), 4.62 (1H, s), 5.05 (2H, s), 6.78 (1H, d, J=8 Hz), 6.83 (1H, d, J=2 Hz), 6.90 (1H, dd, J=8, 2 Hz).

(33) 4-[((R)-2-Acetoxy-1-methylethyl)amino]-3-aminobenzonitrile
NMR(DMSO-d$_6$, δ): 1.18 (3H, d, J=7 Hz), 2.01 (3H, s), 3.76–3.97 (2H, m), 4.04–4.13 (1H, m), 5.01 (2H, s), 5.17 (1H, d, J=8 Hz), 6.58 (1H, d, J=8 Hz), 6.78 (1H, d, J=2 Hz), 6.91 (1H, dd, J=8, 2 Hz).

(34) 4-[((S)-2-Acetoxy-1-methylethyl)amino]-3-aminobenzonitrile
NMR(DMSO-d$_6$, δ): 1.19 (3H, d, J=7 Hz), 2.01 (3H, s), 3.75–3.97 (2H, m), 4.05–4.13 (1H, m), 5.01 (2H, s), 5.17 (1H, d, J=8 Hz), 6.58 (1H, d, J=8 Hz), 6.78 (1H, d, J=2 Hz), 6.91 (1H, dd, J=8, 2 Hz).

(35) 4-(2-Acetoxy-1,1-dimethylethylamino)-3-aminobenzotrifluoride
NMR(DMSO-d$_6$, δ): 1.31 (6H, s), 2.03 (3H, s), 4.07 (2H, s), 4.29 (1H, s), 5.04 (2H, s), 6.73–6.89 (3H, m).

(36) 3-Amino-4-[(S)-1-tert-butoxycarbonylpyrrolidin-3-ylamino]benzonitrile
NMR(CDCl$_3$, δ): 1.47 (9H, s), 1.95 (1H, br), 2.16–2.32 (1H, m), 3.20–3.59 (6H, m), 4.00–4.11 (2H, m), 6.59 (1H, d, J=8 Hz), 6.96 (1H, s-like), 7.16 (1H, d, J=8 Hz).

(37) 3-Amino-4-[(R)-1-tert-butoxycarbonylpyrrolidin-3-ylamino]benzonitrile
NMR(DMSO-d$_6$, δ): 1.36–1.44 (9H, m), 1.78–1.91 (1H, m), 2.09–2.24 (1H, m), 3.08–3.22 (1H, m), 3.29–3.45 (2H, m), 3.52–3.65 (1H, m), 4.00–4.14 (1H, m), 5.08 (2H, s), 5.39 (1H, d, J=7 Hz), 6.53 (1H, d, J=8 Hz), 6.78 (1H, d, J=2 Hz), 6.93 (1H, dd, J=8, 2 Hz).

(38) 3-Amino-4-[[trans-4-(N-tert-butoxycarbonylamino)cyclohexyl]amino]benzonitrile
NMR(DMSO-d$_6$, δ): 1.14–1.34 (4H, m), 1.38 (9H, s), 1.76–1.87 (2H, m), 1.94–2.03 (2H, m), 3.23 (2H, br), 4.97 (2H, s), 5.08 (1H, d, J=8 Hz), 6.49 (1H, d, J=8 Hz), 6.75 (1H, d, J=2 Hz), 6.81 (1H, d, J=8 Hz), 6.90 (1H, dd, J=8, 2 Hz).

(39) 3-Amino-4-(cis-4-acetoxycyclohexylamino)benzonitrile
NMR(DMSO-d$_6$, δ): 1.48–1.89 (8H, m), 2.02 (3H, s), 3.43 (1H, br), 4.86 (1H, br), 5.03 (2H, s), 5.12 (1H, d, J=7.5 Hz), 6.52 (1H, d, J=7.5 Hz), 6.77 (1H, d, J=2 Hz), 6.90 (1H, dd, J=8, 2 Hz).

(40) 4-(trans-4-Acetoxycyclohexylamino)-3-aminobenzonitrile
NMR(DMSO-d$_6$, δ): 1.22–1.40 (2H, m), 1.40–1.60 (2H, m), 1.87–2.06 (7H, m), 3.29–3.45 (1H, m), 4.56–4.69 (1H, m), 4.90 (2H, s), 5.10 (1H, d, J=7.5 Hz), 6.52 (1H, d, J=8 Hz), 6.76 (1H, d, J=2 Hz), 6.90 (1H, dd, J=8, 2 Hz).

(41) 4-[1-(Acetoxymethyl)cyclopentylamino]-3-aminobenzonitrile
NMR(DMSO-d$_6$, δ): 1.55–1.76 (4H, m), 1.76–2.03 (7H, m), 4.19 (2H, s), 4.88 (1H, s), 5.09 (2H, s), 6.58 (1H, d, J=8 Hz), 6.79 (1H, d, J=2 Hz), 6.86 (1H, dd, J=8, 2 Hz).

(42) 3-Amino-4-cyclopentylaminobenzonitrile
NMR(DMSO-d$_6$, δ): 1.42–1.75 (6H, m), 1.90–2.04 (2H, m), 3.73–3.84 (1H, m), 5.02 (2H, s), 5.19 (1H, d, J=5 Hz), 6.46 (1H, d, J=8 Hz), 6.74 (1H, d, J=2 Hz), 6.90 (1H, dd, J=8, 2 Hz).

(43) 3-Amino-4-(tetrahydro-4H-pyran-4-ylamino)benzonitrile

NMR(DMSO-$d_6$, δ): 1.35–1.51 (2H, m), 1.84–1.94 (2H, m), 3.36–3.49 (2H, m), 3.49–3.63 (1H, m), 3.82–3.93 (2H, m), 5.01 (2H, s), 5.15 (1H, d, J=7.5 Hz), 6.56 (1H, d, J=8 Hz), 6.78 (1H, d, J=2 Hz), 6.90 (1H, dd, J=8, 2 Hz).

(44) 3-Amino-4-cyclohexylaminobenzonitrile

NMR(DMSO-$d_6$, δ): 1.08–1.26 (3H, m), 1.26–1.45 (2H, m), 1.56–1.66 (1H, m), 1.66–1.79 (2H, m), 1.89–2.00 (2H, m), 4.98 (2H, s), 5.07 (1H, d, J=8 Hz), 6.48 (1H, d, J=8 Hz), 6.76 (1H, d, J=2 Hz), 6.89 (1H, dd, J=8, 2 Hz).

(45) 3-Amino-4-tert-butylaminobenzontrile

NMR(CDCl$_3$, δ): 1.36 (9H, s), 4.65 (1H, s), 4.99 (2H, s), 6.74 (1H, d, J=8 Hz), 6.81 (1H, d, J=2 Hz), 6.90 (1H, dd, J=8, 2 Hz).

(46) 3-Amino-4-cycloheptylaminobenzonitrile

NMR(DMSO-$d_6$, δ): 1.39–1.71 (10H, m), 1.80–1.95 (2H, m), 5.00 (2H, s), 5.08 (1H, d, J=8 Hz), 6.37 (1H, d, J=8 Hz), 6.75 (1H, d, J=2 Hz), 6.90 (1H, dd, J=8, 2 Hz).

(47) 4-[((S)-2-Acetoxy-1-ethylethyl)amino]-3-aminobenzonitrile

NMR(CDCl$_3$, δ): 1.01 (3H, t, J=7.5 Hz), 1.53–1.79 (2H, m), 2.04 (3H, s), 2.69 (3H, br), 3.55–3.66 (1H, m), 4.06 (1H, dd, J=11, 5 Hz), 4.28 (1H, dd, J=11, 5 Hz), 6.64 (1H, d, J=8 Hz), 6.95 (1H, d, J=2 Hz), 7.15 (1H, dd, J=8, 2 Hz).

(48) 4-[((R)-2-Acetoxy-1-ethylethyl)amino]-3-aminobenzonitrile

NMR(CDCl$_3$, δ): 1.01 (3H, t, J=7.5 Hz), 1.51–1.80 (2H, m), 2.04 (3H, s), 2.93 (3H, br), 3.55–3.67 (1H, m), 4.06 (1H, dd, J=11, 5 Hz), 4.29 (1H, dd, J=11, 5 Hz), 6.62 (1H, d, J=8 Hz), 6.95 (1H, d, J=2 Hz), 7.15 (1H, dd, J=8, 2 Hz).

(49) 3-Amino-4-[1-(tert-butoxycarbonyl)piperidin-4-ylamino]benzonitrile

NMR(DMSO-$d_6$, δ): 1.16–1.35 (2H, m), 1.40 (9H, s), 1.84–1.95 (2H, m), 2.79–2.98 (2H, m), 3.84–3.96 (2H, m), 4.98 (2H, s), 5.12 (1H, d, J=7.5 Hz), 6.56 (1H, d, J=8 Hz), 6.75 (1H, d, J=2 Hz), 6.90 (1H, dd, J=8, 2 Hz).

(50) 3-Amino-4-(t-3,t-4-isopropylidenedioxy-r-1-cyclohexylamino)benzonitrile

NMR(DMSO-$d_6$, δ): 1.11–1.29 (4H, m), 1.44 (3H, s), 1.53–1.70 (2H, m), 1.75–1.93 (2H, m), 2.14–2.24 (1H, m), 3.55 (1H, br), 4.05–4.15 (1H, m), 4.26–4.34 (1H, m), 5.00 (2H, s), 5.11 (1H, d, J=8 Hz), 6.45 (1H, d, J=8 Hz), 6.77 (1H, d, J=2 Hz), 6.93 (1H, dd, J=8, 2 Hz).

(51) 3-Amino-4-(c-3,c-4-isopropylidenedioxy-r-1-cyclohexylamino)benzonitrile

NMR(DMSO-$d_6$, δ): 1.27 (3H, s), 1.31–1.52 (5H, m), 1.64–1.86 (2H, m), 1.95–2.07 (2H, m), 3.24–3.39 (1H, m), 4.06–4.22 (2H, m), 4.94 (2H, s), 5.16 (1H, d, J=8 Hz), 6.50 (1H, d, J=8 Hz), 6.77 (1H, d, J=2 Hz), 6.90 (1H, dd, J=8, 2 Hz).

(52) 2-[((R)-2-Acetoxy-1-methylethyl)amino]-3-amino-5-cyanopyridine

NMR(DMSO-$d_6$, δ): 1.19(3H, d, J=6.5 Hz), 2.00(3H, s), 3.97–4.10(2H, m), 4.35–4.47(1H, m), 5.25(2H, s), 6.38(1H, d, J=7.0 Hz), 6.82(1H, d, J=2.0 Hz), 7.78(1H, d, J=2.0 Hz).

(53) 3-Amino-2-(trans-4-hydroxycyclohexylamino)-5-methoxycarbonylpyridine mp. 213.5–215° C.

NMR(DMSO-$d_6$, δ): 1.16–1.35(4H, m), 1.77–2.00(4H, m), 3.36–3.47(1H, m), 3.73(3H, s), 3.81–3.95(1H, m), 4.55 (1H, d, J=4.0 Hz), 4.97(2H, s), 6.01(1H, d, J=7.0 Hz), 7.11(1H, d, J=2.0 Hz), 8.01(1H, d, J=2.0 Hz).

MS m/z: 266(M$^+$+1).

(54) 3-Amino-4-[[trans4-(N-tert-butoxycarbonylamino)cyclohexyl]amino]-benzotrifluoride NMR(DMSO-$d_6$, δ): 1.11–1.35(4H, m), 1.38(9H, s), 1.76–1.86(2H, m), 1.95–2.04(2H, m), 3.13–3.28(2H, m), 4.75(1H, d, J=7.5 Hz), 4.92(2H, s), 6.50(1H, d, J=9.0 Hz), 6.73–6.84(3H, m).

(55) 3-Amino-5-cyano-2-(trans-4-hydroxycyclohexylamino)pyridine

NMR(DMSO-$d_6$, δ): 1.16–1.34(4H, m), 1.77–1.98(4H, m), 3.36–3.49(1H, m), 3.78–3.92(1H, m), 4.57(1H, d, J=4.5 Hz), 5.20(2H, s), 6.22(1H, d, J=7.0 Hz), 6.77(1H, d, J=2.0 Hz), 7.78(1H, d, J=2.0 Hz).

MS m/z: 231(M$^+$–1).

(56) 3-Amino-2-((R)-1-tert-butoxycarbonylpyrrolidin-3-ylamino)-5-(trifluoromethyl)pyridine NMR(DMSO-$d_6$, δ): 1.38(9H, s), 1.80–1.95(1H, m), 2.08–2.22(1H, m), 3.10–3.45(3H, m), 3.55–3.68(1H, m), 4.40–4.53(1H, m), 5.27(2H, s), 6.31(1H, d, J=4.5 Hz), 6.86(1H, s), 7.69(1H, s).

MS m/z: 345(M$^+$–1).

(57) To a solution of 5-cyano-2-(trans-4-hydroxycyclohexylamino)-3-nitropyridine (3.35 g) in methanol (17 mL) and dioxane (17 mL) was added 10% palladium on activated carbon (383 mg) under nitrogen atmosphere. The mixture was shaken at room temperature under hydrogen atmosphere (3 atm) for 3 hours. The reaction mixture was filtered through a celite pad. The filtrate was concentrated in vacuo to give 3-amino-5-cyano-2-(trans-4-hydroxycyclohexylamino)pyridine (3.15 g) as a brown amorphous.

NMR(DMSO-$d_6$, δ): 1.16–1.34 (4H, m), 1.77–1.98 (4H, m), 3.36–3.49 (1H, m), 3.78–3.92 (1H, m), 4.57 (1H, d, J=4.5 Hz), 5.20 (2H, s), 6.22 (1H, d, J=7.0 Hz), 6.77 (1H, d, J=2.0 Hz), 7.78 (1H, d, J=2.0 Hz).

MS m/z: 231(M$^+$–1).

(58) 5-Amino-6-(benzimidazol-5-yl)aminonicotinonitrile

NMR(DMSO-$d_6$, δ): 7.10(1H, d, J=1 Hz), 7.72(1H, d, J=8 Hz), 7.79(1H, dd, J=8, 1 Hz), 7.93(1H, d, J=1 Hz), 8.49(1H, d, J=1 Hz), 8.97(1H, br s), 9.27(1H, s).

(59) 5-Amino-6-(1H-indol-5-ylamino)nicotinonitrile mp. 175.5–176.5° C.

NMR(DMSO-$d_6$, δ): 5.49(2H, s), 6.38(1H, m), 6.97(1H, d, J=2.0 Hz), 7.22(1H, dd, J=8.5, 2.0 Hz), 7.30(1H, d, J=2.0 Hz), 7.33(1H, d, J=8.5 Hz), 7.83(1H, d, J=2.0 Hz), 7.85(1H, m), 8.22(1H, s), 10.98(1H, s).

(60) 3-Amino-4-(benzimidazol-5-ylamino)benzonitrile

NMR(DMSO-$d_6$, δ): 5.22 (2H, s), 6.88 (1H, dd, J=8,2 Hz), 6.94–7.04 (3H, m), 7.24 (1H, s), 7.46 (1H, s), 7.55 (1H, d, J=8 Hz), 8.12 (1H, s).

(61) 4-(3-Acetoxypropylamino)-3-aminobenzonitrile

NMR(DMSO-$d_6$, δ): 1.89 (2H, m), 2.01 (3H, s), 3.17 (2H, q, J=5 Hz), 4.10 (2H, t, J=5 Hz), 4.97 (2H, s), 5.39 (1H, t, J=5 Hz), 6.47 (1H, d, J=8 Hz), 6.77 (1H, d, J=2 Hz), 6.92 (1H, dd, J=8,2 Hz).

(62) 3-Amino-4-[2-(N,N-dimethylamino)ethylamino]benzonitrile

NMR(DMSO-$d_6$, δ): 2.18 (6H, s), 2.48 (2H, t, J=5 Hz), 3.18 (2H, q, J=5 Hz), 4.93 (2H, s), 5.25 (1H, t, J=5 Hz), 6.50 (1H, d, J=8 Hz), 6.81 (1H, d, J=2 Hz), 6.98 (1H, dd, J=8,2 Hz).

MS (ES$^+$) m/z: 205.4 (M$^+$+1).

PREPARATION 16

To a solution of 2-(1,1-dimethyl-2-hydroxyethylamino)-3-nitro-5-(trifluoromethyl)pyridine (1.2 g) in pyridine (12 mL) was added acetic anhydride (0.811 mL), and the mixture was stirred at room temperature under nitrogen atmosphere for 4 hours. The resulting mixture was concentrated in vacuo, and the residue was partitioned between ethyl acetate and water. The separated organic layer was washed successively with 1 N-hydrochloric acid, water, an aqueous saturated sodium hydrogencarbonate solution and brine. The organic layer was dried over magnesium sulfate and evaporated in vacuo to give 2-(2-acetoxy-1,1-dimethylethylamino)-3-nitro-5-(trifluoromethyl)pyridine (1.39 g) as a yellow oil.

NMR(DMSO-$d_6$, δ): 1.53(6H, s), 2.04(3H, s), 4.37(2H, s), 8.44(1H, s), 8.66(1H, d, J=2.0 Hz), 8.84(1H, d, J=2.0 Hz).

PREPARATION 17

The following compounds described in (1) to (20) were obtained in a manner similar to Preparation 16.

(1) 2-(trans-4-Acetoxycyclohexylamino)-3-nitro-5-(trifluoromethyl)pyridine
  mp. 132.5–135° C.
  NMR(DMSO-$d_6$, δ): 1.40–1.72(4H, m), 1.91–2.04(4H, m), 2.00(3H, s), 4.16–4.31(1H, m), 4.58–4.69(1H, m), 8.40 (1H, d, J=7.5 Hz), 8.64(1H, d, J=1.5 Hz), 8.84(1H, d, J=1.5 Hz).
  MS m/z: 346($M^+$−1).

(2) 4-(trans-2-Acetoxycyclopentylamino)-3-nitrobenzotrifluoride
  mp. 83–84° C.
  NMR(DMSO-$d_6$, δ): 1.59–1.85(4H, m), 2.02(3H, s), 2.03–2.30(2H, m), 4.11–4.22(1H, m), 5.06–5.13(1H, m), 7.38(1H, d, J=9.0 Hz), 7.84(1H, dd, J=9.0, 2.5 Hz), 8.28(1H, d, J=7.0 Hz), 8.32(1H, d, J=2.5 Hz).
  MS m/z: 331($M^+$−1).

(3) 4-(trans-4-Acetoxycyclohexylamino)-3-nitrotoluene
  mp. 115–116° C.
  NMR(DMSO-$d_6$, δ): 1.37–1.62(4H, m), 1.88–2.06(4H, m), 2.01(3H, s), 2.22(3H, s), 3.58–3.73(1H, m), 4.60–4.72 (1H, m), 7.08(1H, d, J=8.5 Hz), 7.40(1H, dd, J=8.5, 2.5 Hz), 7.83(1H, d, J=8.0 Hz), 7.87(1H, d, J=2.5 Hz).
  MS m/z: 293($M^+$+1).

(4) 4-[1-(Acetoxymethyl)cyclopentylamino]-3-nitrobenzotrifluoride
  NMR(DMSO-$d_6$, δ): 1.62–1.82(4H, m), 1.89–2.11(4H, m), 2.00(3H, s), 4.31(2H, s), 7.35(1H, d, J=9.0 Hz), 7.77 (1H, dd, J=9.0, 2.5 Hz), 8.34(1H, d, J=2.5 Hz), 8.39(1H, s).
  MS m/z: 345($M^+$−1).

(5) 2-[((R)-2-Acetoxy-1-methylethyl)amino]-3-nitro-5-(trifluoromethyl)pyridine
  NMR(DMSO-$d_6$, δ): 1.28(3H, d, J=6.5 Hz), 1.99(3H, s), 4.21(2H, dd, J=6.5, 4.0 Hz), 4.70–4.85(1H, m), 8.55(1H, d, J=8.0 Hz), 8.66(1H, d, J=2.0 Hz), 8.84(1H, d, J=2.0 Hz).

(6) 2-(trans-4-Acetoxycyclohexylamino)-5-(methylsulfonyl)nitrobenzene
  mp. 206–207° C.
  NMR(DMSO-$d_6$, δ): 1.47–1.66(4H, m), 1.90–2.08(4H, m), 2.01(3H, s), 3.21(3H, s), 3.74–3.87(1H, m), 4.61–4.72 (1H, m), 7.37(1H, d, J=9.5 Hz), 7.92(1H, dd, J=9.5, 2.5 Hz), 8.26(1H, d, J=8.0 Hz), 8.50(1H, d, J=2.5 Hz).

(7) 4-[((R)-2-Acetoxy-1-methylethyl)amino]-3-nitrobenzotrifluoride
  NMR(DMSO-$d_6$, δ): 1.28(3H, d, J=6.5 Hz), 2.01(3H, s), 4.10–4.30(3H, m), 7.37(1H, d, J=9.0 Hz), 7.82(1H, dd, J=9.0, 2.5 Hz), 8.24(1H, d, J=7.5 Hz), 8.32(1H, d, J=2.5 Hz).

(8) 2-(trans-4-Acetoxycyclohexylamino)-5-cyano-3-nitropyridine
  mp. 168–170° C.
  NMR(DMSO-$d_6$, δ): 1.40–1.56(2H, m), 1.57–1.76(2H, m), 1.88–2.02(4H, m), 2.00(3H, s), 4.16–4.30(1H, m), 4.56–4.70(1H, m), 8.51(1H, d, J=7.5 Hz), 8.84(1H, d, J=2.0 Hz), 8.89(1H, d, J=2.0 Hz).
  MS m/z: 303($M^+$−1).

(9) 4-(trans-4-Acetoxycyclohexylamino)-3-nitrobenzophenone
  mp. 205–205.5° C.
  NMR(DMSO-$d_6$, δ): 1.48–1.68(4H, m), 1.90–2.10(4H, m), 2.01(3H, s), 3.75–3.87(1H, m), 4.62–4.73(1H, m), 7.33 (1H, d, J=9.5 Hz), 7.57(1H, t, J=7.5 Hz), 7.58(1H, d, J=7.5 Hz), 7.65–7.73(3H, m), 7.96(1H, dd, J=9.5, 2.0 Hz), 8.31 (1H, d, J=7.5 Hz), 8.43(1H, d, J=2.0 Hz).
  MS m/z: 381($M^+$−1).

(10) 4-(2-Acetoxyethylamino)-3-nitrobenzotrifluoride
  mp. 48–48° C.
  NMR(DMSO-$d_6$, δ): 2.01(3H, s), 3.71(2H, q, J=5.5 Hz), 4.25(2H, t, J=5.5 Hz), 7.33(1H, d, J=9.0 Hz), 7.82(1H, dd, J=9.0, 2.0 Hz), 8.32(1H, d, J=2.0 Hz), 8.56(1H, t, J=5.5 Hz).
  MS m/z: 291($M^+$−1).

(11) 4-(2-Acetoxy-1,1-dimethylethylamino)-3-nitrobenzonitrile
  NMR(CDCl$_3$, δ): 1.55 (6H, s), 2.13 (3H, s), 4.21 (2H, s), 7.16 (1H, d, J=8 Hz), 7.56 (1H, dd, J=8, 2 Hz), 8.54 (1H, d, J=2 Hz), 8.84 (1H, br).

(12) 4-[((R)-2-Acetoxy-1-methylethyl)amino]-3-nitrobenzonitrile
  NMR(CDCl$_3$, δ): 1.40 (3H, d, J=7 Hz), 2.09 (3H, s), 3.08–4.17 (2H, m), 4.20–4.81 (1H, m), 7.06 (1H, d, J=8 Hz), 7.63 (1H, dd, J=8, 2 Hz), 8.45 (1H, br d, J=8 Hz), 8.53 (1H, d, J=2 Hz).

(13) 4-[((S)-2-Acetoxy-1-methylethyl)amino]-3-nitrobenzonitrile
  NMR(CDCl$_3$, δ): 1.40 (3H, d, J=7 Hz), 2.09 (3H, s), 3.99–4.15 (2H, m), 4.20–4.31 (1H, m), 7.05 (1H, d, J=8 Hz), 7.62 (1H, dd, J=8, 2 Hz), 8.45 (1H, br d, J=8 Hz), 8.53 (1H, d, J=2 Hz).

(14) 4-[2-Acetoxy-1,1-dimethylethylamino]-3-nitrobenzotrifluoride
  NMR(CDCl$_3$, δ): 1.54 (6H, s), 2.13 (3H, s), 4.22 (2H, s), 7.18 (1H, d, J=8 Hz), 7.58 (1H, dd, J=8, 2 Hz), 8.50 (1H, d, J=2 Hz), 8.70 (1H, br s).

(15) 4-(trans-4-Acetoxycyclohexylamino)-3-nitrobenzonitrile
  NMR(DMSO-$d_6$, δ): 1.45–1.66 (4H, m), 1.87–2.06 (7H, m), 3.78 (1H, br), 4.59–4.72 (1H, m), 7.30 (1H, d, J=8 Hz), 7.84 (1H, dd, J=8, 2 Hz), 8.22 (1H, d, J=8 Hz), 8.52 (1H, d, J=2 Hz).

(16) 4-[1-(Acetoxymethyl)cyclopentylamino]-3-nitrobenzonitrile
  NMR(CDCl$_3$, δ): 1.70–1.94 (4H, m), 1.96–2.08 (7H, m), 4.29 (2H, s), 7.04 (1H, d, J=8 Hz), 7.56 (1H, dd, J=8, 2 Hz), 8.53 (1H, d, J=2 Hz), 8.70 (1H, br).

(17) 4-[((S)-2-Acetoxy-1-ethylethyl)amino]-3-nitrobenzonitrile
  NMR(CDCl$_3$, δ): 1.05 (3H, d, J=7.5 Hz), 1.61–1.94 (2H, m), 2.07 (3H, s), 3.77–3.92 (1H, m), 4.14 (1H, dd, J=11, 5 Hz), 4.26 (1H, dd, J=11, 5 Hz), 7.05 (1H, d, J=8 Hz), 7.60 (1H, dd, J=8, 2 Hz), 8.44 (1H, d, J=8 Hz), 8.53 (1H, d, J=2 Hz).

(18) 4-[((R)-2-Acetoxy-1-ethylethyl)amino]-3-nitrobenzonitrile
  NMR(CDCl$_3$, δ): 1.05 (3H, t, J=7.5 Hz), 1.61–1.76 (2H, m), 1.76–1.94 (1H, m), 2.07 (3H, s), 3.79–3.94 (1H, m), 4.14 (1H, dd, J=11, 5 Hz), 4.26 (1H, dd, J=11, 5 Hz), 7.06 (1H, d, J=8 Hz), 7.61 (1H, dd, J=8, 2 Hz), 8.44 (1H, d, J=8 Hz), 8.53 (1H, d, J=2 Hz).

(19) 2-[((R)-2-Acetoxy-1-methylethyl)amino]-5-cyano-3-nitropyridine
  NMR(DMSO-$d_6$, δ): 1.48(3H, d, J=7.0 Hz), 2.19(3H, s), 4.41(2H, t, J=6.0 Hz), 4.90–5.05(1H, m), 8.88(1H, d, J=7.5 Hz), 9.05(1H, d, J=2.0 Hz), 9.11(1H, d, J=2.0 Hz).
  MS m/z: 263($M^+$−1).

(20) 4-(3-Acetoxypropylamino)-3-nitrobenzonitrile

NMR (CDCl$_3$, δ): 2.04–2.18 (5H, m), 3.48 (2H, q, J=5 Hz), 4.25 (2H, t, J=5 Hz), 6.92 (1H, d, J=8 Hz), 7.63 (1H, dd, J=8,2 Hz), 8.52 (1H, d, J=2 Hz), 8.56 (1H, br peak).

MS (ES$^-$) m/z: 262.2(M$^+$−1).

PREPARATION 18

A mixture of 4-[2-hydroxy-1-(hydroxymethyl) ethylamino]-3-nitrobenzonitrile (1.35 g), 2,2-dimethoxypropane (1.4 g) and p-toluenesulfonic acid (10 mg) in anhydrous dichloromethane (30 mL) was stirred at ambient temperature for 8 hours. The mixture was poured into water and extracted with chloroform. The organic layer was washed with brine and dried over magnesium sulfate. After evaporation of the solvent, the residue was triturated with diethyl ether to give 4-[(2,2-dimethyl-1,3-dioxan-5-yl) amino[-3-nitrobenzonitrile (1.3 g) as yellow powders.

NMR(DMSO-d$_6$, δ): 1.36 (3H, s), 1.45 (3H, s), 3.70–3.80 (2H, m), 3.90–3.99 (1H, m), 4.10–4.20 (2H, m), 7.29 (1H, d, J=8 Hz), 7.85 (1H, dd, J=8, 2 Hz), 8.57 (1H, d, J=2 Hz), 8.90 (1H, d, J=8 Hz).

PREPARATION 19

The following compounds described in (1) and (2) were obtained in a manner similar to Preparation 18.

(1) 4-(t-3,t-4-Isopropylidenedioxy-r-1-cyclohexylamino)-3-nitrobenzonitrile

NMR(CDCl$_3$, δ): 1.33–1.51 (4H, m), 1.56 (3H, s), 1.66–1.86 (2H, m), 1.94–2.05 (1H, m), 2.05–2.19 (1H, m), 2.41–2.51 (1H, m), 3.85–4.00 (1H, m), 4.16–4.26 (1H, m), 4.34–4.41 (1H, m), 6.96 (1H, d, J=8 Hz), 7.60 (1H, dd, J=8, 2 Hz), 8.34 (1H, br d, J=8 Hz), 8.51 (1H, d, J=2 Hz).

MS m/z: 316.2 (M$^+$−1).

(2) 4-(c-3,c-4-Isopropylidenedioxy-r-1-cyclohexylamino)-3-nitrobenzonitrile

NMR(CDCl$_3$, δ): 1.39 (3H, s), 1.59 (3H, s), 1.64–1.96 (4H, m), 2.04–2.25 (2H, m), 3.76–3.88 (1H, m), 4.14–4.25 (1H, m), 4.29–4.37 (1H, m), 6.86 (1H, d, J=8 Hz), 7.56 (1H, dd, J=8, 2 Hz), 8.51 (1H, d, J=2 Hz), 9.05 (1H, br d, J=8 Hz).

MS m/z: 316.1(M$^+$−1).

PREPARATION 20

A mixture of 4-[(trans-4-aminocyclohexyl)amino]-3-nitrobenzonitrile (987 mg), di-tert-butyl dicarbonate (910 mg) and triethylamine (422 mg) in anhydrous N,N-dimethylformamide (10 mL) was stirred at ambient temperature for 5 hours. The mixture was partitioned between water and ethyl acetate. The separated organic layer was washed successively with water and brine and dried over magnesium sulfate. After evaporation of the solvent, the residue was triturated with diisopropyl ether to give 4-[[trans-4-(N-tert-butoxycarbonylamino)cyclohexyl] amino]-3-nitrobenzonitrile (1.23 g) as yellow powders.

NMR(CDCl$_3$, δ): 1.21–1.40 (2H, m), 1.40–1.54 (11H, m), 2.10–2.23 (4H, m), 3.40–3.61 (2H, m), 4.42 (1H, br), 6.90 (1H, d, J=8 Hz), 7.66 (1H, dd, J=8, 2 Hz), 8.35 (1H, d, J=8 Hz), 8.51 (1H, d, J=2 Hz).

PREPARATION 21

4-[[trans-4-(N-tert-Butoxycarbonylamino)cyclohexyl] amino]-3-nitrobenzotrifluoride was obtained in a manner similar to Preparation 20.

mp. 189.5–190° C.

NMR(DMSO-d$_6$, δ): 1.48–1.75(4H, m), 1.60(9H, s), 1.97–2.08(2H, m), 2.16–2.26(2H, m), 3.43–3.52(1H, m), 3.76–3.90(1H, m), 7.06(1H, d, J=7.5 Hz), 7.55(1H, d, J=9.0 Hz), 7.96(1H, dd, J=9.0, 2.5 Hz), 8.34(1H, d, J=7.5 Hz), 8.52(1H, d, J=2.5 Hz).

MS m/z: 402(M$^+$−1).

PREPARATION 22

To a solution of 3-amino-4-(trans-4-hydroxycyclohexylamino)benzotrifluoride (657 mg) in acetonitrile (7 mL) was added 1,1'-carbonyldiimidazole (1.17 g), and the mixture was stirred at 60° C. under nitrogen atmosphere for 3 hours. After adding 1N-sodium hydroxide solution (5 mL), the mixture was stirred at 60° C. for an hour. The mixture was neutralized with concentrated hydrochloric acid at 0° C. The resulting precipitate was collected by filtration and washed successively with water and diethyl ether to give 1-(trans-4-hydroxycyclohexyl)-5-trifluoromethyl-2,3-dihydro-1H-benzimidazol-2-one (549.5 mg) as a colorless solid.

mp. 232.5–233° C.

NMR(DMSO-d$_6$, δ): 1.25–1.45(2H, m), 1.60–1.73(2H, m), 1.87–2.00(2H, m), 2.11–2.30(2H, m), 3.50–3.63(1H, m), 4.10–4.24(1H, m), 4.68(1H, d, J=4.0 Hz), 7.20(1H, s), 7.32(1H, d, J=8.5 Hz), 7.49(1H, d, J=8.5 Hz).

MS m/z: 299(M$^+$−1).

PREPARATION 23

The following compounds described in (1) to (8) were obtained in a manner similar to Preparation 22.

(1) 1-(trans-4-Hydroxycyclohexyl)-5-nitro-2,3-dihydro-1H-benzimidazol-2-one mp. 300–301° C.

NMR(DMSO-d$_6$, δ): 1.26–1.45(2H, m), 1.63–1.75(2H, m), 1.88–2.00(2H, m), 2.11–2.29(2H, m), 3.49–3.63(1H, m), 4.13–4.27(1H, m), 4.68(1H, brs), 7.53(1H, d, J=9.0 Hz), 7.74(1H, d, J=2.5 Hz), 7.96(1H, dd, J=9.0, 2.5 Hz).

MS m/z: 276(M$^+$−1).

(2) 5-Acetyl-1-(trans-4-hydroxycyclohexyl)-2,3-dihydro-1H-benzimidazol-2-one mp. 253.5–255° C.

NMR(DMSO-d$_6$, δ): 1.26–1.44(2H, m), 1.61–1.72(2H, m), 1.88–1.99(2H, m), 2.12–2.30(2H, m), 2.54(3H, s), 3.50–3.64(1H, m), 4.10–4.24(1H, m), 4.68(1H, d, J=4.5 Hz), 7.40(1H, d, J=8.5 Hz), 7.49(1H, d, J=2.5 Hz), 7.68(1H, dd, J=8.5, 2.5 Hz).

MS m/z: 273(M$^+$−1).

(3) 5-Chloro-1-(trans-4-hydroxycyclohexyl)-2,3-dihydro-1H-benzimidazol-2-one mp. 248–249.5° C.

NMR(DMSO-d$_6$, δ): 1:24–1.41(2H, m), 1.57–1.68(2H, m), 1.87–1.97(2H, m), 2.07–2.29(2H, m), 3.33(1H, brs), 3.49–3.62(1H, m), 4.04–4.17(1H, m), 4.66(1H, brs), 6.95 (1H, d, J=2.5 Hz), 6.98(1H, dd, J=9.0, 2.5 Hz), 7.29(1H, d, J=9.0 Hz).

MS m/z: 265(M$^+$−1).

(4) 1-(trans-4-Hydroxycyclohexyl)-5-methoxycarbonyl-2,3-dihydro-1H-benzimidazol-2-one mp. 233–236° C.

NMR(DMSO-d$_6$, δ): 1.25–1.43(2H, m), 1.61–1.72(2H, m), 1.87–1.99(2H, m), 2.12–2.28(2H, m), 3.34(1H, s), 3.49–3.63(1H, m), 3.82(3H, s), 4.09–4.23(1H, m), 4.67(1H, d, J=4.5 Hz), 7.41(1H, d, J=8.5 Hz), 7.49(1H, d, J=1.5 Hz), 7.65(1H, dd, J=8.5, 1.5 Hz).

MS m/z: 289(M$^+$−1).

(5) 1-(trans-4-Hydroxycyclohexyl)-5-methoxy-2,3-dihydro-1H-benzimidazol-2-one mp. 262–264° C.

NMR(DMSO-d$_6$, δ): 1.24–1.41(2H, m), 1.56–1.67(2H, m), 1.87–1.97(2H, m), 2.05–2.23(2H, m), 3.46–3.61(1H, m), 3.57(1H, s), 3.70(3H, s), 4.00–4.14(1H, m), 4.65(1H, d, J=4.5 Hz), 6.53(1H, dd, J=9.5, 2.5 Hz), 6.54(1H, d, J=2.5 Hz), 7.15(1H, d, J=9.5 Hz).

MS m/z: 261 (M$^+$−1).

(6) 3-(trans-4-Hydroxycyclohexyl)-6-methoxycarbonyl-2,3-dihydro-1H-imidazo[4,5-b]pyridin-2-one mp. 254.5–255° C.

NMR(DMSO-d$_6$, δ): 1.22–1.40(2H, m), 1.62–1.74(2H, m), 1.89–2.00(2H, m), 2.25–2.48(2H, m), 3.40–3.55(1H, m), 3.85(3H, s), 4.17–4.30(1H, m), 4.67(1H, d, J=4.5 Hz), 7.62(1H, d, J=2.0 Hz), 8.56(1H, d, J=2.0 Hz).

MS m/z: 290(M$^+$−1).

(7) 6-Cyano-3-(trans-4-hydroxycyclohexyl)-2,3-dihydro-1H-imidazo[4,5-b]pyridin-2-one mp. 274–275° C.

NMR(DMSO-d$_6$, δ): 1.22–1.39(2H, m), 1.63–1.75(2H, m), 1.88–1.99(2H, m), 2.25–2.44(2H, m), 3.42–3.55(1H, m), 4.15–4.27(1H, m), 4.68(1H, d, J=4.5 Hz), 7.70(1H, d, J=2.0 Hz), 8.42(1H, d, J=2.0 Hz).

MS m/z: 257(M$^+$−1).

(8) 6-Cyano-3-(trans-4-hydroxycyclohexyl)-2,3-dihydro-1H-imidazo[4,5-b]pyridin-2-one mp. 274–275° C.

NMR(DMSO-d$_6$, δ): 1.22–1.39(2H, m), 1.63–1.75(2H, m), 1.88–1.99(2H, m), 2.25–2.44(2H, m), 3.42–3.55(1H, m), 4.15–4.27(1H, m), 4.68(1H, d, J=4.5 Hz), 7.70(1H, d, J=2.0 Hz), 8.42(1H, d, J=2.0 Hz).

MS m/z: 257(M$^+$−1).

PREPARATION 24

To a solution of 2-(2-acetoxy-1,1-dimethylethylamino)-3-amino-5-(trifluoromethyl)pyridine (1.5 g) in acetonitrile (15 mL) was added 1,1'-carbonyldiimidazole (1.25 g), and the mixture was stirred at 50° C. under nitrogen atmosphere for 2 hours. After cooling to room temperature, the mixture was concentrated in vacuo. The residue was partitioned between ethyl acetate and water. The separated organic layer was washed successively with 1 N-hydrochloric acid, water, an aqueous saturated sodium hydrogencarbonate solution and brine. The organic layer was dried over magnesium sulfate and evaporated in vacuo. The residue was subjected to a silica gel column chromatography eluting with a mixture of chloroform and methanol (20:1). The obtained substance was triturated with diethyl ether to give 3-(2-acetoxy-1,1-dimethylethyl)-6-trifluoromethyl-2,3-dihydro-1H-imidazo[4,5-b]pyridin-2-one (736.5 mg) as a pale brown solid.

mp. 132–132.5° C.

NMR(DMSO-d$_6$, δ): 1.78(6H, s), 1.91(3H, s), 4.61(2H, s), 7.48(1H, d, J=1.5 Hz), 8.31(1H, d, J=1.5 Hz).

MS m/z: 316(M$^+$−1).

PREPARATION 25

The following compounds described in (1) to (44) and (46) to (50) were obtained in a manner similar to Preparation 24.

(1) 3-(trans-4-Acetoxycyclohexyl)-6-trifluoromethyl-2,3-dihydro-1H-imidazo[4,5-b]pyridin-2-one mp. 256–257° C.

NMR(DMSO-d$_6$, δ): 1.45–1.62(2H, m), 1.72–1.85(2H, m), 1.95–2.07(2H, m), 2.02(3H, s), 2.37–2.54(2H, m), 4.25–4.40(1H, m), 4.59–4.73(1H, m), 7.53(1H, d, J=1.5 Hz), 8.35(1H, d, J=1.5 Hz).

MS m/z : 342(M$^+$−1).

(2) 3-Cyclopentyl-6-trifluoromethyl-2,3-dihydro-1H-imidazo[4,5-b]pyridin-2-one mp. 193–194.5° C.

NMR(DMSO-d$_6$, δ): 1.55–1.72(2H, m), 1.83–1.99(4H, m), 2.11–2.29(2H, m), 4.73–4.87(1H, m), 7.53(1H, s), 8.35(1H, s).

MS m/z: 270(M$^+$−1).

(3) 1-(trans-2-Acetoxycyclopentyl)-5-trifluoromethyl-2,3-dihydro-1H-benzimidazol-2-one mp. 171–172° C.

NMR(DMSO-d$_6$, δ): 1.65–1.95(3H, m), 1.92(3H, s), 2.02–2.15(2H, m), 2.19–2.29(1H, m), 4.63–4.74(1H, m), 5.47–5.55(1H, m), 7.22(1H, d, J=1.0 Hz), 7.35(1H, dd, J=8.0, 1.0 Hz), 7.40(1H, d, J=8.0 Hz).

MS m/z: 327(M$^+$−1).

(4) 1-((S)-1-tert-Butoxycarbonylpyrrolidin-3-yl)-5-trifluoromethyl-2,3-dihydro-1H-benzimidazol-2-one mp. 189–190° C.

NMR(DMSO-d$_6$, δ): 1.41(9H, s), 2.07–2.20(1H, m), 2.41–2.53(1H, m), 3.27–3.40(1H, m), 3.51–3.70(3H, m), 4.95–5.09(1H, m), 7.23(1H, s), 7.38(2H, s).

MS m/z: 370(M$^+$−1).

(5) 1-(1H-Benzimidazol-5-yl)-5-trifluoromethyl-2,3-dihydro-1H-benzimidazol-2-one mp. 298–299° C.

NMR(DMSO-d$_6$, δ): 7.07(1H, brs), 7.30(1H, brs), 7.33(1H, s), 7.35(1H, d, J=8.0 Hz), 7.66–7.86(2H, m), 8.36(1H, s).

MS m/z: 317(M$^+$−1).

(6) 1-(trans-4-Acetoxycyclohexyl)-5-methyl-2,3-dihydro-1H-benzimidazol-2-one mp. 209.5–210° C.

NMR(DMSO-d$_6$, δ): 1.44–1.61(2H, m), 1.64–1.75(2H, m), 1.96–2.06(2H, m), 2.01(3H, s), 2.18–2.35(2H, m), 2.28(3H, s), 4.11–4.25(1H, m), 4.72–4.85(1H, m), 6.73–6.79(2H, m), 7.23(1H, d, J=8.5 Hz).

MS m/z: 287(M$^+$−1).

(7) 1-[1-(Acetoxymethyl)cyclopentyl]-5-trifluoromethyl-2,3-dihydro-1H-benzimidazol-2-one mp. 152–153° C.

NMR(DMSO-d$_6$, δ): 1.59–1.81(4H, m), 1.77(3H, s), 2.20–2.35(2H, m), 2.45–2.62(2H, m), 4.27(2H, s), 7.16(1H, d, J=1.5 Hz), 7.28(1H, dd, J=8.5, 1.5 Hz), 7.48(1H, d, J=8.5 Hz).

MS m/z: 341(M$^+$−1).

(8) 3-((R)-2-Acetoxy-1-methylethyl)-6-trifluoromethyl-2,3-dihydro-1H-imidazo[4,5-b]pyridin-2-one mp. 155–156° C.

NMR(DMSO-d$_6$, δ): 1.51(3H, d, J=7.0 Hz), 1.87(3H, s), 4.37(1H, dd, J=11.5, 5.0 Hz), 4.58(1H, dd, J=11.5, 9.5 Hz), 4.68–4.82(1H, m), 7.56(1H, d, J=2.0 Hz), 8.35(1H, d, J=2.0 Hz).

MS m/z: 302(M$^+$−1).

(9) 1-(trans-4-Acetoxycyclohexyl)-5-methylsulfonyl-2,3-dihydro-1H-benzimidazol-2-one mp. 275–275.5° C.

NMR(DMSO-d$_6$, δ): 1.46–1.63(2H, m), 1.70–1.80(2H, m), 1.98–2.09(2H, m), 2.02(3H, s), 2.21–2.39(2H, m), 3.17(3H, s), 4.21–4.36(1H, m), 4.75–4.88(1H, m), 7.43(1H, d, J=2.5 Hz), 7.54(1H, dd, J=8.5, 2.5 Hz), 7.65(1H, d, J=8.5 Hz).

MS m/z: 351(M$^+$−1).

(10) 1-((R)-2-Acetoxy-1-methylethyl)-5-trifluoromethyl-2,3-dihydro-1H-benzimidazol-2-one mp. 132–132.5° C.

NMR(DMSO-d$_6$, δ): 1.47(3H, d, J=7.0 Hz), 1.88(3H, s), 4.31(1H, dd, J=11.5, 5.0 Hz), 4.49(1H, dd, J=11.5, 9.0 Hz), 4.62–4.75(1H, m), 7.22(1H, s), 7.35(1H, d, J=8.5 Hz), 7.46(1H, d, J=8.5 Hz).

MS m/z: 301(M$^+$−1).

(11) 3-(trans-4-Acetoxycyclohexyl)-6-cyano-2,3-dihydro-1H-imidazo[4,5-b]pyridin-2-one
mp. 270.5–271° C.
NMR(DMSO-d$_6$, δ): 1.45–1.61(2H, m), 1.73–1.84(2H, m), 1.95–2.08(2H, m), 2.01(3H, s), 2.33–2.55(2H, m), 4.25–4.39(1H, m), 4.59–4.71(1H, m), 7.72(1H, d, J=2.0 Hz), 8.44(1H, d, J=2.0 Hz).

(12) 1-(trans-4-Acetoxycyclohexyl)-5-benzoyl-2,3-dihydro-1H-benzimidazol-2-one
mp. 275–277° C.
NMR(DMSO-d$_6$, δ): 1.48–1.65(2H, m), 1.72–1.83(2H, m), 1.95–2.10(2H, m), 2.02(3H, s), 2.22–2.40(2H, m), 4.22–4.35(1H, m), 4.74–4.87(1H, m), 7.35(1H, d, J=2.0 Hz), 7.45(1H, dd, J=7.5, 2.0 Hz), 7.51–7.60(3H, m), 7.65(1H, d, J=7.5 Hz), 7.70(2H, d, J=7.5 Hz).
MS m/z: 377(M$^+$−1).

(13) 1-(tert-Butyl)-5-trifluoromethyl-2,3-dihydro-1H-benzimidazol-2-one
mp. 188–190° C.
NMR(DMSO-d$_6$, δ): 1.71(9H, s), 7.16(1H, d, J=2.5 Hz), 7.26(1H, dd, J=8.5, 2.5 Hz), 7.60(1H, d, J=8.5 Hz).

(14) 1-(2-Acetoxyethyl)-5-trifluoromethyl-2,3-dihydro-1H-benzimidazol-2-one
mp. 124.5–125° C.
NMR(DMSO-d$_6$, δ): 1.89(3H, s), 4.10(2H, t, J=5.5 Hz), 4.28(2H, t, J=5.5 Hz), 7.23(1H, d, J=2.0 Hz), 7.36(1H, d, J=8.5 Hz), 7.40(1H, dd, J=8.5, 2.0 Hz).
MS m/z: 287(M$^+$−1).

(15) 1-(Tetrahydro-4H-pyran-4-yl)-5-trifluoromethyl-2,3-dihydro-1H-benzimidazol-2-one
mp. 195–196° C.
NMR(DMSO-d$_6$, δ): 1.61–1.70(2H, m), 2.29–2.45(2H, m), 3.41–3.52(2H, m), 3.95–4.03(2H, m), 4.39–4.51(1H, m), 7.23(1H, d, J=1.5 Hz), 7.35(1H, dd, J=8.5, 1.5 Hz), 7.48(1H, d, J=8.5 Hz).
MS m/z: 285(M$^+$−1).

(16) 1-Isopropyl-5-trifluoromethyl-2,3-dihydro-1H-benzimidazol-2-one
mp. 168–169° C.
NMR(DMSO-d$_6$, δ): 1.45(6H, d, J=7.0 Hz), 4.61(1H, hept., J=7.0 Hz), 7.21(1H, d, J=1.0 Hz), 7.33(1H, dd, J=8.5, 1.0 Hz), 7.45(1H, d, J=8.5 Hz).
MS m/z: 245(M$^+$+1).

(17) 1-Butyl-5-trifluoromethyl-2,3-dihydro-1H-benzimidazol-2-one
mp. 140–141° C.
NMR(DMSO-d$_6$, δ): 0.89(3H, t, J=7.0 Hz), 1.21–1.35 (2H, m), 1.56–1.68(2H, m), 3.83(2H, t, J=7.0 Hz), 7.22(1H, s), 7.32(1H, d, J=8.5 Hz), 7.37(1H, d, J=8.5 Hz).

(18) 1-Cyclohexyl-5-trifluoromethyl-2,3-dihydro-1H-benzimidazol-2-one
mp. 216–217° C.
NMR(DMSO-d$_6$, δ): 1.19–1.49(3H, m), 1.61–1.75(3H, m), 1.79–1.90(2H, m), 2.02–2.18(2H, m), 4.11–4.24(1H, m), 7.21(1H, d, J=1.0 Hz), 7.21(1H, dd, J=8.0, 1.0 Hz), 7.49(1H, d, J=8.0 Hz).
MS m/z: 283(M$^+$−1).

(19) 3-(trans-4-Formamidocyclohexyl)-6-trifluoromethyl-2,3-dihydro-1H-imidazo[4,5-b]pyridin-2-one
mp. 303–304° C.
NMR(DMSO-d$_6$, δ): 1.29–1.49(2H, m), 1.70–1.81(2H, m), 1.85–1.97(2H, m), 2.35–2.52(2H, m), 3.59–3.75(1H, m), 4.20–4.35(1H, m), 7.53(1H, d, J=2.0 Hz), 7.97(1H, s), 8.05(1H, m), 8.35(1H, s).
MS m/z: 327(M$^+$−1).

(20) 5-Cyano-1-(trans-4-formamidocyclohexyl)-2,3-dihydro-1H-benzimidazol-2-one
NMR(DMSO-d$_6$, δ): 1.30–1.53(2H, m), 1.65–1.77 (2H, m), 1.82–1.99 (2H, m), 2.16–2.34 (2H, m), 3.72–3.89 (1H, m), 4.13–4.29 (1H, m), 7.36 (1H, d, J=2 Hz), 7.44 (1H, dd, J=8, 2 Hz), 7.59 (1H, d, J=8 Hz), 7.97 (1H, s), 8.04 (1H, d, J=8 Hz).

(21) 5-Cyano-1-(2,2-dimethyl-1,3-dioxan-5-yl)-2,3-dihydro-1H-benzimidazol-2-one
NMR(DMSO-d$_6$, δ): 1.41 (3H, s), 1.51 (3H, s), 3.99 (2H, dd, J=11, 5 Hz), 4.24 (2H, dd, J=11, 7.5 Hz), 4.46–4.58 (1H, m), 7.39 (1H, d, J=2 Hz), 7.50 (1H, dd, J=8, 2 Hz), 7.70 (1H, d, J=8 Hz).

(22) 1-(2-Acetoxy-1,1-dimethylethyl)-5-cyano-2,3-dihydro-1H-benzimidazol-2-one
NMR(DMSO-d$_6$, δ): 1.73 (6H, s), 1.89 (3H, s), 4.50 (2H, s), 7.32 (1H, d, J=2 Hz), 7.38 (1H, dd, J=8, 2 Hz), 7.58 (1H, d, J=8 Hz).

(23) 1-[(R)-2-Acetoxy-1-methylethyl]-5-cyano-2,3-dihydro-1H-benzimidazol-2-one
NMR(DMSO-d$_6$, δ): 1.46 (3H, d, J=7.5 Hz), 1.86 (3H, s), 4.29 (1H, dd, J=11, 4 Hz), 4.47 (1H, dd, J=11, 9 Hz), 4.62–4.76 (1H, m), 7.38 (1H, s), 7.41–7.51 (2H, m).

(24) 1-[(S)-2-Acetoxy-1-methylethyl]-5-cyano-2,3-dihydro-1H-benzimidazol-2-one
NMR(DMSO-d$_6$, δ): 1.46 (3H, d, J=7.5 Hz), 1.86 (3H, s), 4.29 (1H, dd, J=11, 4 Hz), 4.47 (1H, dd, J=11, 9 Hz), 4.62–4.76 (1H, m), 7.37 (1H, s), 7.41–7.51 (2H, m).

(25) 1-(2-Acetoxy-1,1-dimethylethyl)-5-trifluoromethyl-2,3-dihydro-1H-benzimidazol-2-one
NMR(CDCl$_3$, δ): 1.86 (6H, s), 1.98 (3H, s), 4.64 (2H, s), 7.25–7.33 (2H, m), 7.44 (1H, d, J=8 Hz).

(26) 1-[(S)-1-tert-Butoxycarbonylpyrrolidin-3-yl]-5-cyano-2,3-dihydro-1H-benzimidazol-2-one
NMR(CDCl$_3$, δ): 1.50 (9H, s), 2.23–2.36 (1H, m), 2.46–2.64 (1H, m), 3.41–3.56 (1H, m), 3.66–3.90 (3H, m), 5.04–5.20 (1H, m), 7.12 (1H, d, J=8 Hz), 7.36–7.46 (2H, m).

(27) 1-[(R)-1-tert-Butoxycarbonylpyrrolidin-3-yl]-5-cyano-2,3-dihydro-1H-benzimidazol-2-one
NMR(DMSO-d$_6$, δ): 1.41 (9H, s), 2.05–2.20 (1H, m), 2.40–2.56 (1H, m), 3.25–3.40 (1H, m), 3.50–3.70 (3H, m), 4.94–5.10 (1H, m), 7.31–7.41 (2H, m), 7.55 (1H, dd, J=8, 2 Hz).

(28) 1-[trans-4-(N-tert-Butoxycarbonylamino)cyclohexyl]-5-cyano-2,3-dihydro-1H-benzimidazol-2-one
NMR(DMSO-d$_6$, δ): 1.26–1.47 (11H, m), 1.63–1.74 (2H, m), 1.84–1.96 (2H, m), 2.12–2.30 (2H, m), 3.40 (1H, br), 4.07–4.21 (1H, m), 6.80 (1H, d, J=8 Hz), 7.36 (1H, d, J=2 Hz), 7.43 (1H, dd, J=8, 2 Hz), 7.55 (1H, d, J=8 Hz).

(29) 1-(cis-4-Acetoxycyclohexyl)-5-cyano-2,3-dihydro-1H-benzimidazol-2-one
NMR(CDCl$_3$, δ): 1.65–1.82 (4H, m), 2.08–2.21 (5H, m), 2.35–2.52 (2H, m), 4.35–4.48 (1H, m), 5.11–5.27 (1H, m), 7.21 (1H, d, J=8 Hz), 7.37 (1H, d, J=2 Hz), 7.42 (1H, dd, J=8, 2 Hz), 9.53 (1H, s).

(30) 1-(trans-4-Acetoxycyclohexyl)-5-cyano-2,3-dihydro-1H-benzimidazol-2-one
NMR(CDCl$_3$, δ): 1.50–1.71 (2H, m), 1.89–2.03 (2H, m), 2.08 (3H, s), 2.13–2.43 (4H, m), 4.26–4.41 (1H, m), 4.77–4.92 (1H, m), 7.20 (1H, d, J=8 Hz), 7.35–7.46 (2H, m), 9.65 (1H, s).

(31) 1-[1-(Acetoxymethyl)cyclopentyl]-5-cyano-2,3-dihydro-1H-benzimidazol-2-one
NMR(DMSO-d$_6$, δ): 1.60–1.81 (7H, m), 2.17–2.31 (2H, m), 2.40–2.64 (2H, m), 4.26 (2H, s), 7.31 (1H, s-like), 7.38 (1H, d, J=8 Hz), 7.46 (1H, d, J=8 Hz).

(32) 5-Cyano-1-cyclopentyl-2,3-dihydro-1H-benzimidazol-2-one
NMR(CDCl$_3$, δ): 1.66–1.86 (2H, m), 1.91–2.15 (6H, m), 4.86 (1H, quint, J=7.5 Hz), 7.12 (1H, d, J=8 Hz), 7.34–7.42 (2H, m), 9.82 (1H, s).

(33) 5-Cyano-1-(tetrahydro-4H-pyran-4-yl)-2,3-dihydro-1H-benzimidazol-2-one

NMR(DMSO-$d_6$, δ): 1.61–1.70 (2H, m), 2.26–2.45 (2H, m), 3.40–3.52 (2H, m), 3.94–4.02 (2H, m), 4.38–4.51 (1H, m), 7.38 (1H, s-like), 7.47 (2H, s-like).

(34) 5-Cyano-1-cyclohexyl-2,3-dihydro-1H-benzimidazol-2-one

NMR(DMSO-$d_6$, δ): 1.21–1.48 (3H, m), 1.60–1.76 (3H, m), 1.76–1.90 (2H, m), 2.00–2.18 (2H, m), 4.10–4.24 (1H, m), 7.36 (1H, s), 7.44 (1H, d, J=8 Hz), 7.50 (1H, d, J=8 Hz).

(35) 1-tert-Butyl-5-cyano-2,3-dihydro-1H-benzimidazol-2-one

NMR(DMSO-$d_6$, δ): 1.69 (9H, s), 7.30 (1H, d, J=2 Hz), 7.36 (1H, dd, J=8, 2 Hz), 7.57 (1H, d, J=8 Hz).

(36) 5-Cyano-1-cycloheptyl-2,3-dihydro-1H-benzimidazol-2-one

NMR(DMSO-$d_6$, δ): 1.65–1.91 (6H, m), 1.91–2.06 (4H, m), 2.28–2.50 (2H, m), 4.46–4.61 (1H, m), 7.57 (1H, s), 7.60–7.69 (2H, m).

(37) 1-((S)-2-Acetoxy-1-ethylethyl)-5-cyano-2,3-dihydro-1H-benzimidazol-2-one

NMR(CDCl$_3$, δ): 0.93 (3H, t, J=7.5 Hz), 1.85–2.04 (4H, m), 2.10–2.28 (1H, m), 4.40–4.62 (3H, m), 7.15 (1H, d, J=8 Hz), 7.37–7.45 (2H, m), 9.86 (1H, s).

(38) 1-((R)-2-Acetoxy-1-ethylethyl)-5-cyano-2,3-dihydro-1H-benzimidazol-2-one

NMR(CDCl$_3$, δ): 0.93 (3H, t, J=7.5 Hz), 1.85–2.03 (4H, m), 2.09–2.28 (1H, m), 4.41–4.63 (3H, m), 7.15 (1H, d, J=8 Hz), 7.38 (1H, d, J=2 Hz), 7.41 (1H, dd, J=8, 2 Hz), 9.61 (1H, s).

(39) 1-[1-(tert-Butoxycarbonyl)piperidin-4-yl]-5-cyano-2,3-dihydro-1H-benzimidazol-2-one NMR(CDCl$_3$, δ): 1.51 (9H, s), 1.78–1.90 (2H, m), 2.20–2.39 (2H, m), 2.78–2.95 (2H, m), 4.25–4.40 (2H, m), 4.40–4.54 (1H, m), 7.19 (1H, d, J=8 Hz), 7.35 (1H, d, J=2 Hz), 7.41 (1H, dd, J=8, 2 Hz)

MS m/z: 341(M$^+$–1).

(40) 5-Cyano-1-(t-3, t-4-isopropylidenedioxy-r-1-cyclohexyl)-2,3-dihydro-1H-benzimidazol-2-one NMR(DMSO-$d_6$, δ): 1.28 (3H, s), 1.48 (3H, s), 1.58–1.80 (2H, m), 1.86–2.12 (3H, m), 2.39–2.59 (1H, m), 4.14–4.26 (1H, m), 4.32–4.40 (1H, m), 4.40–4.58 (1H, m), 7.29–7.54 (3H, m), 11.35 (1H, s)

MS m/z: 312.2 (M$^+$–1).

(41) 5-Cyano-1-(c-3, c-4-isopropylidenedioxy-r-1-cyclohexyl)-2,3-dihydro-1H-benzimidazol-2-one NMR(DMSO-$d_6$, δ): 1.29 (3H, s), 1.44–1.60 (4H, m), 1.80–1.95 (2H, m), 2.10–2.36 (3H, m), 4.11–4.29 (3H, m), 7.32 (1H, d, J=8 Hz), 7.37 (1H, d, J=2 Hz), 7.50 (1H, dd, J=8, 2 Hz).

MS m/z: 312.2 (M$^+$–1).

(42) 3-((R)-2-Acetoxy-1-methylethyl)-6-cyano-2,3-dihydro-1H-imidazo[4,5-b]pyridin-2-one mp. 161–161.5° C.

NMR(DMSO-$d_6$, δ): 1.50(3H, d, J=7.0 Hz), 1.87(3H, s), 4.36(1H, dd, J=11.0, 5.0 Hz), 4.55(1H, dd, J=11.0, 9.0 Hz), 4.66–4.80(1H, m), 7.74(1H, d, J=2.0 Hz), 8.44(1H, d, J=2.0 Hz).

MS m/z: 259(M$^+$–1).

(43) 1-[trans-4-(N-tert-Butoxycarbonylamino)cyclohexyl]-5-trifluoromethyl-2,3-dihydro-1H-benzimidazol-2-one mp. 274–275° C.

NMR(DMSO-$d_6$, δ): 1.25–1.44(2H, m), 1.40(9H, s), 1.64–1.75(2H, m), 1.84–1.95(2H, m), 2.13–2.29(2H, m), 3.29–3.49(1H, m), 4.07–4.22(1H, m), 6.81(1H, d, J=7.5 Hz), 7.20(1H, s), 7.30(1H, d, J=8.5 Hz), 7.55(1H, d, J=8.5 Hz).

MS m/z: 398(M$^+$–1).

(44) 3-((S)-1-tert-Butoxycarbonylpyrrolidin-3-yl)-6-trifluoromethyl-2,3-dihydro-1H-imidazo[4,5-b]pyridin-2-one mp. 130–131.5° C.

NMR(DMSO-$d_6$, δ): 1.40(6H, s), 1.43(3H, s), 2.09–2.21 (1H, m), 2.53–2.73(1H, m), 3.27–3.41(1H, m), 3.51–3.66 (2H, m), 3.73–3.83(1H, m), 4.99–5.13(1H, m), 7.57(1H, s), 8.34(1H, s).

MS m/z: 373(M$^+$+1).

(45) A mixture of 3-amino-5-cyano-2-(trans-4-hydroxycyclohexylamino)pyridine (3.1 g) and 1,1'-carbonyldiimidazole (6.49 g) in acetonitrile (31 mL) was stirred at 50° C. under nitrogen atmosphere for 15 minutes. After adding 1N-NaOH(35 mL), the mixture was stirred at 60° C. for 1.5 hours. The reaction mixture was neutralized with concentrated hydrochloric acid to yield a precipitate. The resulting precipitate was collected by filtration and washed successively with water and aqueous ethanol to give 6-cyano-3-(trans-4-hydroxycyclohexyl)-2,3-dihydro-1H-imidazo[4,5-b]pyridin-2-one (1.93 g) as a brown solid.

mp. 274–275° C.

NMR(DMSO-$d_6$, δ): 1.22–1.39 (2H, m), 1.63–1.75 (2H, m), 1.88–1.99 (2H, m), 2.25–2.44 (2H, m), 3.42–3.55 (1H, m), 4.15–4.27 (1H, m), 4.68 (1H, d, J=4.5 Hz), 7.70 (1H, d, J=2.0 Hz), 8.42 (1H, d, J=2.0 Hz).

MS m/z: 257(M$^+$–1).

(46) 3-(Benzimidazol-5-yl)-6-cyano-2,3-dihydro-1H-imidazo[4,5-b]pyridin-2-one

NMR(DMSO-$d_6$, δ): 7.36(1H, d, J=8 Hz), 7.64–7.95(3H, m), 8.34(1H, s), 8.40(1H, s), 11.85(1H, br s), 12.66(1H, br s).

MS (ESI) m/z: 275(M$^+$–1).

(47) 3-(1H-Indol-5-yl)-6-cyano-2,3-dihydro-1H-imidazo[4,5-b]pyridin-2-one mp. 288–289° C.

NMR(DMSO-$d_6$, δ): 6.97(1H, d, J=3.5 Hz), 7.21(1H, d, J=2.0 Hz), 7.62(1H, dd, J=8.5, 2.0 Hz), 7.77(1H, d, J=3.5 Hz), 7.80(1H, m), 7.85(1H, d, J=2.0 Hz), 8.16(1H, d, J=8.5 Hz), 8.37(1H, d, J=2.0 Hz).

(48) 1-(Benzimidazol-5-yl)-5-cyano-2,3-dihydro-1H-benzimidazole-2-one

NMR(DMSO-$d_6$, δ): 7.03 (1H, d, J=8 Hz), 7.30 (1H, dd, J=8,2 Hz), 7.46 (1H, dd, J=8,2 Hz), 7.50 (1H, d), 7.69–7.81 (2H, m), 8.36 (1H, s)

MS (ES$^-$) m/z: 274.1 (M$^+$–1).

(49) 1-(3-Acetoxypropyl)-5-cyano-2,3-dihydro-1H-benzimidazole-2-one

NMR(CDCl$_3$, δ): 2.05 (3H, s), 2.13 (2H, m), 4.03 (2H, t, J=5 Hz), 4.14 (2H, t, J=5 Hz), 7.06 (1H, d, J=8 Hz), 7.39 (1H, d, J=2 Hz), 7.44 (1H, dd, J=8, 2 Hz), 9.77 (1H, s).

MS (ES-) m/e 258.1 (M–H).

(50) 1-[2-(N,N-Dimethylamino)ethyl]-5-cyano-2,3-dihydro-1H-benzimidazole-2-one

NMR(DMSO-$d_6$, δ): 2.16 (6H, s), 2.53–2.58 (2H, m), 3.92 (2H, t, J=7 Hz), 7.33 (1H, d, J=8 Hz), 7.40 (1H, d, J=2 Hz), 7.50 (1H, dd, J=8,2 Hz),

MS (ES$^+$) m/z: 231.4 (M$^+$+1).

PREPARATION 26

To a solution of 3-amino-4-(trans-4-hydroxycyclohexylamino)benzotrifluoride (300 mg) in N,N-dimethylformamide (3 mL) was added 1,1'-thiocarbonyldiimidazole (234 mg), and the mixture was stirred at room temperature under nitrogen atmosphere for 15 hours. Water was added to the mixture, and the resulting precipitate was collected by filtration. The obtained solid was washed successively with water and diethyl ether to give 1-(trans-4-hydroxycyclohexyl)-5-trifluoromethyl-2,3-dihydro-1H-benzimidazol-2-thione (242.8 mg) as a pale brown solid.

mp. 280–281° C.

NMR(DMSO-d$_6$, δ): 1.22–1.45(2H, m), 1.63–1.75(2H, m), 1.92–2.05(2H, m), 2.16–2.37(2H, m), 3.60–3.75(1H, m), 4.72(1H, d, J=4.5 Hz), 4.97–5.12(1H, m), 7.41(1H, s), 7.46(1H, d, J=8.5 Hz), 7.86(1H, d, J=8.5 Hz).

MS m/z: 315(M$^+$−1).

PREPARATION 27

5-Cyano-1-(trans-4-hydroxycyclohexyl)-2,3-dihydro-1H-benzimidazol-2-thione was prepared in a manner similar to Preparation 26.

mp. 278.5–280° C.

NMR(DMSO-d$_6$, δ): 1.25–1.42(2H, m), 1.61–1.73(2H, m), 1.93–2.04(2H, m), 2.15–2.34(2H, m), 3.60–3.75(1H, m), 4.70(1H, d, J=5.5 Hz), 4.96–5.11(1H, m), 7.57(1H, dd, J=8.5, 2.0 Hz), 7.58(1H, d, J=2.0 Hz), 7.84(1H, d, J=8.5 Hz).

MS m/z: 272(M$^+$−1).

PREPARATION 28

To a solution of 3-amino-4-cyclopentylamino-1-nitrobenzene (445 mg) and 1,8-diazabicyclo[5.4.0]undec-7-ene (0.6 mL) in 1,2-dichloroethane (5 mL) was added triphosgene (358 mg) at 0° C., and the mixture was stirred at room temperature under nitrogen atmosphere for 20 minutes. The resulting mixture was diluted with chloroform and washed successively with water(twice) and brine. The organic layer was dried over magnesium sulfate and evaporated in vacuo. The residue was subjected to a silica gel column chromatography eluting with a mixture of n-hexane and ethyl acetate (3:1). The obtained substance was triturated with diisopropyl ether to give 1-cyclopentyl-5-nitro-2,3-dihydro-1H-benzimidazol-2-one (249.8 mg) as an off-white solid.

mp. 252–252.5° C.

NMR(DMSO-d$_6$, δ): 1.57–1.77(2H, m), 1.81–2.11(6H, m), 4.78(1H, quint., J=8.5 Hz), 7.36(1H, d, J=9.0 Hz), 7.75(1H, d, J=2.0 Hz), 7.99(1H, dd, J=9.0, 2.0 Hz).

MS m/z: 246(M$^+$−1).

PREPARATION 29

The following compounds described in (1) to (5) were obtained in a manner similar to Preparation 28.

(1) 5-Cyano-1-(trans-4-hydroxycyclohexyl)-2,3-dihydro-1H-benzimidazol-2-one mp. 258–260° C.

NMR(DMSO-d$_6$, δ): 1.25–1.43(2H, m), 1.59–1.77(2H, m), 1.87–1.98(2H, m), 2.09–2.28(2H, m), 3.46–3.63(1H, m), 4.10–4.25(1H, m), 7.35(1H, d, J=1.0 Hz), 7.43(1H, dd, J=8.0, 1.0 Hz), 7.48(1H, d, J=8.0 Hz).

MS m/z: 256(M$^+$−1).

(2) 1-((R)-2-Hydroxy-1-methylethyl)-5-trifluoromethyl-2,3-dihydro-1H-benzimidazol-2-one mp. 197–198° C.

NMR(DMSO-d$_6$, δ): 1.38(3H, d, J=7.0 Hz), 3.56–3.67 (1H, m), 3.80–3.91(1H, m), 4.36–4.50(1H, m), 4.93(1H, t, J=4.5 Hz), 7.20(1H, d, J=1.5 Hz), 7.31(1H, dd, J=8.5, 1.5 Hz), 7.40(1H, d, J=8.5 Hz), 11.19(1H, s).

MS m/z: 259(M$^+$−1).

(3) 1-(trans-4-Formamidocyclohexyl)-5-trifluoromethyl-2,3-dihydro-1H-benzimidazol-2-one mp. 304–306° C.

NMR(DMSO-d$_6$, δ): 1.32–1.54(2H, m), 1.66–1.78(2H, m), 1.84–2.00(2H, m), 2.15–2.35(2H, m), 3.69–3.89(1H, m), 4.14–4.28(1H, m), 7.21(1H, s), 7.32(1H, d, J=8.5 Hz), 7.59(1H, d, J=8.5 Hz), 7.97(1H, s), 8.04 (1H, d, J=7.5 Hz), 11.25(1H, s).

MS m/z: 326(M$^+$−1).

(4) 5-Cyano-1-((R)-2-hydroxy-1-methylethyl)-2,3-dihydro-1H-benzimidazol-2-one

NMR(DMSO-d$_6$, δ): 1.37 (3H, d, J=7.5 Hz), 3.55–3.66 (1H, m), 3.79–3.91 (1H, m), 4.36–4.50 (1H, m), 4.94 (1H, t, J=5 Hz), 7.30–7.46 (3H, m).

(5) 5-Cyano-1-((S)-2-hydroxy-1-methylethyl)-2,3-dihydro-1H-benzimidazol-2-one

NMR(DMSO-d$_6$, δ): 1.37 (3H, d, J=7.5 Hz), 3.56–3.66 (1H, m), 3.79–3.91 (1H, m), 4.35–4.53 (1H, m), 4.94 (1H, t, J=5 Hz), 7.32–7.46 (3H, m).

PREPARATION 30

A mixture of 2-methoxyphenethyl alcohol (500 mg) and carbon tetrabromide (1.53 g) in anhydrous dichloromethane (10 mL) was stirred at 0° C. under a nitrogen atmosphere. After adding triphenylphosphine (1.03 g) portionwise, the reaction mixture was stirred for an hour under the same condition. The reaction mixture was evaporated in vacuo and the residue was subjected to a silica gel column chromatography eluting with n-hexane only and then a mixture of n-hexane and ethyl acetate (40:1 to 20:1) to give 2-methoxyphenethyl bromide (661 mg) as an oil.

NMR(CDCl$_3$, δ): 3.17 (2H, t, J=7.5 Hz), 3.58 (2H, t, J=7.5 Hz), 3.83 (3H, s), 6.80–6.99 (2H, m), 7.15 (1H, dd, J=8, 2 Hz), 7.20–7.34 (1H, m).

PREPARATION 31

To a solution of 3-bromo-4-methoxybenzaldehyde (4.98 g) in ethanol (50 mL) and tetrahydrofuran (10 mL) was added sodium borohydride (1.31 g) under ice-water cooling. The mixture was stirred at 0° C. for 2 hours. After evaporation of the solvent, the residue was partitioned between ethyl acetate and water. The separated organic layer was washed successively with water and brine, and dried over magnesium sulfate. The organic layer was evaporated in vacuo to give 3-bromo-4-methoxybenzyl alcohol as a colorless oil (4.98 g).

NMR(CDCl$_3$, δ): 1.73 (1H, t, J=7 Hz), 3.90 (3H, s), 4.60 (2H, d, J=7 Hz), 6.88 (1H, d, J=8 Hz), 7.25 (1H, dd, J=4, 8 Hz), 7.56 (1H, d, J=4 Hz).

PREPARATION 32

The following compounds described in (1) and (2) were obtained in a manner similar to Preparation 31.

(1) 3-Fluoro-4-methoxybenzyl alcohol

NMR(CDCl$_3$, δ): 1.73 (1H, t, J=7 Hz), 3.88 (3H, s), 4.62 (2H, d, J=7 Hz), 6.88–6.97 (1H, m), 7.00–7.25 (2H, m).

(2) 4-Methoxy-3-methylbenzyl alcohol

NMR(CDCl$_3$, δ): 1.59 (1H, t, J=7 Hz), 2.22 (3H, s), 3.83 (3H, s), 4.58 (2H, d, J=7 Hz), 6.79 (1H, d, J=8 Hz), 7.13 (2H, m).

PREPARATION 33

A mixture of 3-cyclohexene-1-carboxylic acid (1.8 g), triethylamine (2.2 mL) and diphenylphosphoryl azide (3.93 g) in benzene (40 mL) was refluxed for 2 hours. After adding benzyl alcohol (1.54 g), the mixture was refluxed for 10 hours. The mixture was evaporated in vacuo and the obtained residue was diluted with ethyl acetate. The organic layer was washed successively with 1N hydrochloric acid, an aqueous saturated sodium hydrogen carbonate solution and brine. The obtained organic layer was dried over sodium sulfate and evaporated in vacuo. The residues was recrystallized from hexane-diethyl ether to give benzyl N-(3-cyclohexene-1-yl)carbamate (1.72 g) as a solid.

NMR(CDCl$_3$, δ): 1.58 (1H, m), 1.82–1.95 (2H, m), 2.05–2.36 (2H, m), 2.40 (1H, m), 3.88 (1H, m), 4.78 (1H, m), 5.55–5.72 (2H, m), 7.27–7.39 (5H, m).

PREPARATION 34

To a solution of benzyl N-(3-cyclohexene-1-yl)carbamate (1.7 g) in a mixture of tetrahydrofuran (40 mL) and water (2 mL) was added N-methyl morpholine N-oxide (1.29 g) and osmium tetroxide (5 mL of 4% solution in water). The mixture was stirred at ambient temperature for 30 minutes. The resulting mixture was evaporated in vacuo and the obtained residue was diluted with ethyl acetate. The organic layer was washed successively with 1N hydrochloric acid, an aqueous saturated sodium hydrogen carbonate solution and brine. The obtained organic layer was dried over sodium sulfate and evaporated in vacuo. The residue was recrystallized from ethyl acetate to give (1β,3α,4α)-benzyl N-(3,4-dihydroxy-1-cyclohexyl)carbamate (374 mg) as a solid.

NMR(DMSO-d$_6$, δ): 1.15 (1H, m), 1.34 (1H, m), 1.44–1.83 (4H, m), 3.35 (1H, m), 3.64 (1H, m), 3.74 (1H, m), 4.28 (1H, d, J=3 Hz), 4.34 (1H, d, J=5 Hz), 4.99 (2H, s), 7.08 (1H, d, J=7 Hz), 7.26–7.41 (5H, m).

The residual solution after removing the crystals was evaporated. The residue was subjected to a silica gel column chromatography eluting with a mixture of chloroform and methanol (9:1). The obtained product was triturated with diethyl ether to give (1α,3α,4α)-benzyl N-(3,4-dihydroxy-1-cyclohexyl)carbamate (565 mg) as a solid.

NMR(DMSO-d$_6$, δ): 1.24–1.69 (6H, m), 3.23–3.46 (2H, m), 3.63 (1H, m), 4.20 (1H, d, J=2 Hz), 4.50 (1H, d, J=5 Hz), 4.99 (2H, s), 7.17 (1H, d, J=7H), 7.26–7.42 (5H, m).

PREPARATION 35

A mixture of (1β,3α,4α)-benzyl N-(3,4-dihydroxy-1-cyclohexyl)carbamate (173 mg) and 10% palladium on activated carbon (34 mg) in ethanol (6 mL) was stirred at ambient temperature under hydrogen atmosphere (3 atm) for an hour. The catalyst was removed by filtration, and the filtrate was evaporated in vacuo. The residue was recrystallized from ethanol-diethyl ether to give (1β,3α,4α)-1-amino-3,4-cyclohexanediol (73 mg) as a solid.

NMR(CDCl$_3$, δ): 1.06–1.44 (2H, m), 1.65–1.66 (2H, m), 1.84 (1H, m), 2.04 (1H, m), 3.07 (1H, m), 3.58 (1H, m), 3.96 (1H, m).

PREPARATION 36

(1α,3α,4α)-Amino-3,4-cyclohexanediol was obtained in a manner similar to Preparation 35.

NMR(CDCl$_3$, δ): 1.42–1.78 (7H, m), 1.91 (1H, m), 2.88 (1H, m), 3.68 (1H, m), 3.75 (1H, m).

PREPARATION 37

A mixture of methyl 3-cyano-4-methoxybenzoate (5g), tetrahydrofuran (25 mL) and sodium borohydride (1.98 g) was heated at 45° C. The mixture was dropwise added with methanol (6.36 mL) at 45–55° C. over 15 minutes and then refluxed for 3.5 hours. After cooling to 0° C., the mixture was added with an aqueous saturated ammonium chloride solution at the same temperature. The mixture was stirred at room temperature for an hour, and extracted with ethyl acetate. The organic layer was washed successively with water, an aqueous saturated sodium bicarbonate solution and brine. The organic layer was dried over magnesium sulfate and evaporated in vacuo. The residual solid was triturated with diisopropyl ether to give 3-cyano-4-methoxybenzyl alcohol (3.75 g) as a pale brown solid.

mp. 75–76° C.

NMR(DMSO-d$_6$, δ): 3.90(3H, s), 4.45(2H, d, J=5.5 Hz), 5.28(1H, t, J=5.5 Hz), 7.21(1H, d, J=9.5 Hz), 7.60(1H, d, J=9.5 Hz), 7.62(1H, s).

PREPARATION 38

To a solution of 3-cyano-4-methoxybenzyl alcohol (500 mg) in dichloromethane (5 mL) was added phosphorus tribromide (0.146 mL) under ice-water cooling. The mixture was stirred at 0° C. for 3 hours and partitioned between chloroform and water. The separated organic layer was washed successively with water, an aqueous saturated sodium bicarbonate solution and brine. The organic layer was dried over magnesium sulfate and evaporated in vacuo. The residual solid was triturated with diisopropyl ether to give 3-cyano-4-methoxybenzyl bromide as an off-white solid (456.3 mg).

mp. 127–128° C.

NMR(DMSO-d$_6$, δ): 3.93(3H, s), 4.71(2H, s), 7.26(1H, d, J=8.5 Hz), 7.76(1H, dd, J=8.5, 2.5 Hz), 7.84(1H, d, J=2.5 Hz).

PREPARATION 39

The following compounds described in (1) to (3) were obtained in a manner similar to Preparation 38.
(1) 3-Bromo-4-methoxybenzyl bromide NMR(CDCl$_3$, δ): 3.90 (3H, s), 4.44 (2H, s), 6.85 (1H, d, J=8 Hz), 7.30 (1H, dd, J=4, 8 Hz), 7.59 (1H, d, J=4 Hz).
(2) 3-Fluoro-4-methoxybenzyl bromide NMR(CDCl$_3$, δ): 3.89 (3H, s), 4.45 (2H, s), 6.91 (1H, t, J=8 Hz), 7.07–7.15 (2H, m).
(3) 4-Methyl-3-methoxybenzyl bromide NMR(CDCl$_3$, δ): 2.20 (3H, s), 3.83 (3H, s), 4.49 (2H, s), 6.77 (1H, d, J=8 Hz), 7.18 (2H, m).

PREPARATION 40

A mixture of 6-hydroxy-5-nitronicotinamide (343 g), phosphorus oxychloride (40 ml) and phosphorus pentachloride (1287 g) was heated at 130° C. for 3.5 hours. After cooling to ambient temperature, the mixture was concentrated in vacuo. The residue was partitioned between ethyl acetate and an aqueous saturated sodium bicarbonate solution. The organic layer was dried over magnesium sulfate and evaporated to afford 6-chloro-5-nitronicotinonitrile (374 g) as an oil.

NMR(DMSO-d$_6$, δ): 9.22(1H, d, J=2.0 Hz), 9.25(1H, d, J=2.0 Hz).

PREPARATION 41

To a solution of 4-methoxy-3-nitrotoluene (5.02 g) and N-bromosuccinimide (5.51 g) in dichloromethane (50 mL) was added 2,2'-azobis(4-methoxy-2,4-dimethylvaleronitrile) (463 mg). The mixture was heated under reflux for 8 hours. The solution was washed with water and brine, dried over magnesium sulfate and evaporated in vacuo. The residue was triturated with n-hexaneethyl acetate (20:1) to give 4-methoxy-3-nitrobenzyl bromide as a pale yellow powder (5.78 g).

NMR(CDCl$_3$, δ): 3.98 (3H, s), 4.47 (2H, s), 7.07 (1H, d, J=8 Hz), 7.58 (1H, dd, J=2 Hz, 8 Hz), 7.90 (1H, d, J=2 Hz).

PREPARATION 42

To a solution of 4-hydroxybenzaldehyde (100 g) in chloroform (1 L) was added N-chlorosuccinimide (120 g) at ambient temperature and the mixture was stirred at 50° C. for 18 hours. After evaporation of the solvent, the residue was partitioned between ethyl acetate and water. The organic layer was washed with water and brine, dried over magnesium sulfate, and evaporated in vacuo. The crude crystals was washed with diisopropyl ether and recrystallized from a mixture of ethyl acetate and n-hexane to obtain 3-chloro-4-hydroxybenzaldehyde (85.8 g) as colorless crystals.

NMR(CDCl$_3$, δ) 6.16 (1H, br), 7.16 (1H, d, J=8 Hz), 7.74 (1H, d, J=8 Hz), 7.89 (1H, s), 9.83 (1H, s).

PREPARATION 43

To a solution of 3-chloro-4-hydroxybenzaldehyde (153 g) in dimethylformamide (500 ml) was added potassium carbonate (203 g) under ice-cooling, followed by iodomethane (91.3 ml). After stirring at ambient temperature for 2 hours, the mixture was partitioned between ethyl acetate and water. The aqueous layer was extracted with ethyl acetate. The combined organic layer were washed with water and brine, dried over magnesium sulfate and evaporated in vacuo. The oily residue was triturated with n-hexane to obtain 3-chloro-4-methoxybenzaldehyde (156 g) as a white powder.

NMR(CDCl$_3$, δ): 4.00 (3H, s), 7.05 (1H, d, J=8 Hz), 7.78 (1H, dd, J=2 Hz, 8 Hz), 7.92 (1H, d, J=2 Hz), 9.86 (s, 1H).

PREPARATION 44

To a solution of 3-chloro-4-methoxybenzaldehyde (156 g) in a mixture of ethanol (750 ml) and tetrahydrofuran (500 ml) was added sodium borohydride (25 g) under ice-cooling. After stirring at ambient temperature for 2 hours, the mixture was partitioned between ethyl acetate and water. The organic layer was washed with water, 1N-hydrochloric acid, water, aqueous sodium bicarbonate and brine, successively, and dried over magnesium sulfate. Evaporation of the solvent gave 3-chloro-4-methoxybenzyl alcohol (164 g) as a yellow oil.

NMR(CDCl$_3$, δ): 1.70 (1H, t, J=7 Hz), 3.90 (3H, s), 4.60 (2H, d, J=7 Hz), 6.90 (1H, d, J=8 Hz), 7.22 (1H, dd, J=4 Hz, 8 Hz), 7.39 (1H, d, J=4 Hz).

PREPARATION 45

To a solution of 3-chloro-4-methoxybenzyl alcohol (164 g) in dichloromethane (800 ml) was added phosphorus tribromide (45.1 ml) under ice-cooing and the mixture was stirred at ambient temperature for an hour followed by adding water to the mixture. The separated aqueous layer was extracted with dichloromethane. The combined organic layers were washed with an aqueous saturated sodium bicarbonate solution and brine, dried over magnesium sulfate, and evaporated in vacuo. The oily residue was triturated with n-hexane to obtain 3-chloro-4-methoxybenzyl bromide (200 g) as a white powder.

NMR(CDCl$_3$, δ): 3.92 (3H, s), 4.45 (2H, s), 6.89 (1H, d, J=8 Hz), 7.27 (1H, d, J=8 Hz), 7.43 (1H, s).

PREPARATION 46

Fuming nitric acid(10.4 ml) was added dropwise to a mixture of 6-hydroxynicotinic acid (15 g) and concentrated sulfuric acid(45 ml) at 0° C. The reaction mixture was slowly heated to 45° C. and maintained at the same temperature for 3 hours. The mixture was poured into ice-water, and the resultant precipitate was collected by suction filtration, washed with water, and air-dried to give 6-hydroxy-5-nitronicotinic acid (8.63 g) as a pale yellow solid.

mp. 277–278° C.

NMR(DMSO-d$_6$, δ): 8.37(1H, d, J=2.5 Hz), 8.65(1H, d, J=2.5 Hz).

MS m/z: 183(M$^+$-1).

PREPARATION 47

6-Hydroxy-5-nitronicotinic acid (7.58 g) and thionyl chloride (48.1 ml) were combined under nitrogen atmosphere, and the mixture was refluxed for 2 hours. After cooling to ambient temperature, the reaction mixture was concentrated in vacuo. The residue was dissolved in dichloromethane (10 ml), and the solution was added dropwise to the mixture of ammonium hydroxide (28% in water) (20 ml) and dichloromethane (10 ml) at 0° C. with stirring. The precipitate was collected by suction filtration and washed with water to give 6-Hydroxy-5-nitronicotinamide (4.97 g) as a yellow solid.

mp. 280–281° C.

NMR(DMSO-d$_6$, δ): 6.98(1H, br), 7.67(1H, br), 8.51(1 H, d, J=2.5 Hz), 8.58(1H, d, J=2.5 Hz).

MS m/z: 182(M$^+$-1).

PREPARATION 48

To a solution of 6-chloro-5-nitronicotinonitrile (3.5 g) in N,N-dimethylformamide (35 ml) was added trans-4-aminocyclohexanol (4.39 g) at 0° C. The mixture was stirred at ambient temperature for 45 minutes under nitrogen atmosphere, and diluted with ethyl acetate. The resultant organic solution was washed with water (3 times) and brine, dried over magnesium sulfate, and concentrated in vacuo. The residual solid was washed with diethyl ether to give 6-(trans-4-hydroxycyclohexylamino)-5-nitronicotinonitrile (3.38 g) as a yellow solid.

mp. 157–158° C.

NMR(DMSO-d$_6$, δ): 1.20–1.35(2H, m), 1.45–1.61(2H, m), 1.80–1.95(4H, m), 3.39–3.50(1H, m), 4.08–4.23(1H, m), 4.63(1H, d, J=4.0 Hz), 8.47(1H, d, J=8.0 Hz), 8.83(1H, d, J=2.0 Hz), 8.88(1H, d, J=2.0 Hz).

MS m/z: 261(M$^+$-1).

PREPARATION 49

6-(trans-4-Hydroxycyclohexylamino)-5-nitronicotinonitrile (3.35 g) was dissolved in a mixture of methanol (17 ml) and 1,4-dioxane (17 ml), and 10% palladium on carbon (383 mg) was added to the solution under nitrogen atmosphere. The mixture was shaken at ambient temperature for 3 hours under hydrogen atmosphere (3 atm). The reaction mixture was filtered through a celite pad, and the filtrate was concentrated in vacuo to give 5-amino-6-(trans-4-hydroxycyclohexylamino)nicotinonitrile (3.15 g) as a brown amorphous.

NMR(DMSO-d$_6$, δ): 1.16–1.34 (4H, m), 1.77–1.98 (4H, m), 3.36–3.49 (1H, m), 3.78–3.92 (1H, m), 4.57 (1H, d, J=4.5 Hz), 5.20 (2H, s), 6.22 (1H, d, J=7.0 Hz), 6.77 (1H, d, J=2.0 Hz), 7.78 (1H, d, J=2.0 Hz).

MS m/z: 231(M$^+$-1)

EXAMPLE 1

To a solution of 1-(trans-4-hydroxycyclohexyl)-5-trifluoromethyl-2,3-dihydro-1H-benzimidazol-2-one (200 mg) in anhydrous N,N-dimethylformamide (2 mL) was added portionwise sodium hydride (29.3 mg, 60% dispersion in mineral oil) at 5° C. under nitrogen atmosphere, and the mixture was stirred at room temperature for 30 minutes. After adding 3,4-dimethoxybenzylbromide (154 mg), the mixture was stirred at room temperature for 2 hours. The mixture was partitioned between ethyl acetate and water. The separated organic layer was washed successively with 1 N-hydrochloric acid, water, an aqueous saturated sodium hydrogencarbonate solution and brine. The organic layer was dried over magnesium sulfate and evaporated in vacuo. The residue was subjected to a preparative silica gel column chromatography eluting with 5% methanol in chloroform. The obtained amorphous was recrystallized from diethyl ether to give 3-(3,4-dimethoxybenzyl)-1-(trans-4-hydroxycyclohexyl)-5-trifluoromethyl-2,3-dihydro-1H-benzimidazol-2-one (217.9 mg) as a colorless solid.

mp. 108–110° C.

NMR(DMSO-$d_6$, δ): 1.28–1.47(2H, m), 1.66–1.79(2H, m), 1.90–2.02(2H, m), 2.15–2.33(2H, m), 3.50–3.65(1H, m), 3.69(3H, s), 3.70(3H, s), 4.20–4.34(1H, m), 4.69(1H, d, J=4.5 Hz), 5.04(2H, s), 6.82(1H, d, J=8.0 Hz), 6.89(1H, d, J=8.0 Hz), 7.06(1H, s), 7.36(1H, d, J=8.0 Hz), 7.55(1H, d, J=8.0 Hz), 7.56(1H, s).

EXAMPLE 2

The following compounds described in (1) to (112) were obtained in a manner similar to Example 1.

(1) 1-Cyclopentyl-3-(3,4-dimethoxybenzyl)-5-nitro-2,3-dihydro-1H-benzimidazol-2-one mp. 121–123° C.

NMR(DMSO-$d_6$, δ): 1.59–1.75(2H, m), 1.85–2.12(6H, m), 3.70(3H, s), 3.73(3H, s), 4.86(1H, quint., J=8.5 Hz), 5.09(2H, s), 6.83(1H, dd, J=8.5, 2.0 Hz), 6.90(1H, d, J=8.5 Hz), 7.07(1H, d, J=2.0 Hz), 7.44(1H, d, J=8.5 Hz), 8.02(1H, dd, J=8.5, 2.0 Hz), 8.07(1H, d, J=2.0 Hz).

(2) 3-(4-Chloro-3-methoxybenzyl)-1-cyclopentyl-5-nitro-2,3-dihydro-1H-benzimidazol-2-one mp. 170–171.5° C.

NMR(DMSO-$d_6$, δ): 1.59–1.77(2H, m), 1.85–2.15(6H, m), 3.84(3H, s), 4.86(1H, quint., J=8.0 Hz), 5.17(2H, s), 6.83(1H, d, J=8.0 Hz), 7.28(1H, s), 7.37(1H, d, J=8.0 Hz), 7.46(1H, d, J=8.0 Hz), 8.05(1H, dd, J=8.0, 1.5 Hz), 8.10(1H, d, J=1.5 Hz).

(3) 3-(3,4-Dimethoxybenzyl)-1-(trans-4-hydroxycyclohexyl)-5-nitro-2,3-dihydro-1H-benzimidazol-2-one mp. 175–176° C.

NMR(DMSO-$d_6$, δ): 1.30–1.47(2H, m), 1.68–1.79(2H, m), 1.91–2.01(2H, m), 2.15–2.33(2H, m), 3.51–3.64(1H, m), 3.70(3H, s), 3.72(3H, s), 4.23–4.35(1H, m), 4.71(1H, d, J=4.5 Hz), 5.08(2H, s), 6.83(1H, dd, J=8.5, 2.5 Hz), 6.90(1H, d, J=8.5 Hz), 7.05(1H, d, J=2.5 Hz), 7.60(1H, d, J=9.0 Hz), 7.99(1H, dd, J=9.0, 2.0 Hz), 8.06(1H, d, J=2.0 Hz).

(4) 3-(3,4-Dimethoxybenzyl)-1-(trans-4-hydroxycyclohexyl)-5-trifluoromethyl-2,3-dihydro-1H-benzimidazol-2-thione NMR(DMSO-$d_6$, δ): 1.28–1.45(2H, m), 1.65–1.75(2H, m), 1.90–2.00(2H, m), 2.15–2.33(2H, m), 3.55–3.74(1H, m), 3.69(3H, s), 3.71(3H, s), 4.19–4.33(1H, m), 4.56(1H, s), 4.73(1H, d, J=4.5 Hz), 6.88(1H, d, J=8.0 Hz), 6.99(1H, dd, J=8.0, 1.5 Hz), 7.08(1H, d, J=1.5 Hz), 7.45(1H, dd, J=8.5, 1.5 Hz), 7.91(1H, d, J=8.5 Hz), 7.93(1H, d, J=1.5 Hz).

MS m/z: 467($M^+$+1).

(5) 5-Cyano-3-(3,4-dimethoxybenzyl)-1-(trans-4-hydroxycyclohexyl)-2,3-dihydro-1H-benzimidazol-2-one mp. 209–210° C.

NMR(DMSO-$d_6$, δ): 1.26–1.47(2H, m), 1.65–1.77(2H, m), 1.86–2.01(2H, m), 2.13–2.32(2H, m), 3.50–3.65(1H, m), 3.70(3H, s), 3.72(3H, s), 4.20–4.34(1H, m), 4.69(1H, d, J=4.5 Hz), 4.98(2H, s), 6.86(1H, d, J=8.0 Hz), 6.90(1H, d, J=8.0 Hz), 7.04(1H, s), 7.49(1H, d, J=8.0 Hz), 7.57(1H, d, J=8.0 Hz), 7.72(1H, s).

(6) 3-(3,4-Dimethoxybenzyl)-1-((R)-2-hydroxy-1-methylethyl)-5-trifluoromethyl-2,3-dihydro-1H-benzimidazol-2-one NMR(DMSO-$d_6$, δ): 1.42(3H, d, J=7.5 Hz), 3.57–3.73(1H, m), 3.70(6H, s), 3.82–3.96(1H, m), 4.45–4.61(1H, m), 4.95(1H, t, J=4.5 Hz), 5.05(2H, s), 6.84(1H, d, J=8.5 Hz), 6.89(1H, d, J=8.5 Hz), 7.05(1H, s), 7.35(1H, d, J=8.5 Hz), 7.46(1H, d, J=8.5 Hz), 7.52(1H, s).

(7) 5-Acetyl-3-(3,4-dimethoxybenzyl)-1-(trans-4-hydroxycyclohexyl)-2,3-dihydro-1H-benzimidazol-2-one mp. 169–170° C.

NMR(DMSO-$d_6$, δ): 1.30–1.45(2H, m), 1.65–1.77(2H, m), 1.90–2.00(2H, m), 2.15–2.33(2H, m), 2.53(3H, s), 3.52–3.64(1H, m), 3.69(3H, s), 3.71(3H, s), 4.20–4.32(1H, m), 4.69(1H, d, J=4.0 Hz), 5.03(2H, s), 7.78(1H, dd, J=8.0, 2.0 Hz), 6.88(1H, d, J=8.0 Hz), 7.04(1H, d, J=2.0 Hz), 7.47(1H, d, J=8.0 Hz), 7.69(1H, d, J=1.5 Hz), 7.71(1H, dd, J=8.0, 1.5 Hz).

(8) 3-(3,4-Dimethoxybenzyl)-1-(trans-4-formamidocyclohexyl)-5-trifluoromethyl-2,3-dihydro-1H-benzimidazol-2-one mp. 158–160.5° C.

NMR(DMSO-$d_6$, δ): 1.32–1.52(2H, m), 1.70–1.83(2H, m), 1.85–2.02(2H, m), 2.20–2.40(2H, m), 3.69(3H, s), 3.71 (3H, s), 3.75–3.89(1H, m), 4.22–4.38(1H, m), 5.05(2H, s), 6.83(1H, d, J=7.5 Hz), 6.89(1H, d, J=7.5 Hz), 7.07(1H, s), 7.36(1H, d, J=7.5 Hz), 7.56(1H, s), 7.65(1H, d, J=7.5 Hz), 7.98(1H, s), 8.05(1H, d, J=7.5 Hz).

MS m/z: 478($M^+$+1).

(9) 5-Chloro-3-(3,4-dimethoxybenzyl)-1-(trans-4-hydroxycyclohexyl)-2,3-dihydro-1H-benzimidazol-2-one mp. 166–167° C.

NMR(DMSO-$d_6$, δ): 1.27–1.44(2H, m), 1.62–1.73(2H, m), 1.87–1.99(2H, m), 2.11–2.29(2H, m), 3.49–3.63(1H, m), 3.70(3H, s), 3.71(3H, s), 4.12–4.25(1H, m), 4.67(1H, d, J=4.5 Hz), 4.95(2H, s), 6.81(1H, dd, J=8.5, 2.0 Hz), 6.89(1H, d, J=8.5 Hz), 7.02(1H, d, J=2.0 Hz), 7.04(1H, dd, J=8.5, 2.0 Hz), 7.28(1H, d, J=2.0 Hz), 7.37(1H, d, J=8.5 Hz).

(10) 3-(3,4-Dimethoxybenzyl)-1-(trans-4-hydroxycyclohexyl)-5-methoxycarbonyl-2,3-dihydro-1H-benzimidazol-2-one mp. 148–149.5° C.

NMR(DMSO-$d_6$, δ): 1.27–1.45(2H, m), 1.66–1.77(2H, m), 1.87–2.01(2H, m), 2.15–2.32(2H, m), 3.49–3.64(1H, m), 3.69(3H, s), 3.72(3H, s), 3.81(3H, s), 4.17–4.33(1H, m), 4.67(1H, d, J=4.5 Hz), 5.03(2H, s), 6.73(1H, dd, J=8.5, 2.0 Hz), 6.88(1H, d, J=8.5 Hz), 7.01(1H, d, J=2.0 Hz), 7.48(1H, d, J=8.5 Hz), 7.65(1H, d, J=2.0 Hz), 7.69(1H, dd, J=8.5, 2.0 Hz).

(11) 3-(3,4-Dimethoxybenzyl)-1-(trans-4-hydroxycyclohexyl)-5-methoxy-2,3-dihydro-1H-benzimidazol-2-one mp. 176–177° C.

NMR(DMSO-$d_6$, δ): 1.27–1.43(2H, m), 1.60–1.72(2H, m), 1.87–1.99(2H, m), 2.11–2.30(2H, m), 3.50–3.62(1H, m), 3.70(9H, s), 4.09–4.22(1H, m), 4.66(1H, d, J=4.5 Hz), 4.91(2H, s), 6.57(1H, dd, J=8.5, 2.0 Hz), 6.79(1H, d, J=2.0 Hz), 6.81(1H, dd, J=8.5, 2.0 Hz), 6.87(1H, d, J=8.5 Hz), 7.02(1H, d, J=2.0 Hz), 7.21(1H, d, J=8.5 Hz).

MS m/z: 413($M^+$+1).

(12) 3-(trans-4-Acetoxycyclohexyl)-1-(3,4-dimethoxybenzyl)-6-trifluoromethyl-2,3-dihydro-1H-imidazo[4,5-b]pyridin-2-one mp. 130–133° C.

NMR(DMSO-d$_6$, δ): 1.46–1.63(2H, m), 1.76–1.89(2H, m), 1.95–2.10(2H, m), 2.02(3H, s), 2.40–2.54(2H, m), 3.70 (3H, s), 3.71(3H, s), 4.34–4.48(1H, m), 4.60–4.74(1H, m), 5.05(2H, s), 6.87(1H, d, J=8.0 Hz), 6.90(1H, d, J=8.0 Hz), 7.08(1H, s), 7.94(1H, s), 8.39(1H, s).

MS m/z: 494(M$^+$+1).

(13) 3-Cyclopentyl-1-(3,4-dimethoxybenzyl)-6-trifluoromethyl-2,3-dihydro-1H-imidazo[4,5-b]pyridin-2-one mp. 115–116° C.

NMR(DMSO-d$_6$, δ): 1.58–1.71(2H, m), 1.85–2.00(4H, m), 2.12–2.27(2H, m), 3.70(3H, s), 3.72(3H, s), 4.81–4.94 (1H, m), 5.05(2H, s), 6.86(1H, dd, J=8.5, 2.5 Hz), 6.89(1H, d, J=8.5 Hz), 7.09(1H, d, J=2.5 Hz), 7.94(1H, d, J=2.5 Hz), 8.38(1H, d, J=2.5 Hz).

(14) 1-(trans-2-Acetoxycyclopentyl)-3-(3,4-dimethoxybenzyl)-5-trifluoromethyl-2,3-dihydro-1H-benzimidazol-2-one NMR(DMSO-d$_6$, δ): 1.67–1.96(3H, m), 1.99(3H, s), 2.06–2.31(3H, m), 3.70(6H, s), 4.70–4.81(1H, m), 5.05(2H, s), 5.50–5.59(1H, m), 6.84(1H, dd, J=8.5, 2.0 Hz), 6.89(1H, d, J=8.5 Hz), 7.03(1H, d, J=2.0 Hz), 7.39(1H, dd, J=8.5, 2.0 Hz), 7.47(1H, d, J=8.5 Hz), 7.53(1H, d, J=2.0 Hz).

(15) 3-(trans-4-Acetoxycyclohexyl)-1-(3-chloro-4-methoxybenzyl)-6-trifluoromethyl-2,3-dihydro-1H-imidazo[4,5-b]pyridin-2-one mp. 165–166° C.

NMR(DMSO-d$_6$, δ): 1.46–1.64(2H, m), 1.77–1.88(2H, m), 1.97–2.08(2H, m), 2.02(3H, s), 2.387–2.51(2H, m), 3.82(3H, s), 4.34–4.46(1H, m), 4.60–4.74(1h, m), 5.06(2H, s), 7.11(1H, d, J=8.0 Hz), 7.33(1H, dd, J=8.0, 2.5 Hz), 7.52(1H, d J=2.5 Hz), 8.00(1H, d, J=1.5 Hz), 8.40(1H, d, J=1.5 Hz).

(16) 3-(3-Chloro-4-methoxybenzyl)-1-(trans-4-hydroxycyclohexyl)-5-nitro-2,3-dihydro-1H-benzimidazol-2-one mp. 142–142.5° C.

NMR(DMSO-d$_6$, δ): 1.29–1.47(2H, m), 1.69–1.80(2H, m), 1.90–2.02(2H, m), 2.14–2.31(2H, m), 3.50–3.64(1H, m), 3.81(3H, s), 4.21–4.36(1H, m), 4.70(1H, d, J=4.5 Hz), 5.11(2H, s), 7.11(1H, d, J=8.5 Hz), 7.30(1H, dd, J=8.5, 2.0 Hz), 7.48(1H, d, J=2.0 Hz), 7.60(1H, d, J=9.0 Hz), 8.00(1H, dd, J=9.0, 2.0 Hz), 8.11(1H, d, J=2.0 Hz).

(17) 1-(3-Chloro-4-methoxybenzyl)-3-cyclopentyl-6-trifluoromethyl-2,3-dihydro-1H-imidazo[4,5-b]pyridin-2-one mp. 156–157° C.

NMR(DMSO-d$_6$, δ): 1.55–1.74(2H, m), 1.85–2.02(4H, m), 2.12–2.30(2H, m), 3.82(3H, s), 4.80–4.94(1H, m), 5.06 (2H, s), 7.13(1H, d, J=8.5 Hz), 7.34(1H, dd, J=8.5, 2.5 Hz), 7.53(1H, d, J=2.5 Hz), 8.00(1H, s), 8.40(1H, s).

MS m/z: 426(M$^+$+1).

(18) 1-((S)-1-tert-Butoxycarbonylpyrrolidin-3-yl)-3-(3,4-dimethoxybenzyl)-5-trifluoromethyl-2,3-dihydro-1H-benzimidazol-2-one mp. 122–122.5° C.

NMR(DMSO-d$_6$, δ): 1.41(9H, s), 2.10–2.25(1H, m), 2.45–2.57(1H, m), 3.27–3.40(1H, m), 3.52–3.74(3H, m), 3.70(3H, s), 3.71(3H, s), 5.05(2H, s), 5.05–5.18(1H, m), 6.83(1H, dd, J=8.0, 2.0 Hz), 6.89(1H, d, J=8.0 Hz), 7.09(1H, d, J=2.0 Hz), 7.41(1H, d, J=8.0 Hz), 7.44(1H, d, J=8.0 Hz), 7.59(1H, s).

MS m/z: 522(M$^+$+1).

(19) 1-((S)-1-tert-Butoxycarbonylpyrrolidin-3-yl)-3-(3-chloro-4-methoxybenzyl)-5-trifluoromethyl-2,3-dihydro-1H-benzimidazol-2-one mp. 157–157.5° C.

NMR(DMSO-d$_6$, δ): 1.41(9H, s), 2.12–2.25(1H, m), 2.45–2.57(1H, m), 3.29–3.39(1H, m), 3.52–3.70(3H, m), 3.81(3H, s), 5.07(2H, s), 5.05–5.16(1H, m), 7.12(1H, d, J=8.5 Hz), 7.30(1H, dd, J=8.5, 2.0), 7.44(2H, s), 7.49 (1H, d, J=2.0 Hz), 7.62(1H, s).

MS m/z: 526(M$^+$+1).

(20) 1-(1H-Benzimidazol-5-yl)-3-(3,4-dimethoxybenzyl)-5-trifluoromethyl-2,3-dihydro-1H-benzimidazol-2-one mp. 174–175° C.

NMR(DMSO-d$_6$, δ): 3.72(3H, s), 3.74(3H, s), 5.16(2H, s), 6.93(1H, d, J=8.5 Hz), 6.95(1H, s), 7.10(1H, d, J=8.5 Hz), 7.16(1H, s), 7.30–7.41(2H, m), 7.68(1H, s), 7.72–7.85(2H, m), 8.38(1H, s).

MS m/z: 467(M$^+$−1)

(21) 1-(1H-Benzimidazol-5-yl)-3-(3-chloro-4-methoxybenzyl)-5-trifluoromethyl-2,3-dihydro-1H-benzimidazol-2-one mp. 158–160° C.

NMR(DMSO-d$_6$, δ): 3.83(3H, s), 5.18(2H, s), 7.06–7.18 (1H, br), 7.15(1H, d, J=8.5 Hz), 7.30–7.45(3H, m), 7.58(1H, d, J=2.5 Hz), 7.71(1H, s), 7.70–7.88(2H, br), 8.38(1H, s).

MS m/z: 471(M$^+$−1).

(22) 5-Acetyl-3-(3-chloro-4-methoxybenzyl)-1-(trans-4-hydroxycyclohexyl)-2,3-dihydro-1H-benzimidazol-2-one mp. 209–210° C.

NMR(DMSO-d$_6$, δ): 1.30–1.46(2H, m), 1.66–1.77(2H, m), 1.89–2.00(2H, m), 2.15–2.32(2H, m), 2.54(3H, s), 3.51–3.65(1H, m), 3.80(3H, s), 4.19–4.32(1H, m), 4.69(1H, d, J=4.0 Hz), 5.06(2H, s), 7.11(1H, d, J=8.5 Hz), 7.25(1H, dd, J=8.5, 2.0 Hz), 7.43(1H, d, J=2.0 Hz), 7.48(1H, d, J=8.5 Hz), 7.71(1H, d, J=1.5 Hz), 7.72(1H, dd, J=8.5, 1.5 Hz).

(23) 3-(trans-4-Acetoxycyclohexyl)-1-(3,4-dichlorobenzyl)-6-trifluoromethyl-2,3-dihydro-1H-imidazol[4,5-b]pyridin-2-one NMR(DMSO-d$_6$, δ): 1.46–1.65(2H, m), 1.79–1.90(2H, m), 1.99–2.08(2H, m), 2.02(3H, s), 2.38–2.56(2H, m), 4.32–4.45(1H, m), 4.60–4.74(1H, m), 5.14(2H, s), 7.32(1H, dd, J=8.5, 2.0 Hz), 7.61(1H, d, J=8.5 Hz), 7.71(1H, d, J=2.0 Hz), 8.01(1H, d, J=2.0 Hz), 8.42(1H, d, J=2.0 Hz).

(24) 3-(3-Chloro-4-methoxybenzyl)-1-(trans-4-hydroxycyclohexyl)-5-trifluoromethyl-2,3-dihydro-1H-benzimidazol-2-one mp. 167–168° C.

NMR(DMSO-d$_6$, δ): 1.29–1.45(2H, m), 1.65–1.76(2H, m), 1.90–2.00(2H, m), 2.14–2.30(2H, m), 3.51–3.64(1H, m), 3.81(3H, s), 4.17–4.30(1H, m), 4.69(1H, d, J=4.5 Hz), 5.06(2H, s), 7.11(1H, d, J=8.5 Hz), 7.27(1H, dd, J=8.5, 2.0 Hz), 7.37(1H, dd, J=8.5, 1.5 Hz), 7.47(1H, d, J=2.0 Hz), 7.56(1H, d, J=8.5 Hz), 7.60(1H, d, J=1.5 Hz).

(25) 1-(trans-4-Acetoxycyclohexyl)-3-(3,4-dimethoxybenzyl)-5-methyl-2,3-dihydro-1H-benzimidazol-2-one NMR(DMSO-d$_6$, δ): 1.47–1.64(2H, m), 1.67–1.80(2H, m), 1.97–2.08(2H, m), 2.02(3H, s), 2.21–2.40(2H, m), 2.28 (3H, s), 3.69(3H, s), 3.71(3H, s), 4.20–4.35(1H, m), 4.73–4.86(1H, m), 4.92(2H, s), 6.77(1H, dd, J=8.0, 2.0 Hz), 6.82(1H, d, J=8.0 Hz), 6.87(1H, d, J=8.0 Hz), 6.96(1H, s), 6.99(1H, d, J=2.0 Hz), 7.30(1H, d, J=8.0 Hz).

MS m/z: 439(M$^+$+1).

(26) 3-(3,5-Dichloro-4-methoxybenzyl)-1-(trans-4-hydroxycyclohexyl)-5-nitro-2,3-dihydro-1H-benzimidazol-2-one mp. 115–116° C.

NMR(DMSO-d$_6$, δ): 1.30–1.46(2H, m), 1.70–1.81(2H, m), 1.90–2.00(2H, m), 2.13–2.31(2H, m), 3.51–3.64(1H, m), 3.79(3H, s), 4.20–4.35(1H, m), 4.69(1H, d, J=4.5 Hz), 5.14(2H, s), 7.51(2H, s), 7.63(1H, d, J=9.0 Hz), 8.02(1H, dd, J=9.0, 2.5 Hz), 8.19(1H, d, J=2.5 Hz).

(27) 3-(3-Chloro-4-methoxybenzyl)-1-(trans-4-hydroxycyclohexyl)-5-methoxycarbonyl-2,3-dihydro-1H-benzimidazol-2-one mp. 174–175° C.

NMR(DMSO-$d_6$, δ): 1.29–1.45(2H, m), 1.67–1.78(2H, m), 1.89–2.07(2H, m), 2.15–2.31(2H, m), 3.50–3.64(2H, m), 3.81(3H, s), 3.82(3H, s), 4.19–4.32(1H, m), 4.68(1H, d, J=4.5 Hz), 5.06(2H, s), 7.10(1H, d, J=8.5 Hz), 7.22(1H, dd, J=8.5, 2.5 Hz), 7.41(1H, d, J=2.5 Hz), 7.50(1H, d, J=8.5 Hz), 7.68(1H, s), 7.70(1H, d, J=8.5 Hz).

(28) 3-(3-Chloro-4-methoxybenzyl)-5-cyano-1-(trans-4-hydroxycyclohexyl)-2,3-dihydro-1H-benzimidazol-2-thione NMR(DMSO-$d_6$, δ): 1.29–1.47(2H, m), 1.66–1.78(2H, m), 1.89–2.01(2H, m), 2.15–2.31(2H, m), 3.55–3.70(1H, m), 3.82(3H, s), 4.18–4.31(2H, m), 4.59(2H, s), 4.73(1H, d, J=4.5 Hz), 7.09(1H, d, J=8.5 Hz), 7.42(1H, dd, J=8.5, 2.5 Hz), 7.55(1H, dd, J=8.5 , 2.5 Hz), 7.57(4H, d, J=2.5 Hz ), 7.90(1H, d, J=8.5 Hz), 8.10(1H, d, J=2.5 Hz).

MS m/z: 428(M$^+$+1).

(29) 3-(3-Chloro-4-ethoxybenzyl)-1-(trans-4-hydroxycyclohexyl)-5-trifluoromethyl-2,3-dihydro-1H-benzimidazol-2-one mp. 147.5–149° C.

NMR(DMSO-$d_6$, δ): 1.32(3H, t, J=7.0 Hz), 1.29–1.45 (2H, m), 1.65–1.76(2H, m), 1.89–2.03(2H, m), 2.14–2.30 (2H, m), 3.51–3.64(1H, m), 4.06(2H, q, J=7.0 Hz), 4.18–4.31(5H, m), 4.69(1H, d, J=4.0 Hz), 5.05(2H, s), 7.09(1H, d, J=8.5 Hz), 7.25(1H, dd, J=8.5 , 2.5 Hz), 7.37 (1H, dd, J=8.5, 2.5 Hz), 7.46(1H, d, J=2.5 Hz), 7.56(1H, d, J=8.5 Hz), 7.60(1H, d, J=2.5 Hz).

(30) 3-(3-Fluoro-4-methoxybenzyl)-1-(trans-4-hydroxycyclohexyl)-5-trifluoromethyl-2,3-dihydro-1H-benzimidazol-2-one mp. 178–179° C.

NMR(DMSO-$d_6$, δ): 1.29–1.46(2H, m), 1.66–1.77(2H, m), 1.90–2.00(2H, m), 2.15–2.31(2H, m), 3.52–3.63(1H, m), 3.79(3H, s), 4.19–4.31(1H, m), 4.69(1H, d, J=4.5 Hz), 5.05(2H, s), 7.08–7.14(2H, m), 7.23(1H, d, J=13.0 Hz), 7.37(1H, d, J=8.5 Hz), 7.56(1H, d, J=8.5 Hz), 7.56(1H, s).

(31) 3-(3-Bromo-4-methoxybenzyl)-1-(trans-4-hydroxycyclohexyl)-5-trifluoromethyl-2,3-dihydro-1H-benzimidazol-2-one mp. 182–182.5° C.

NMR(DMSO-$d_6$, δ): 1.29–1.45(2H, m), 1.65–1.77(2H, m), 1.89–2.02(2H, m), 2.15–2.32(2H, m), 3.51–3.65(1H, m), 3.80(3H, s), 4.18–4.31(1H, m), 4.69(1H, d, J=4.5 Hz), 5.06(2H, s), 7.08(1H, d, J=8.5 Hz), 7.32(1H, dd, J=8.5, 2.5 Hz), 7.37(1H, d, J=8.5 Hz), 7.56(1H, d, J=8.5 Hz), 7.61(1H, s), 7.63(1H, d, J=2.5 Hz).

(32) 1-(tert-Butyl)-3-(3-chloro-4-methoxybenzyl)-5-trifluoromethyl-2,3-dihydro-1H-benzimidazol-2-one mp. 130.5–131.5° C.

NMR(DMSO-$d_6$, δ): 1.75(9H, s), 3.81(3H, s), 5.04(2H, s), 7.12(1H, d, J=8.5 Hz), 7.26(1H, dd, J=8.5, 2.5 Hz), 7.32(1H, dd, J=8.5, 2.0 Hz), 7.45(1H, d, J=2.5 Hz), 7.54(1H, d, J=2.0 Hz), 7.69(1H, d, J=8.5 Hz).

(33) 3-(3,5-Dichloro-4-methoxybenzyl)-1-(trans-4-hydroxycyclohexyl)-5-trifluoromethyl-2,3-dihydro-1H-benzimidazol-2-one NMR(DMSO-$d_6$, δ): 1.27–1.45(2H, m), 1.66–1.78(2H, m), 1.89–1.99(2H, m), 2.12–2.29(2H, m), 3.52–3.64(1H, m), 3.79(3H, s), 4.17–4.31(1H, m), 4.69(1H, d, J=4.0 Hz), 5.09(2H, s), 7.39(1H, dd, J=8.0, 2.0 Hz), 7.49(2H, s), 7.59(1H, d, J=8.0 Hz), 7.68(1H, d, J=2.0 Hz).

(34) 3-(3-Chloro-4-methoxybenzyl)-1-(tetrahydro-4H-pyran-4-yl)-5-trifluoromethyl-2,3-dihydro-1H-benzimidazol-2-one mp. 175–176° C.

NMR(DMSO-$d_6$, δ): 1.66–1.76(2H, m), 2.30–2.47(2H, m), 3.43–3.55(2H, m), 3.81(3H, s), 3.95–4.05(2H, m), 4.46–4.60(1H, m), 5.07(2H, s), 7.11(1H, d, J=8.5 Hz), 7.30(1H, dd, J=8.5, 2.5 Hz), 7.41(1H, d, J=8.5 Hz), 7.48(1H, d, J=2.5 Hz), 7.55(1H, d, J=8.5 Hz), 7.62(1H, s).

(35) 3-(3-Chloro-4-methoxybenzyl)-1-isopropyl-5-trifluoromethyl-2,3-dihydro-1H-benzimidazol-2-one mp. 153.5–155° C.

NMR(DMSO-$d_6$, δ): 1.48(6H, d, J=7.0 Hz), 3.81(3H, s), 4.69(1H, pent., J=7.0 Hz), 5.06(2H, s), 7.12(1H, d, J=8.5 Hz), 7.29(1H, dd, J=8.5, 2.0 Hz), 7.39(1H, dd, J=8.5, 1.5 Hz), 7.47(1H, d, J=2.0 Hz), 7.52(1H, d, J=8.5 Hz), 7.60(1H, d, J=1.5 Hz).

(36) 1-Butyl-3-(3-chloro-4-methoxybenzyl)-5-trifluoromethyl-2,3-dihydro-1H-benzimidazol-2-one mp. 122–124° C.

NMR(DMSO-$d_6$, δ): 0.89(3H, t, J=7.0 Hz), 1.20–1.34 (2H, m), 1.59–1.70(2H, m), 3.81(3H, s), 3.93(2H, t, J=7.0 Hz), 5.08(2H, s), 7.11(1H, d, J=8.5 Hz), 7.30(1H, dd, J=8.5, 2.0 Hz), 7.42(2H, s), 7.45(1H, d, J=2.0 Hz), 7.61(1H, s).

(37) 1-Cyclohexyl-3-(3-chloro-4-methoxybenzyl)-5-trifluoromethyl-2,3-dihydro-1H-benzimidazol-2-one mp. 160–161° C.

NMR(DMSO-$d_6$, δ): 1.20–1.51(3H, m), 1.63–1.90(5H, m), 2.05–2.21(2H, m), 3.81(3H, s), 4.19–4.32(1H, m), 5.06 (2H, s), 7.11(1H, d.J=8.5 Hz), 7.28(1H, dd, J=8.5, 2.5 Hz), 7.38(1H, d, J=8.5 Hz), 7.47(1H, d, J=2.5 Hz), 7.57(1H, d, J=8.5 Hz), 7.60(1H, s).

(38) 1-(3-Chloro-4-methoxybenzyl)-3-(trans-4-formamidocyclohexyl)-6-trifluoromethyl-2,3-dihydro-1H-imidazol4,5-b]pyridin-2-one mp. 207–208° C.

NMR(DMSO-$d_6$, δ): 1.30–1.51(2H, m), 1.75–2.00(4H, m), 2.35–2.55(2H, m), 3.63–3.76(1H, m), 3.82(3H, s), 4.27–4.43(1H, m), 5.06(2H, s), 7.12(1H, d, J=8.5 Hz), 7.33(1H, dd, J=8.5, 2.0 Hz), 7.52(1H, d, J=2.0 Hz), 7.97(1H, s), 8.00(1H, s), 8.06(1H, d, J=7.0 Hz), 8.41(1H, s).

(39) 3-(4-Chloro-3-methoxybenzyl)-5-cyano-1-(trans-4-hydroxycyclohexyl)-2,3-dihydro-1H-benzimidazol-2-one NMR(DMSO-$d_6$, δ): 1.22–1.46 (2H, m), 1.65–1.78 (2H, m), 1.86–2.00 (2H, m), 2.12–2.30 (2H, m), 3.50–3.64 (1H, m), 3.84 (3H, s), 4.19–4.31 (1H, m), 4.69 (1H, d, J=4 Hz), 5.05 (2H, s), 6.83 (1H, dd, J=8, 2 Hz), 7.23 (1H, d, J=2 Hz), 7.36 (1H, d, J=8 Hz), 7.50 (1H, dd, J=8, 2 Hz), 7.60 (1H, d, J=8 Hz), 7.73 (1H, d, J=2 Hz).

(40) 3-(3-Chloro-4-methoxybenzyl)-5-cyano-1-(trans-4-hydroxycyclohexyl)-2,3-dihydro-1H-benzimidazol-2-one NMR(DMSO-$d_6$, δ): 1.28–1.46 (2H, m), 1.64–1.76 (2H, m), 1.86–2.00 (2H, m), 2.10–2.31 (2H, m), 3.49–3.64 (1H, m), 3.81 (3H, s), 4.17–4.32 (1H, m), 4.68 (1H, d, J=4 Hz), 4.99 (3H, s), 7.10 (1H, d, J=8 Hz), 7.31 (1H, dd, J=8, 2 Hz), 7.45–7.52 (2H, m), 7.56 (1H, d, J=8 Hz), 7.78 (1H, d, J=2 Hz).

(41) 5-Cyano-3-(3,4-dimethoxybenzyl)-1-((R)-2-hydroxy-1-methylethyl)-2,3-dihydro-1H-benzimidazol-2-one NMR(CDCl$_3$, δ): 1.55 (3H, d, J=7.5 Hz), 3.20 (1H, dd, J=5, 7.5 Hz), 3.85 (3H, s), 3.87 (3H, s), 3.99–4.16 (2H, m), 4.44–4.56 (1H, m), 5.00 (2H, s), 6.80–6.93 (3H, m), 7.10–7.18 (2H, m), 7.40 (1H, dd, J=8, 2 Hz).

(42) 5-Cyano-3-(3,4-dimethoxybenzyl)-1-((S)-2-hydroxy-1-methylethyl)-2,3-dihydro-1H-benzimidazol-2-one NMR(CDCl$_3$, δ): 1.55 (3H, d, J=7.5 Hz),3.20 (1H, dd, J=5, 7.5 Hz), 3.85 (3H, s), 3.87 (3H, s), 3.99–4.16 (2H, m), 4.44–4.56 (1H, m), 5.00 (2H, s), 6.80–6.93 (3H, m), 7.11–7.19 (2H, m), 7.40 (1H, dd, J=8, 2 Hz).

(43) 5-Cyano-3-(3,4-dimethoxybenzyl)-1-(trans-4-formamidocyclohexyl)-2,3-dihydro-1H-benzimidazol-2-one NMR(DMSO-$d_6$, δ): 1.31–1.51 (2H, m), 1.69–1.82 (2H, m), 1.82–2.01 (2H, m), 3.70 (3H, s), 3.72 (3H, s), 3.80 (1H, br), 4.23–4.38 (1H, m), 4.99 (2H, s), 6.83–6.92 (2H, m), 7.04 (1H, s), 7.49 (1H, dd, J=8, 2 Hz), 7.66 (1H, d, J=8 Hz), 7.72 (1H, d, J=2 Hz), 7.97 (1H, s), 8.05 (1H, d, J=8 Hz).

(44) 3-(4-Chloro-3-methoxybenzyl)-5-cyano-1-(trans-4-formamidocyclohexyl)-2,3-dihydro-1H-benzimidazol-2-one NMR(DMSO-$d_6$, δ): 1.32–1.55 (2H, m), 1.70–1.85 (2H, m), 1.85–2.00 (2H, m), 2.19–2.38 (2H, m), 3.72–3.91 (4H, m), 4.22–4.37 (1H, m), 5.06 (2H, s), 6.84 (1H, d, J=8 Hz), 7.24 (1H, s), 7.36 (1H, d, J=8 Hz), 7.50 (1H, d, J=8 Hz), 7.68 (1H, d, J=8 Hz), 7.74 (1H, s), 7.94 (1H, s), 8.05 (1H, d, J=8 Hz).

(45) 3-(3-Chloro-4-methoxybenzyl)-5-cyano-1-(trans-4-formamidocyclohexyl)-2,3-dihydro-1H-benzimidazol-2-one NMR(DMSO-$d_6$, δ): 1.32–1.55 (2H, m), 1.69–1.84 (2H, m), 1.84–2.00 (2H, m), 2.17–2.86 (2H, m), 3.72–3.88 (4H, m), 4.20–4.36 (1H, m), 5.00 (2H, s), 7.11 (1H, d, J=8 Hz), 7.33 (1H, dd, J=8, 2 Hz), 7.42–7.55 (2H, m), 7.67 (2H, d, J=8 Hz), 7.78 (1H, d, J=2 Hz), 7.97 (1H, s), 8.04 (1H, d, J=8 Hz).

(46) 5-Cyano-3-(2-methoxyphenethyl)-1-(trans-4-hydroxycyclohexyl)-2,3-dihydro-1H-benzimidazol-2-one NMR(DMSO-$d_6$, δ): 1.25–1.43 (2H, m), 1.56–1.69 (2H, m), 1.86–1.97 (2H, m), 2.07–2.25 (2H, m), 2.90 (2H, t, J=7.5 Hz), 3.47–3.62 (1H, m), 3.64 (3H, s), 4.03 (2H, t, J=7.5 Hz), 4.10–4.24 (1H, m), 4.67 (1H, d, J=5 Hz), 6.74–6.89 (2H, m), 7.05 (1H, dd, J=8, 2 Hz), 7.15 (1H, ddd, J=8, 8, 2 Hz), 7.33 (1H, s), 7.43 (1H, d, J=8 Hz), 7.50 (1H, d, J=8 Hz).

(47) 5-Cyano-3-(3,4-dimethoxybenzyl)-1-(2,2-dimethyl-1,3-dioxan-5-yl)-2,3-dihydro-1H-benzimidazol-2-one NMR(CDCl$_3$, δ): 1.50 (3H, s), 1.59 (3H, s), 3.86 (3H, s), 3.89 (3H, s), 4.10 (2H, dd, J=11, 5 Hz), 4.26 (2H, dd, J=11, 7.5 Hz), 4.66–4.78 (1H, m), 4.98 (2H, s), 6.80–6.92 (3H, m), 7.17 (1H, dd, J=8, 2 Hz), 7.42 (1H, dd, J=8, 2 Hz), 7.64 (1H, d, J=8 Hz).

(48) 3-(4-Chloro-3-methoxybenzyl)-5-cyano-1-(2,2-dimethyl-1,3-dioxan-5-yl)-2,3-dihydro-1H-benzimidazol-2-one NMR(CDCl$_3$, δ): 1.50 (3H, s), 1.58 (3H, s), 3.89 (3H, s), 4.10 (2H, dd, J=5, 11 Hz), 4.25 (2H, dd, J=7, 11 Hz), 4.66–4.78 (1H, m), 5.00 (2H, s), 6.80 (1H, dd, J=8, 2 Hz), 6.90 (1H, d, J=2 Hz), 7.14 (1H, d, J=8 Hz), 7.32 (1H, d, J=8 Hz), 7.44 (1H, dd, J=8, 2 Hz), 7.67 (1H, d, J=2 Hz).

(49) 3-(3-Chloro-4-methoxybenzyl)-5-cyano-1-(2,2-dimethyl-1,3-dioxan-5-yl)-2,3-dihydro-1H-benzimidazol-2-one NMR(DMSO-$d_6$, δ): 1.42 (3H, s), 1.51 (3H, s), 4.04 (2H, dd, J=11, 6 Hz), 4.24 (2H, dd, J=11, 7.5 Hz), 4.54–4.64 (1H, m), 5.00 (2H, s), 7.11 (1H, d, J=8 Hz), 7.33 (1H, dd, J=8, 2 Hz), 7.50 (1H, d, J=2 Hz), 7.56 (1H, dd, J=8, 2 Hz), 7.74–7.82 (2H, m).

(50) 1-(2-Acetoxy-1,1-dimethylethyl)-5-cyano-3-(3,4-dimethoxybenzyl)-2,3-dihydro-1H-benzimidazol-2-one NMR(CDCl$_3$, δ): 1.86 (6H, s), 1.94 (3H, s), 3.85 (3H, s), 3.87 (3H, s), 4.63 (2H, s), 4.96 (2H, s), 6.80–6.90 (3H, m), 7.12 (1H, d, J=2 Hz), 7.30 (1H, dd, J=8, 2 Hz), 7.42 (1H, d, J=8 Hz).

(51) 1-(2-Acetoxy-1,1-dimethylethyl)-3-(4-chloro-3-methoxybenzyl)-5-cyano-2,3-dihydro-1H-benzimidazol-2-one NMR(CDCl$_3$, δ): 1.87 (6H, s), 1.93 (3H, s), 3.88 (3H, s), 4.63 (2H, s), 4.99 (2H, s), 6.79 (1H, dd, J=8, 2 Hz), 6.91 (1H, d, J=2 Hz), 7.07 (1H, d, J=2 Hz), 7.29–7.36 (2H, m), 7.44 (1H, d, J=8 Hz).

(52) 1-(2-Acetoxy-1,1-dimethylethyl)-3-(3-chloro-4-methoxybenzyl)-5-cyano-2,3-dihydro-1H-benzimidazol-2-one NMR(CDCl$_3$, δ): 1.86 (6H, s), 1.97 (3H, s), 3.89 (3H, s), 4.62 (3H, s), 4.95 (3H, s), 6.90 (1H, d, J=8 Hz), 7.06 (1H, d, J=2 Hz), 7.17 (1H, dd, J=8, 2 Hz), 7.25–7.35 (2H, m), 7.44 (1H, d, J=8 Hz).

(53) 1-[(R)-2-Acetoxy-1-methylethyl]-3-(4-chloro-3-methoxybenzyl)-5-cyano-2,3-dihydro-1H-benzimidazol-2-one NMR(CDCl$_3$, δ): 1.63 (3H, d, J=7.5 Hz), 1.91 (3H, s), 3.88 (3H, s), 4.41 (1H, dd, J=11, 4 Hz), 4.56 (1H, dd, J=11, 9 Hz), 4.70–4.85 (1H, m), 5.02 (2H, s), 6.80 (1H, dd, J=8, 2 Hz), 6.91 (1H, d, J=2 Hz), 7.11 (1H, d, J=2 Hz), 7.14 (1H, d, J=8 Hz), 7.33 (1H, d, J=8 Hz), 7.39 (1H, dd, J=8, 2 Hz).

(54) 1-[(R)-2-Acetoxy-1-methylethyl]-3-(3-chloro-4-methoxybenzyl)-5-cyano-2,3-dihydro-1H-benzimidazol-2-one NMR(CDCl$_3$, δ): 1.63 (3H, d, J=7.5 Hz), 1.94 (3H, s), 3.89 (3H, s), 4.41 (1H, dd, J=11, 4 Hz), 4.54 (1H, dd, J=11, 9 Hz), 4.73–4.87 (1H, m), 4.94 (1H, d, J=15 Hz), 5.02 (1H, d, J=15 Hz), 6.90 (1H, d, J=8 Hz), 7.09 (1H, d, J=2 Hz), 7.14 (1H, d, J=8 Hz), 7.19 (1H, dd, J=8, 2Hz), 7.30 (1H, d, J=2 Hz), 7.39 (1H, dd, J=8, 2 Hz).

(55) 1-[(S)-2-Acetoxy-1-methylethyl]-3-(4-chloro-3-methoxybenzyl)-5-cyano-2,3-dihydro-1H-benzimidazol-2-one NMR(CDCl$_3$, δ): 1.63 (3H, d, J=7.5 Hz), 1.91 (3H, s), 3.88 (3H, s), 4.41 (1H, dd, J=11, 4 Hz), 4.56 (1H, dd, J=11, 9 Hz), 4.70–4.85 (1H, m), 5.02 (2H, s), 6.80 (1H, dd, J=8,2 Hz), 6.91 (1H, d, J=2 Hz), 7.11 (1H, d, J=2 Hz), 7.14 (1H, d, J=8 Hz), 7.33 (1H, d, J=8 Hz), 7.40 (1H, dd, J=8, 2 Hz).

(56) 1-[(S)-2-Acetoxy-1-methylethyl]-3-(3-chloro-4-methoxybenzyl)-5-cyano-2,3-dihydro-1H-benzimidazol-2-one NMR(CDCl$_3$, δ): 1.63 (3H, d, J=7.5 Hz), 1.94 (3H, s), 3.89 (3H, s), 4.41 (1H, dd, J=11, 4 Hz), 4.54 (1H, dd, J=11, 9 Hz), 4.73–4.87 (1H, m), 4.94 (1H, d, J=15 Hz), 5.02 (1H, d, J=15 Hz), 6.90 (1H, d, J=8 Hz), 7.09 (1H, d, J=2 Hz), 7.14 (1H, d, J=8 Hz), 7.19 (1H, dd, J=8, 2Hz), 7.30 (1H, d, J=2 Hz), 7.39 (1H, dd, J=8, 2 Hz).

(57) 1-(2-Acetoxy-1,1-dimethylethyl)-3-(3,4-dimethoxybenzyl)-5-trifluoromethyl-2,3-dihydro-1H-benzimidazol-2-one NMR(CDCl$_3$, δ): 1.86 (6H, s), 1.98 (3H, s), 3.84 (3H, s), 3.85 (3H, s), 4.65 (2H, s), 4.99 (2H, s), 6.78–6.92 (3H, m), 7.14 (1H, d, J=2 Hz), 7.22–7.31 (1H, m), 7.43 (1H, d, J=8 Hz).

(58) 1-(2-Acetoxy-1,1-dimethylethyl)-3-(4-chloro-3-methoxybenzyl)-5-trifluoromethyl-2,3-dihydro-1H-benzimidazol-2-one NMR(CDCl$_3$, δ): 1.86 (6H, s), 1.94 (3H, s), 3.87 (3H, s), 4.64 (2H, s), 5.01 (2H, s), 6.81 (1H, dd, J=8, 2 Hz), 6.93 (1H, d, J=2 Hz), 7.09 (1H, s-like), 7.25–7.34 (2H, m), 7.46 (1H, d, J=8 Hz).

(59) 1-(2-Acetoxy-1,1-dimethylethyl)-3-(3-chloro-4-methoxybenzyl)-5-trifluoromethyl-2,3-dihydro-1H-benzmidazol-2-one NMR(CDCl$_3$, δ): 1.86 (6H, s), 1.97 (3H, s), 3.88 (3H, s), 4.64 (2H, s), 4.97 (2H, s), 6.89 (1H, d, J=8 Hz), 7.07 (1H,

(60) 1-[(S)-1-tert-Butoxycarbonylpyrrolidin-3-yl]-3-(3-chloro-4-methoxybenzyl)-5-cyano-2,3-dihydro-1H-benzimidazol-2-one NMR(CDCl$_3$, δ): 1.49 (9H, s), 2.24–2.36 (1H, m), 2.45–2.63 (1H, m), 3.41–3.55 (1H, m), 3.66–3.85 (3H, m), 3.90 (3H, s), 4.90 (2H, s), 5.09–5.21 (1H, m), 6.90 (1H, d, J=8 Hz), 7.08–7.15 (2H, m), 7.21 (1H, dd, J=8, 2 Hz), 7.33 (1H, d, J=2 Hz), 7.40 (1H, d, J=8 Hz).

(61) 1-[(R)-1-tert-Butoxycarbonylpyrrolidin-3-yl]-3-(3-chloro-4-methoxybenzyl)-5-cyano-2,3-dihydro-1H-benzimidazol-2-one NMR(CDCl$_3$, δ): 1.49 (9H, s), 2.21–2.36 (1H, m), 2.45–2.63 (1H, m), 3.40–3.55 (1H, m), 3.66–3.85 (3H, m), 3.90 (3H, s), 4.97 (2H, s), 5.08–5.24 (1H, m), 6.90 (1H, d, J=8 Hz), 7.06–7.14 (2H, m), 7.21 (1H, dd, J=8, 2 Hz), 7.33 (1H, d, J=2 Hz), 7.40 (1H, d, J=8 Hz).

(62) 1-[trans-4-(N-tert-Butoxycarbonylamino) cyclohexyl]-3-(3-chloro-4-methoxybenzyl)-5-cyano-2,3-dihydro-1H-benzimidazol-2-one NMR(DMSO-d$_6$, δ): 1.28–1.46 (11H, m), 1.68–1.78 (2H, m), 1.85–1.96 (2H, m), 2.14–2.32 (2H, m), 3.40 (1H, br), 3.81 (3H, s), 4.15–4.30 (1H, m), 4.99 (2H, s), 6.83 (1H, d, J=8 Hz), 7.11 (1H, d, J=8 Hz), 7.31 (1H, dd, J=8, 2 Hz), 7.46–7.53 (2H, m), 7.64 (1H, d, J=8 Hz), 7.77 (1H, s-like).

(63) 1-(cis-4-Acetoxycyclohexyl)-3-(3-chloro-4-methoxybenzyl)-5-cyano-2,3-dihydro-1H-benzimidazol-2-one NMR(CDCl$_3$, δ): 1.64–1.83 (4H, m), 2.06–2.20 (5H, m), 2.36–2.54 (2H, m), 3.90 (3H, s), 4.36–4.50 (1H, m), 4.98 (2H, s), 5.10–5.16 (1H, m), 6.90 (1H, d, J=8 Hz), 7.11 (1H, d, J=2 Hz), 7.16–7.23 (2H, m), 7.33 (1H, d, J=2 Hz), 7.39 (1H, dd, J=8, 2 Hz).

(64) 1-(trans-4-Acetoxycyclohexyl)-5-cyano-3-piperonyl-2,3-dihydro-1H-benzimidazol-2-one NMR(DMSO-d$_6$, δ): 1.47–1.65 (2H, m), 1.72–1.84 (2H, m), 1.97–2.10 (5H, m), 2.20–2.40 (2H, m), 4.27–4.41 (1H, m), 4.75–4.88 (1H, m), 4.96 (2H, s), 5.98 (2H, s), 6.84–6.94 (2H, m), 6.97 (1H, s), 7.50 (1H, d, J=2 Hz), 7.66 (1H, d, J=8 Hz), 7.73 (1H, s).

(65) 1-(trans-4-Acetoxycyclohexyl)-3-(2-chlorobenzyl)-5-cyano-2,3-dihydro-1H-benzimidazol-2-one NMR(CDCl$_3$, δ): 1.52–1.70 (2H, m), 1.91–2.03 (2H, m), 2.08 (3H, s), 2.14–2.41 (4H, m), 4.33–4.48 (1H, m), 4.76–4.90 (1H, m), 5.19 (2H, s), 7.05–7.15 (2H, m), 7.15–7.30 (3H, m), 7.36–7.46 (2H, m).

(66) 1-(trans-4-Acetoxycyclohexyl)-3-(3-chlorobenzyl)-5-cyano-2,3-dihydro-1H-benzimidazol-2-one NMR(CDCl$_3$, δ): 1.50–1.69 (2H, m), 1.90–2.03 (2H, m), 2.10–2.40 (4H, m), 4.33–4.46 (1H, m), 4.76–4.90 (1H, m), 5.03 (2H, s), 7.07 (1H, d, J=2 Hz), 7.14–7.24 (2H, m), 7.24–7.34 (4H, m), 7.40 (1H, dd, J=8, 2 Hz).

(67) 1-(trans-4-Acetoxycyclohexyl)-3-(4-chlorobenzyl)-5-cyano-2,3-dihydro-1H-benzimidazol-2-one NMR(CDCl$_3$, δ): 1.50–1.69 (2H, m), 1.90–2.01 (2H, m), 2.07 (3H, s), 2.13–2.40 (4H, m), 4.30–4.45 (1H, m), 4.76–4.89 (1H, m), 5.02 (2H, s), 7.08 (1H, d, J=2 Hz), 7.14–7.29 (3H, m), 7.31 (2H, d, J=8 Hz), 7.39 (1H, dd, J=8, 2 Hz).

(68) 3-(2-Chloro-4-methoxybenzyl)-5-cyano-1-(trans-4-hydroxycyclohexyl)-2,3-dihydro-1H-benzimidazol-2-one NMR(DMSO-d$_6$, δ): 1.28–1.45 (2H, m), 1.66–1.78 (2H, m), 1.88–2.00 (2H, m), 2.14–2.31(2H, m), 3.50–3.64 (1H, m), 3.75 (3H, s), 4.17–4.32 (1H, m), 4.68 (1H, d, J=5 Hz), 5.08 (2H, s), 6.88 (1H, dd, J=8, 2 Hz), 7.01 (1H, d, J=8 Hz), 7.09 (1H, d, J=2 Hz), 7.49–7.55 (2H, m), 7.61 (1H, d, J=8 Hz).

(69) 5-Cyano-3-(3,4-dichlorobenzyl)-1-(trans-4-hydroxycyclohexyl)-2,3-dihydro-1H-benzimidazol-2-one NMR(DMSO-d6, δ): 1.28–1.46 (2H, m), 1.66–1.78 (2H, m), 1.88–2.00 (2H, m), 2.12–2.30 (2H, m), 3.50–3.65 (1H, m), 4.17–4.32 (1H, m), 4.68 (1H, d, J=5 Hz), 5.07 (2H, s), 7.30 (1H, dd, J=8, 2 Hz), 7.52 (1H, dd, J=8, 2 Hz), 7.56–7.65 (2H, m), 7.68 (1H, d, J=2 Hz), 7.79 (1H, d, J=2 Hz).

(70) 5-Cyano-3-(3,5-dichloro-4-methoxybenzyl)-1-(trans-4-hydroxycyclohexyl)-2,3-dihydro-1H-benzimidazol-2-one NMR(CDCl$_3$, δ): 1.45–1.63 (2H, m), 1.89–2.00 (2H, m), 2.10–2.39 (4H, m), 3.70–3.86 (1H, m), 3.89 (3H, s), 4.24–4.38 (1H, m), 4.95 (2H, s), 7.09 (1H, d, J=2 Hz), 7.18 (1H, d, J=8 Hz), 7.26 (2H, s), 7.41 (1H, dd, J=8, 2 Hz).

(71) 3-(3-Chloro-4-ethoxybenzyl)-5-cyano-1-(trans-4-hydroxycyclohexyl)-2,3-dihydro-1H-benzimidazol-2-one NMR(CDCl$_3$, δ): 1.41–1.62 (5H, m), 1.87–1.99 (2H, m), 2.11–2.39 (4H, m), 3.73–3.86 (1H, m), 4.10 (2H, q, J=7.5 Hz), 4.25–4.37 (1H, m), 4.95 (2H, s) 6.88 (1H, d, J=8 Hz), 7.10 (1H, d, J=2 Hz), 7.12–7.20 (2H, m), 7.30 (1H, d, J=2 Hz), 7.39 (1H, dd, J=8, 2 Hz).

(72) 3-(3-Bromo-4-methoxybenzyl)-5-cyano-1-(trans-4-hydroxycyclohexyl)-2,3-dihydro-1H-benzimidazol-2-one NMR(DMSO-d$_6$, δ): 1.27–1.45 (2H, m), 1.65–1.76 (2H, m), 1.88–1.99 (2H, m), 2.12–2.30 (2H, m), 3.50–3.64 (1H, m), 3.80 (3H, s), 4.17–4.31 (1H, m), 4.68 (1H, d, J=5 Hz), 4.99 (2H, s), 7.06 (1H, d, J=8 Hz), 7.36 (1H, dd, J=8, 2 Hz), 7.50 (1H, d, J=8 Hz), 7.56 (1H, d, J=8 Hz), 7.64 (1H, d, J=2 Hz), 7.79 (1H, d, J=2 Hz).

(73) 5-Cyano-3-(3-fluoro-4-methoxybenzyl)-1-(trans-4-hydroxycyclohexyl)-2,3-dihydro-1H-benzimidazol-2-one NMR(DMSO-d$_6$, δ): 1.27–1.45 (2H, m), 1.65–1.76 (2H, m), 1.88–1.99 (2H, m), 2.12–2.29 (2H, m), 3.50–3.64 (1H, m), 3.79 (3H, s), 4.16–4.31 (1H, m), 4.67 (1H, d, J=5 Hz), 4.99 (2H, s), 7.07–7.19 (2H, m), 7.25 (1H, d, J=11 Hz), 7.50 (1H, d, J=8 Hz), 7.56 (1H, d, J=8 Hz), 7.74 (1H, d, J=2 Hz).

(74) 5-Cyano-3-(4-methoxy-3-methylbenzyl)-1-(trans-4-hydroxycyclohexyl)-2,3-dihydro-1H-benzimidazol-2-one NMR(DMSO-d$_6$, δ): 1.28–1.45 (2H, m), 1.64–1.75 (2H, m), 1.87–1.99 (2H, m), 2.09 (3H, s), 2.12–2.30 (2H, m), 3.50–3.64 (1H, m), 3.74 (3H, s), 4.19–4.30 (1H, m), 4.68 (1H, d, J=5 Hz), 4.95 (2H, s), 6.88 (1H, d, J=8 Hz), 7.14–7.21 (2H, m), 7.49 (1H, d, J=8 Hz), 7.56 (1H, d, J=8 Hz), 7.68 (1H, s).

(75) 3-(3-Chloro-4-ethoxybenzyl)-5-cyano-1-(trans-4-formamidocyclohexyl)-2,3-dihydro-1H-benzimidazol-2-one NMR(CDCl$_3$, δ): 1.36–1.55 (5H, m), 1.91–2.05 (2H, m), 2.11–2.43 (4H, m), 3.95–4.15 (3H, m), 4.34–4.48 (1H, m), 4.96 (2H, s), 5.44 (1H, d, J=7.5 Hz) 6.88 (1H, d, J=8 Hz), 7.10 (1H, d, J=2 Hz), 7.11–7.21 (2H, m), 7.30 (1H, d, J=2 Hz), 7.38 (1H, dd, J=8, 2 Hz), 8.16 (1H, s).

(76) 5-Cyano-3-(3,4-dichlorobenzyl)-1-(trans-4-formamidocyclohexyl)-2,3-dihydro-1H-benzimidazol-2-one NMR(CDCl$_3$, δ): 1.37–1.59 (2H, m), 1.92–2.04 (2H, m), 2.13–2.44 (4H, m), 3.96–4.11 (3H, m), 4.33–4.46 (1H, m), 5.00 (2H, s), 5.42 (1H, d, J=8 Hz), 7.08 (1H, d, J=2 Hz), 7.14 (1H, dd, J=8, 2 Hz), 7.21(1H, d, J=8 Hz), 7.36–7.46 (3H, m), 8.17 (1H, s).

(77) 1-[1-(Acetoxymethyl)cyclopentyl]-3-(3-chloro-4-methoxybenzyl)-5-cyano-2,3-dihydro-1H-benzimidazol-2-one NMR(CDCl$_3$, δ): 1.70–1.96 (7H, m), 2.34–2.47 (2H, m), 2.64–2.73 (2H, m), 3.89 (3H, s), 4.35 (2H, s), 4.95 (2H, s), 6.90 (1H, d, J=8 Hz), 7.04 (1H, s), 7.20 (1H, dd, J=8, 2 Hz), 7.28–7.36 (3H, m).

(78) 3-(3-Chloro-4-methoxybenzyl)-5-cyano-1-cyclopentyl-2,3-dihydro-1H-benzimidazol-2-one NMR(CDCl$_3$, δ): 1.69–1.84 (2H, m), 1.90–2.15 (6H, m), 3.89 (3H, s), 4.90 (1H, quint, J=7.5 Hz), 4.97 (2H, s), 6.90 (1H, d, J=8 Hz), 7.07–7.14 (2H, m), 7.20 (1H, dd, J=8, 2 Hz), 7.31–7.41 (2H, m).

(79) 3-(3-Chloro-4-methoxybenzyl)-5-cyano-1-(tetrahydro-4H-pyran-4-yl)-2,3-dihydro-1H-benzimidazol-2-one NMR(CDCl$_3$, δ): 1.76–1.86 (2H, m), 2.38–2.55 (2H, m), 3.51–3.64 (2H, m), 3.89 (3H, s), 4.11–4.20 (2H, m), 4.57–4.71(1H, m), 4.98 (2H, s), 6.90 (1H, d, J=8 Hz), 7.11 (1H, d, J=2 Hz), 7.20 (1H, dd, J=8, 2 Hz), 7.26–7.34 (2H, m), 7.40 (1H, dd, J=8, 2 Hz).

(80) 1-(cis-4-Acetoxycyclohexyl)-3-(3,4-dimethoxybenzyl)-5-cyano-2,3-dihydro-1H-benzimidazol-2-one NMR(DMSO-d$_6$, δ): 1.57–1.85 (4H, m), 1.85–2.01 (2H, m), 2.11 (3H, s), 2.26–2.49 (2H, m), 3.70 (3H, s), 3.72 (3H, s), 4.30–4.45 (1H, m), 4.90–5.04 (3H, m), 6.89 (2H, s-like), 7.05 (1H, s-like), 7.40 (1H, d, J=8 Hz), 7.55 (1H, dd, J=8, 2 Hz), 7.73 (1H, d, J=2 Hz).

(81) 5-Cyano-3-(3-cyano-4-methoxybenzyl)-1-(trans-4-hydroxycyclohexyl)-2,3-dihydro-1H-benzimidazol-2-one
mp. 191–193° C.

NMR(DMSO-d$_6$, δ): 1.26–1.44 (2H, m), 1.64–1.77 (2H, m), 1.87–2.00 (2H, m), 2.10–2.30 (2H, m), 3.49–3.64 (1H, m), 3.87 (3H, s), 4.16–4.32 (1H, m), 4.72 (1H, d, J=5 Hz), 5.01 (2H, s), 7.21 (1H, d, J=8 Hz), 7.49 (1H, d, J=8 Hz), 7.55 (1H, d, J=8 Hz), 7.64 (1H, dd, J=8, 2 Hz), 7.74–7.80 (2H, m).

(82) 3-(3-Bromo-4-methoxybenzyl)-1-(trans-4-hydroxycyclohexyl)-5-nitro-2,3-dihydro-1H-benzimidazol-2-one NMR(DMSO-d$_6$, δ): 1.29–1.46 (2H, m), 1.66–1.79 (2H, m), 1.87–2.01 (2H, m), 2.14–2.31 (2H, m), 3.50–3.65 (1H, m), 3.80 (3H, s), 4.20–4.36 (1H, m), 4.69 (1H, d, J=5 Hz), 5.11 (2H, s), 7.06 (1H, d, J=8 Hz), 7.34 (1H, dd, J=8, 2 Hz), 7.56–7.66 (2H, m), 8.00 (1H, dd, J=8, 2 Hz), 8.11 (1H, d, J=2 Hz).

(83) 3-(3-Fluoro-4-methoxybenzyl)-1-(trans-4-hydroxycyclohexyl)-5-nitro-2,3-dihydro-1H-benzimidazol-2-one NMR(DMSO-d$_6$, δ): 1.28–1.46 (2H, m), 1.70–1.80 (2H, m), 1.90–2.01 (2H, m), 2.14–2.31 (2H, m), 3.50–3.64 (1H, m), 3.79 (3H, s), 4.22–4.36 (1H, m), 4.70 (1H, d, J=5 Hz), 5.10 (2H, s), 7.09–7.19 (2H, m), 7.24 (1H, d, J=8 Hz), 7.61 (1H, d, J=8 Hz), 8.00 (1H, dd, J=8, 2 Hz), 8.08 (1H, d, J=2 Hz).

(84) 1-(trans-4-Hydroxycyclohexyl)-3-(4-methoxy-3-methylbenzyl)-5-nitro-2,3-dihydro-1H-benzimidazol-2-one NMR(CDCl$_3$, δ): 1.45–1.65 (2H, m), 1.86–1.99 (2H, m), 2.12–2.23 (5H, m), 2.23–2.40 (2H, m), 3.74–3.87 (4H, m), 4.26–4.41(1H, m), 5.00 (2H, s), 6.77 (1H, d, J=8 Hz), 7.10–7.21 (3H, m), 7.82 (1H, d, J=2 Hz), 8.02 (1H, dd, J=8, 2 Hz).

(85) 3-(4-Methoxy-3-methylbenzyl)-1-(trans-4-hydroxycyclohexyl)-5-trifluoromethyl-2,3-dihydro-1H-benzimidazol-2-one NMR(CDCl$_3$, δ): 1.46–1.64 (2H, m), 1.86–1.97 (2H, m), 2.11–2.23 (5H, m), 2.23–2.40 (2H, m), 3.74–3.88 (4H, m), 4.26–4.40 (1H, m), 4.97 (2H, s), 6.76 (1H, d, J=8 Hz), 7.10–7.18 (4H, m), 7.31 (1H, d, J=8 Hz).

(86) 3-(3-Cyano-4-methoxybenzyl)-1-(trans-4-hydroxycyclohexyl)-5-trifluoromethyl-2,3-dihydro-1H-benzimidazol-2-one NMR(CDCl$_3$, δ): 1.44–1.63 (2H, m), 1.88–1.99 (2H, m), 2.11–2.23 (4H, m), 2.33–2.40 (2H, m), 3.73–3.88 (2H, m), 3.92 (3H, s), 4.26–4.40 (1H, m), 5.01 (2H, s), 6.95 (1H, d, J=8 Hz), 7.07 (1H, s-like), 7.19 (1H, d, J=8 Hz), 7.37 (1H, d, J=8 Hz), 7.49–7.56 (2H, m).

(87) 3-(3-Chloro-4-methoxybenzyl)-5-cyano-1-cyclohexyl-2,3-dihydro-1H-benzimidazol-2-one NMR(CDCl$_3$, δ): 1.19–1.37 (1H, m), 1.37–1.55 (2H, m), 1.73–1.85 (2H, m), 1.85–2.02 (4H, m), 2.02–2.21 (2H, m), 3.89 (3H, s), 4.25–4.40 (1H, m), 4.97 (2H, s), 6.89 (1H, d, J=8 Hz), 7.08 (1H, d, J=2 Hz), 7.15–7.28 (2H, m), 7.30–7.42 (2H, m).

(88) 1-tert-Butyl-3-(3-chloro-4-methoxybenzyl)-5-cyano-2,3-dihydro-1H-benzimidazol-2-one NMR(CDCl$_3$, δ): 1.82 (9H, s), 3.89 (3H, s), 4.93 (2H, s), 6.89 (1H, d, J=8 Hz), 7.05 (1H, d, J=2 Hz), 7.17 (1H, dd, J=8,2 Hz), 7.27–7.34 (2H, m), 7.45 (1H, d, J=8 Hz).

(89) 3-(3-Chloro-4-methoxybenzyl)-5-cyano-1-cycloheptyl-2,3-dihydro-1H-benzimidazol-2-one NMR(CDCl$_3$, δ): 1.54–2.04 (10H, m), 2.11–2.27 (2H, m), 3.89 (3H, s), 4.44–4.57 (1H, m), 4.96 (2H, s), 6.89 (1H, d, J=8 Hz), 7.07 (1H, s), 7.13–7.23 (2H, m), 7.32 (1H, d, J=2 Hz), 7.36 (1H, dd, J=8, 2 Hz).

(90) 3-(3-Bromo-4-methoxybenzyl)-5-cyano-1-(trans-4-formamidocyclohexyl)-2,3-dihydro-1H-benzimidazol-2-one NMR(DMSO-d$_6$, δ): 1.31–1.54 (2H, m), 1.70–1.81(2H, m), 1.88–1.99 (2H, m), 2.18–2.35 (2H, m), 3.72–3.89 (4H, m), 4.21–4.36 (1H, m), 5.00 (2H, s), 7.07 (1H, d, J=8 Hz), 7.36 (1H, dd, J=8, 2Hz), 7.50 (1H, dd, J=8, 2Hz), 7.61–7.70 (2H, m), 7.79 (1H, s), 7.97 (1H, s), 8.04 (1H, d, J=8 Hz).

(91) 3-(3-Bromo-4-methoxybenzyl)-5-cyano-1-(tetrahydro-2H-pyran-4-yl)-2,3-dihydro-1H-benzimidazol-2-one NMR(DMSO-d$_6$, δ): 1.64–1.75 (2H, m), 2.30–2.46 (2H, m), 3.41–3.54 (2H, m), 3.94–4.04 (2H, m), 4.45–4.60 (1H, m), 5.00 (2H, s), 7.08 (1H, d, J=8 Hz), 7.37 (1H, dd, J=8, 2 Hz), 7.49–7.59 (2H, m), 7.65 (1H, d, J=2 Hz), 7.80 (1H, s).

(92) 1-[(S)-2-Acetoxy-1-ethylethyl]-3-(3-chloro-4-methoxybenzyl)-5-cyano-2,3-dihydro-1H-benzimidazol-2-one NMR(CDCl$_3$, δ): 0.93 (3H, t, J=7.5 Hz), 1.86–2.03 (4H, m), 2.07–2.26 (1H, m), 3.89 (3H, s), 4.38–4.64 (3H, m), 4.95 (1H, d, J=15 Hz), 5.03 (1H, d, J=15 Hz), 6.89 (1H, d, J=8 Hz), 7.09 (1H, d, J=2 Hz), 7.11 (1H, d, J=8 Hz), 7.17 (1H, dd, J=8, 2 Hz), 7.28 (1H, d, J=2 Hz), 7.38 (1H, dd, J=8, 2 Hz).

(93) 1-[(R)-2-Acetoxy-1-ethylethyl]-3-3-(3-chloro-4-methoxybenzyl)-5-cyano-2,3-dihydro-1H-benzimidazol-2-one NMR(CDCl$_3$, δ): 0.93 (3H, t, J=7.5 Hz), 1.85–2.04 (4H, m), 2.07–2.27 (1H, m), 3.89 (3H, s), 4.39–4.64 (3H, m), 4.95 (1H, d, J=15 Hz), 5.04 (1H, d, J=15 Hz), 6.90 (1H, d, J=8Hz), 7.08 (1H, d, J=2 Hz), 7.12 (1H, d, J=8 Hz), 7.17 (1H, dd, J=8, 2 Hz), 7.28 (1H, d, J=2 Hz), 7.38 (1H, dd, J=8, 2 Hz).

(94) 1-[1-(tert-Butoxycarbonyl)piperidin-4-yl]-3-(3-chloro-4-methoxybenzyl)-5-cyano-2,3-dihydro-1H-benzimidazol-2-one NMR(DMSO-d$_6$, δ): 1.42 (9H, s), 1.68–1.79 (2H, m), 2.09–2.29 (2H, m), 2.75–3.00 (2H, m), 3.80 (3H, s), 4.02–4.15 (2H, m), 4.36–4.53 (1H, m), 4.98 (2H, s), 7.10 (1H, d, J=8 Hz), 7.30 (1H, dd, J=8, 2 Hz), 7.45–7.56 (3H, m), 7.76 (1H, s).

(95) 3-(3-Chloro-4-methoxybenzyl)-5-cyano-1-(t-3,t-4-isopropylidenedioxy-r-1-cyclohexyl)-2,3-dihydro-1H-benzimidazol-2-one NMR(CDCl$_3$, δ): 1.39 (3H, s), 1.58 (3H, s), 1.75–1.91 (1H, m), 1.91–2.27 (4H, m), 2.55–2.68 (1H, m), 3.90 (3H, s), 4.24–4.34 (1H, m), 4.44–4.50 (1H, m), 4.50–4.64 (1H, m), 4.96 (2H, s), 6.90 (1H, d, J=8 Hz), 7.06–7.15 (2H, m), 7.20 (1H, d, J=8 Hz), 7.32 (1H, s), 7.40 (1H, d, J=8 Hz).

(96) 3-(3-Chloro-4-methoxybenzyl)-5-cyano-1-(c-3,c-4-isopropylidenedioxy-r-1-cyclohexyl)-2,3-dihydro-1H-benzimidazol-2-one NMR(CDCl$_3$, δ): 1.41 (3H, s), 1.62 (3H, s), 1.68–1.79 (1H, m), 1.83–2.00 (1H, m), 2.05–2.20 (1H, m), 2.20–2.51

(3H, m), 3.90 (3H, s), 4.25–4.43 (3H, m), 4.98 (2H, s), 6.90 (1H, d, J=8 Hz), 7.11 (1H, s), 7.15–7.29 (2H, m), 7.32 (1H, s), 7.39 (1H, d, J=8 Hz).

(97) 3-(3-Cyano-4-methoxybenzyl)-1-(trans-4-hydroxycyclohexyl)-5-nitro-2,3-dihydro-1H-benzimidazol-2-one mp. 122–124° C.

NMR(DMSO-$d_6$, δ): 1.28–1.46(2H, m), 1.68–1.81(2H, m), 1.89–2.00(2H, m), 2.13–2.30(2H, m), 3.51–3.65(1H, m), 3.88(3H, s), 4.20–4.35(1H, m), 4.70(1H, d, J=4.0 Hz), 5.13 (2H, s), 7.24(1H, d, J=9.0 Hz), 7.61(1H, d, J=9.0 Hz), 7.64(1H, dd, J=9.0, 2.0 Hz), 7.77(1H, d, J=2.0 Hz), 8.01(1H, dd, J=9.0, 2.0 Hz), 8.13(1H, d, J=2.0 Hz).

(98) 1-(3-Chloro-4-methoxybenzyl)-3-(trans-4-hydroxycyclohexyl)-6-methoxycarbonyl-2,3-dihydro-1H-imidazo[4,5-b]pyridin-2-one mp. 146–148° C.

NMR(DMSO-$d_6$, δ): 1.25–1.42(2H, m), 1.68–1.79(2H, m), 1.92–2.00(2H, m), 2.25–2.48(2H, m), 3.44–3.58(1H, m), 3.81(3H, s), 3.85(3H, s), 4.25–4.40(1H, m), 4.70(1H, d, J=4.5 Hz), 5.08(2H, s), 7.11(1H, d, J=8.5 Hz), 7.27(1H, dd, J=8.5, 2.0 Hz), 7.47(1H, d, J=2.0 Hz), 7.94(1H, d, J=2.0 Hz), 8.60(1H, d, J=2.0 Hz).

(99) 1-[trans-4-(N-tert-Butoxycarbonylamino)cyclohexyl]-3-(3-chloro-4-methoxybenzyl)-5-trifluoromethyl-2,3-dihydro-1H-benzimidazol-2-one mp. 185.5–187° C.

NMR(DMSO-$d_6$, δ): 1.30–1.46(2H, m), 1.40(9H, s), 1.68–1.77(2H, m), 1.86–1.96(2H, m), 2.15–2.32(2H, m), 3.35–3.48(1H, m), 3.81(3H, s), 4.16–4.31(1H, m), 5.06(2H, s), 6.83(1H, d, J=7.5 Hz), 7.10(1H, d, J=8.5 Hz), 7.28(1H, dd, J=8.5, 2.5 Hz), 7.36(1H, dd, J=8.5, 2.0 Hz), 7.46(1H, d, J=2.5 Hz), 7.60(1H, d, J=2.0 Hz), 7.63(1H, d, J=8.5 Hz).

(100) 1-(3-Bromo-4-methoxybenzyl)-6-cyano-3-(trans-4-hydroxycyclohexyl)-2,3-dihydro-1H-imidazo[4,5-b]pyridin-2-one mp. 114–116° C.

NMR(DMSO-$d_6$, δ): 1.21–1.40(2H, m), 1.67–1.77(2H, m), 1.89–2.00(2H, m), 2.26–2.43(2H, m), 3.41–3.55(1H, m), 3.81(3H, s), 4.21–4.35(1H, m), 4.70(1H, d, J=4.5 Hz), 4.98(2H, s), 7.08(1H, d, J=8.5 Hz), 7.38(1H, dd, J=8.5, 2.5 Hz), 7.66(1H, d, J=2.5 Hz), 8.11(1H, d, J=2.0 Hz), 8.48(1H, d, J=2.0 Hz).

(101) 6-Cyano-3-(trans-4-hydroxycyclohexyl)-1-(4-methoxy-3-methylbenzyl)-2,3-dihydro-1H-imidazo[4,5-b]pyridin-2-one mp. 168–169° C.

NMR(DMSO-$d_6$, δ): 1.22–1.40(2H, m), 1.67–1.77(2H, m), 1.89–1.99(2H, m), 2.10(3H, s), 2.27–2.44(2H, m), 3.42–3.55(1H, m), 3.74(3H, s), 4.22–4.36(1H, m), 4.70(1H, d, J=4.5 Hz), 4.94(2H, s), 6.88(1H, d, J=8.0 Hz), 7.18(1H, d, J=2.0 Hz), 7.21(1H, dd, J=8.0, 2.0 Hz), 8.02(1H, d, J=2.0 Hz), 8.47(1H, d, J=2.0 Hz).

(102) 6-Cyano-1-(3-cyano-4-methoxybenzyl)-3-(trans-4-hydroxycyclohexyl)-2,3-dihydro-1H-imidazo[4,5-b]pyridin-2-one mp. 133–134° C.

NMR(DMSO-$d_6$, δ): 1.21–1.42(2H, m), 1.68–1.80(2H, m), 1.90–1.99(2H, m), 2.26–2.43(2H, m), 3.39–3.51(1H, m), 3.89(3H, s), 4.21–4.33(1H, m), 4.70(1H, d, J=4.5 Hz), 5.01(2H, s), 7.23(1H, d, J=8.5 Hz), 7.69(1H, dd, J=8.5, 2.5 Hz), 7.81(1H, d, J=2.5 Hz), 8.09(1H, d, J=2.0 Hz), 8.48(1H, d, J=2.0 Hz).

(103) 3-((S)-1-tert-Butoxycarbonylpyrrolidin-3-yl)-1-(3-chloro-4-methoxybenzyl)-6-trifluoromethyl-2,3-dihydro-1H-imidazo[4,5-b]pyridin-2-one mp. 87–89° C.

NMR(DMSO-$d_6$, δ): 1.40(6H, s), 1.43(3H, s), 2.12–2.27 (1H, m), 2.53–2.73(1H, m), 3.29–3.40(1H, m), 3.52–3.69 (2H, m), 3.75–3.83(1H, m), 3.83(3H, s), 5.07 (2H, s), 5.07–5.19(1H, m), 7.12(1H, d, J=8.5 Hz), 7.35(1H, dd, J=8.5, 2.5 Hz), 7.53(1H, d, J=2.5 Hz), 7.57(1H, s), 8.34(1H, s).

MS m/z: 527($M^+$+1).

(104) 3-(Benzimidazol-5-yl)-1-(3-chloro-4-methoxybenzyl)-6-cyano-2,3-dihydro-1H-imidazo[4, 5-b]pyridin-2-one mp 163–166° C.

NMR(DMSO-$d_6$, δ): 3.84(3H, s), 5.10(2H, s), 7.14(1H, d, J=8 Hz), 7.36–7.49(2H, m), 7.61(1H, d, J=1 Hz), 7.67(1H, br d, J=8 Hz), 7.79(1H, br d, J=8 Hz), 7.87(1H, br s), 8.19(1H, br s), 8.35(1H, s), 8.45(1H, br s).

MS (ESI) m/z: 429($M^+$−1).

(105) 1-(3-Chloro-4-methoxybenzyl)-3-(1H-indol-5-yl)-6-cyano-2,3-dihydro-1H-imidazo[4,5-b]pyridin-2-one mp. 281–282° C.

NMR(DMSO-$d_6$, δ): 3.85(3H, s), 5.12(2H, s), 6.99(1H, d, J=2.5 Hz), 7.16(1H, d, J=8.5 Hz), 7.47(1H, dd, J=8.5, 2.0 Hz), 7.58–7.65(2H, m), 7.85(1H, d, J=2.5 Hz), 7.98(1H, d, J=2.0 Hz), 8.09(1H, d, J=8.5 Hz), 8.21(1H, d, J=2.0 Hz), 8.48(1H, d, J=2.0 Hz).

(106) 5-Cyano-3-(3-formyl-4-methoxybenzyl)-1-(trans-4-hydroxycyclohexyl)-1,3-dihydro-2H-benzimidazol-2-one NMR(CDCl$_3$, δ): 1.46–1.66 (2H, br), 1.88–2.05 (2H, br), 2.14–2.40 (4H, br), 3.77–3.92 (1H, m), 3.93 (3H, s), 4.26–4.40 (1H, m), 5.02 (2H, s), 6.97–7.06 (2H, m), 7.15 (1H, d, J=8 Hz), 7.38 (1H, d, J=8 Hz), 7.48 (1H, dd, J=2 Hz, 8 Hz), 7.71 (1H, d, J=2 Hz), 10.44 (1H, s).

(107) 5-Cyano-1-(trans-4-hydroxycyclohexyl)-3-(4-methoxy-3-methoxycarbonylbenzyl)-1,3-dihydro-2H-benzimidazol-2-one NMR(DMSO-$d_6$, δ): 1.28–1.48 (2H, br), 1.65–1.80 (2H, br), 1.88–2.02 (2H, br), 2.14–2.33 (2H, br), 3.52–3.66 (1H, br), 3.77 (3H, s), 3.78 (3H, s), 4.18–4.33 (1H, br), 4.68 (1H, d, J=4 Hz), 5.03 (2H, s), 7.11(1H, d, J=8 Hz), 7.46–7.60 (3H, m), 7.67 (1H, d, J=2 Hz), 7.77 (1H, d, J=2 Hz), (108) 3-(3-Acetyl-4-methoxybenzyl)-1-(trans-4-hydroxycyclohexyl)-5-nitro-1,3-dihydro-2H-benzimidazol-2-one NMR(DMSO-$d_6$, δ): 1.32–1.48 (2H, br), 1.67–1.82 (2H, br), 1.88–2.04 (2H, br), 2.16–2.33 (2H, br), 2.49 (3H, s), 3.50–3.66 (1H, br), 3.86 (3H, s), 4.23–4.38 (1H, br), 4.70 (1H, d, J=7 Hz), 5.14 (2H, s), 7.16 (1H, d, J=8 Hz), 7.51 (1H, dd, J=2 Hz, 8 Hz), 7.61 (2H, m), 8.00 (1H, dd, J=2 Hz, 8 Hz), 8.09 (1H, d, J=2 Hz).

(109) 1-(trans-4-Hydroxycyclohexyl)-3-(4-methoxy-3-nitrobenzyl)-5-nitro-1,3-dihydro-2H-benzimidazol-2-one NMR(DMSO-$d_6$, δ): 1.30–1.48 (2H, br), 1.68–1.83 (2H, br), 1.92–2.03 (2H, br), 2.16–2.33 (2H, br), 3.52–3.67 (1H, br), 3.89 (3H, s), 4.23–4.37 (1H, br), 4.70 (1H, d, J=4 Hz), 5.19 (2H, s), 7.35 (1H, d, J=8 Hz), 7.61 (1H, d, J=8Hz), 7.62 (1H, dd, J=2 Hz, 8 Hz), 7.94 (1H, d, J=2 Hz), 8.01 (1H, dd, J=2 Hz, 8 Hz), 8.17 (1H, d, J=2 Hz).

(110) 1-(Benzimidazol-5-yl)-3-(3-chloro-4-methoxybenzyl)-5-cyano-2,3-dihydro-1H-benzimidazole-2-one NMR(DMSO-$d_6$, δ): 3.84 (3H, s), 5.11 (2H, s), 7.09 (1H, d, J=8 Hz), 7.16 (1H, d, J=8 Hz), 7.35 (1H, dd, J=8,2 Hz), 7.45 (1H, dd, J=8,2 Hz), 7.51 (1H, dd, J=8,2 Hz), 7.59 (1H, d, J=2 Hz), 7.75–7.82 (2H, m), 7.86 (1H, d, J=2 Hz), 8.38 (1H, s).

(111) 1-(3-Acetoxypropyl)-3-(3-chloro-4-methoxybenzyl)-5-cyano-2,3-dihydro-1H-benzimidazole-2-one NMR(CDCl$_3$, δ): 2.02 (3H, s), 2.14 (2H, m), 3.89 (3H, s), 4.05 (2H, t, J=5 Hz), 4.13 (2H, t, J=5 Hz), 4.98 (2H, s), 6.90

(1H, d, J=8 Hz), 7.04 (1H, d, J=8 Hz), 7.09 (1H, d, J=2 Hz), 7.20 (1H, dd, J=8, 2 Hz), 7.32 (1H, d, J=2 Hz), 7.41 (1H, dd, J=8, 2 Hz).

(112) 3-(3-Chloro-4-methoxybenzyl)-1-[2-(N,N-dimethylamino)ethyl]-5-cyano-2,3-dihydro-1H-benzimidazole-2-one NMR(CDCl$_3$, δ): 2.31(6H, s), 2.66 (2H, t, J=7 Hz), 3.89 (3H, s), 4.04 (2H, t, J=7 Hz), 4.98 (2H, s), 6.88 (1H, d, J=8 Hz), 7.05–7.11 (2H, m), 7.18 (1H, dd J=8,2 Hz), 7.30 (1H, d, J=2 Hz), 7.40 (1H, d, J=8 Hz).

EXAMPLE 3

To a solution of 3-(2-acetoxy-1,1-dimethylethyl)-6-trifluoromethyl-2,3-dihydro-1H-imidazo[4,5-b]pyridin-2-one (150 mg) in anhydrous N,N-dimethylformamide (1.5 mL) was added portionwise sodium hydride (20.8 mg, 60% dispersion in mineral oil) at 5° C. under nitrogen atmosphere, and the mixture was stirred at room temperature for 30 minutes. After adding 3-chloro-4-methoxybenzylbromide (117 mg), the mixture was stirred at room temperature for 4 hours. After adding tetrahydrofuran (2 mL), methanol (1 mL) and 1N-sodium hydroxide solution (1 mL), the mixture was refluxed for an hour. After cooling to room temperature, the mixture was concentrated in vacuo. The residue was partitioned between ethyl acetate and water. The separated organic layer was washed successively with water, 1N-hydrochloric acid, an aqueous saturated sodium hydrogencarbonate solution and brine. The organic layer was dried over magnesium sulfate and evaporated in vacuo. The residual solid was washed with diethyl ether to give 1-(3-chloro-4-methoxybenzyl)-3-(1,1-dimethyl-2-hydroxyethyl)-6-trifluoromethyl-2,3-dihydro-1H-imidazo[4,5-b]pyridin-2-one (161.6 mg) as an orange solid.

mp. 195–197° C.

NMR(DMSO-d$_6$, δ): 1.73(6H, s), 3.82(3H, s), 3.88(2H, d, J=6.5 Hz), 4.89(1H, t, J=6.5 Hz), 5.03(2H, s), 7.12(1H, d, J=8.5 Hz), 7.31(1H, dd, J=8.5, 2.5 Hz), 7.49(1H, d, J=2.5 Hz), 7.91(1H, d, J=1.5 Hz), 8.35(1H, d, J=1.5 Hz).

MS m/z: 430(M$^+$+1).

EXAMPLE 4

The following compounds described in (1) to (8) were obtained in a manner similar to Example 3.

(1) 1-[1-(Acetoxymethyl)cyclopentyl]-3-(3-chloro-4-methoxybenzyl)-5-trifluoromethyl-2,3-dihydro-1H-benzimidazol-2-one NMR(DMSO-d$_6$, δ): 1.56–1.77(4H, m), 2.19–2.33(2H, m), 2.45–2.55(2H, m), 3.55(2H, d, J=5.5Hz), 3.81(3H, s), 4.99(1H, t, J=6.0 Hz), 5.03(2H, s), 7.10(1H, d, J=8.5 Hz), 7.25–7.33(2H, m), 7.46(1H, d, J=2.0 Hz), 7.48(1H, d, J=8.5 Hz), 7.49(1H, s).

MS m/z: 453(M$^+$−1).

(2) 1-(3-Chloro-4-methoxybenzyl)-3-((R)-2-hydroxy-1-methylethyl)-6-trifluoromethyl-2,3-dihydro-1H-imidazo[4,5-b]pyridin-2-one mp. 154.5–155° C.

NMR(DMSO-d$_6$, δ): 1.44(3H, d, J=7.0 Hz), 3.59–3.69 (1H, m), 3.82(3H, s), 3.98–4.09(1H, m), 4.52–4.66(1H, m), 4.91(1H, t, J=6.0 Hz), 5.07(2H, s), 7.12(1H, d, J=8.5 Hz), 7.33(1H, dd, J=8.5, 2.0 Hz), 7.50(1H, d, J=2.0 Hz), 7.95(1H, d, J=2.0 Hz), 8.38(1H, d, J=2.0 Hz).

MS m/z: 416(M$^+$+1).

(3) 3-(3-Chloro-4-methoxybenzyl)-1-(trans-4-hydroxycyclohexyl)-5-methylsulfonyl-2,3-dihydro-1H-benzimidazol-2-one mp. 265–265.5° C.

NMR(DMSO-d$_6$, δ): 1.28–1.45(2H, m), 1.65–1.77(2H, m), 1.90–2.01(2H, m), 2.14–2.32(2H, m), 3.17(3H, s), 3.51–3.65(1H, m), 3.81(3H, s), 4.20–4.34(1H, m), 4.70(1H, d, J=4.5 Hz), 5.07(2H, s), 7.11(1H, d, J=8.5 Hz), 7.25(1H, dd, J=8.5, 2.5 Hz), 7.46(1H, d, J=2.5 Hz), 7.58(1H, d, J=8.5 Hz), 7.63(1H, d, J=8.5 Hz), 7.74(1H, s).

(4) 3-(3-Chloro-4-methoxybenzyl)-1-((R)-2-hydroxy-1-methylethyl)-5-trifluoromethyl-2,3-dihydro-1H-benzimidazol-2-one mp. 108–109° C.

NMR(DMSO-d$_6$, δ): 1.42(3H, d, J=7.0 Hz), 3.60–3.70 (1H, m), 3.81(3H, s), 3.84–3.95(1H, m), 4.46–4.60(1H, m), 4.97(1H, t, J=5.5 Hz), 5.07(2H, s), 7.11(1H, d, J=8.5 Hz), 7.29(1H, d, J=8.5Hz), 7.37(1H, d, J=8.5Hz), 7.47(1H, s), 7.48(1H, d, J=8.5 Hz), 7.57(1H, s).

MS m/z: 413(M$^+$−1).

(5) 1(3-Chloro-4-methoxybenzyl)-6-cyano-3-(trans-4-hydroxycyclohexyl)-2,3-dihydro-1H-imidazo[4,5-b]pyridin-2-one mp. 176–176.5° C.

NMR(DMSO-d$_6$, δ): 1.22–1.40(2H, m), 1.67–1.77(2H, m), 1.89–2.00(2H, m), 2.25–2.45(2H, m), 3.42–3.55(1H, m), 3.82(3H, s), 4.21–4.35(1H, m), 4.68(1H, d, J=5.5 Hz), 4.98(2H, s), 7.12(1H, d, J=8.5 Hz), 7.35(1H, dd, J=8.5, 2.5 Hz), 7.52(1H, d, J=2.5 Hz), 8.10(1H, d, J=2.0 Hz), 8.48(1H, d, J=2.0 Hz).

(6) 5-Benzoyl-3-(3-chloro-4-methoxybenzyl)-1-(trans-4-hydroxycyclohexyl)-2,3-dihydro-1H-benzimidazol-2-one mp. 160.5–162° C.

NMR(DMSO-d$_6$, δ): 1.29–1.46(2H, m), 1.69–1.80(2H, m), 1.90–2.01(2H, m), 2.16–2.33(2H, m), 3.50–3.64(1H, m), 3.83(3H, s), 4.20–4.34(1H, m), 4.70(1H, d, J=4.0 Hz), 5.05(2H, s), 7.11(1H, d, J=8.5 Hz), 7.24(1H, dd, J=8.5, 2.5 Hz), 7.41(1H, d, J=2.5 Hz), 7.46(1H, t, J=8.5 Hz), 7.50–7.55 (3H, m), 7.63(2H, d, J=8.5 Hz), 7.66(2H, d, J=7.5 Hz).

(7) 3-(3-Chloro-4-methoxybenzyl)-1-(2-hydroxyethyl)-5-trifluoromethyl-2,3-dihydro-1H-benzimidazol-2-one mp. 106–107° C.

NMR(DMSO-d$_6$, δ): 3.67(2H, q, J=5.5 Hz), 3.81(3H, s), 3.97(2H, t, J=5.5 Hz), 4.90(1H, t, J=5.5 Hz), 5.08(2H, s), 7.11(1H, d, J=8.5 Hz), 7.31(1H, dd, J=8.5, 2.5 Hz), 7.41(2H, s), 7.48(1H, d, J=2.5 Hz), 7.58(1H, s).

(8) 1-(3-Chloro-4-methoxybenzyl)-6-cyano-3-((R)-2-hydroxy-1-methylethyl)-2,3-dihydro-1H-imidazo[4,5-b]pyridin-2-one mp. 164–165° C.

NMR(DMSO-d$_6$, δ): 1.43(3H, d, J=7.0 Hz), 3.56–3.69 (1H, m), 3.82(3H, s), 3.95–4.07(1H, m), 4.53–4.65(1H, m), 4.91(1H, t, J=6.0 Hz), 5.00(2H, s), 7.12(1H, d, J=8.5 Hz), 7.35(1H, dd, J=8.5, 2.0 Hz), 7.51(1H, d, J=2.0 Hz), 8.08(1H, d, J=2.0 Hz), 8.47(1H, d, J=2.0 Hz).

EXAMPLE 5

To a solution of 5-cyano-3-(3,4-dimethoxybenzyl)-1-(2, 2-dimethyl-1,3-dioxan-5-yl)-2,3-dihydro-1H-benzimidazol-2-one (140 mg) in tetrahydrofuran (2 mL) was added 1 N-hydrochloric acid (1.5 mL), and the mixture was stirred at ambient temperature for 8 hours. After evaporation of the solvent, the residue was partitioned between water and a mixture of chloroform and methanol (10:1). The separated organic layer was washed with brine and dried over magnesium sulfate. After evaporation of solvent, the residue was subjected to a preparative thin-layer chromatography eluting with a mixture of chloroform and methanol (10:1). The obtained substance was triturated with diethyl ether to give 5-cyano-3-(3,4-dimethoxybenzyl)-1-[2-hydroxy-1-(hydroxymethyl)ethyl]-2,3-dihydro-1H-benzimidazol-2-one (92 mg) as powders.

NMR(DMSO-d$_6$, δ): 3.64–3.83 (8H, m),3.83–3.99 (2H, m),4.38–4.50 (1H, m), 4.93 (2H, t, J=5 Hz), 5.00 (1H, s, J=2 Hz), 6.89 (2H, s-like), 7.02 (1H, s-like), 7.40–7.53 (2H, m), 7.66 (1H, s-like).

EXAMPLE 6

The following compounds described in (1) and (4) were obtained in a manner similar to Example 5.

(1) 3-(4-Chloro-3-methoxybenzyl)-5-cyano-1-[2-hydroxy-1-(hydroxymethyl)ethyl]-2,3-dihydro-1H-benzimidazol-2-one NMR(DMSO-d$_6$, δ): 3.70–3.85 (5H, m), 3.85–3.98 (2H, m),4.38–4.50 (1H, m), 4.94 (2H, t, J=5 Hz), 5.08 (2H, s), 6.88 (1H, dd, J=8, 2 Hz), 7.20 (1H, d, J=2 Hz), 7.36 (1H, d, J=8 Hz), 7.42–7.53 (2H, m), 7.68 (1H, s-like).

(2) 3-(3-Chloro-4-methoxybenzyl)-5-cyano-1-[2-hydroxy-1-(hydroxymethyl)ethyl]-2,3-dihydro-1H-benzimidazol-2-one NMR(DMSO-d$_6$, δ): 3.70–3.84 (5H, m),3.84–3.98 (2H, m), 4.36–4.50 (1H, m), 4.93 (2H, t, J=5 Hz), 5.01 (2H, s), 7.12 (1H, d, J=8 Hz), 7.35 (1H, dd, J=8, 2 Hz), 7.40–7.52 (3H, m), 7.73 (1H, s-like).

(3) 3-(3-Chloro-4-methoxybenzyl)-5-cyano-1-(t-3,t4-dihydroxy-r-1-cyclohexyl)-2,3-dihydro-1H-benzimidazol-2-one NMR(DMSO-d$_6$, δ): 1.55–1.89 (4H, m), 2.07–2.44 (2H, m), 3.62 (1H, br), 3.81(3H, s), 3.90 (1H, br), 4.53 (1H, d, J=6 Hz), 4.56–4.70 (2H, m), 4.99 (2H, s), 7.11 (1H, d, J=8 Hz), 7.31 (1H, dd, J=8, 2 Hz), 7.46–7.66 (3H, m), 7.78 (1H, d, J=2 Hz).

(4) 3-(3-Chloro-4-methoxybenzyl)-5-cyano-1-(c-3,c-4-dihydroxy-r-1-cyclohexyl)-2,3-dihydro-1H-benzimidazol-2-one NMR(DMSO-d$_6$, δ): 1.35–1.65 (3H, m), 1.74–1.85 (1H, m), 2.21–2.49 (2H, m), 3.51–3.62 (1H, m), 3.78 (1H, br), 3.81(3H, s), 4.27–4.42 (1H, m), 4.53 (1H, d, J=3 Hz), 4.67 (1H, d, J=6 Hz), 5.00 (2H, s), 7.11(1H, d, J=8 Hz), 7.34 (1H, dd, J=8, 2 Hz), 7.39 (1H, d, J=8 Hz), 7.49 (1H, d, J=2 Hz), 7.56 (1H, dd, J=8, 2 Hz), 7.79 (1H, d, J=2 Hz).

EXAMPLE 7

4N-Hydrogen chloride solution in ethyl acetate (5 mL) was added to a suspension of 1-[(S)-1-tert-butoxycarbonylpyrrolidin-3-yl]-3-(3-chloro-4-methoxybenzyl)-5-cyano-2,3-dihydro-1H-benzimidazol-2-one (520 mg) in ethyl acetate (5 mL) at 0° C. The mixture was stirred at ambient temperature for 4 hours. The reaction mixture was concentrated in vacuo. To the residue was added an aqueous saturated sodium bicarbonate solution and ethyl acetate. The separated organic layer was washed successively with water and brine and dried over magnesium sulfate. After evaporation of the solvent, the residue was triturated with diethyl ether to give 3-(3-chloro-4-methoxybenzyl)-5-cyano-1-[(S)-pyrrolidin-3-yl]-2,3-dihydro-1H-benzimidazol-2-one (287 mg) as amorphous powders.

NMR(CDCl$_3$, δ): 2.02–2.17 (1H, m), 2.25–2.45 (1H, m), 2.94–3.06 (1H, m), 3.22–3.46 (3H, m), 3.89 (3H, s), 4.97 (2H, s), 4.99–5.11 (1H, m), 6.91(1H, d, J=8 Hz), 7.10 (1H, s), 7.20 (1H, dd, J=8,2 Hz), 7.33 (1H, d, J=2 Hz), 7.40 (1H, dd, J=8, 2 Hz), 7.51 (1H, d, J=8 Hz).

EXAMPLE 8

The following compounds described in (1) to (4),were obtained in a manner similar to Example 7.

(1) 3-(3-Chloro-4-methoxybenzyl)-5-cyano-1-[(R)-pyrrolidin-3-yl]-2,3-dihydro-1H-benzimidazol-2-one NMR(CDCl$_3$, δ): 2.01–2.16 (1H, m), 2.22–2.37 (1H, m), 2.92–3.04 (1H, m), 3.21–3.46 (3H, m), 3.90 (3H, s), 4.97 (2H, s), 4.99–5.11 (1H, m), 6.90 (1H, d, J=8 Hz), 7.10 (1H, d, J=2 Hz), 7.20 (1H, dd, J=8, 2 Hz), 7.33 (2H, d, J=2 Hz), 7.40 (1H, dd, J=8, 2 Hz), 7.51 (1H, d, J=8 Hz).

(2) 1-(trans-4-Aminocyclohexyl)-3-(3-chloro-4-methoxybenzyl)-5-cyano-2,3-dihydro-1H-benzimidazol-2-one NMR(DMSO-d$_6$, δ): 1.14–1.31 (2H, m), 1.57–1.69 (4H, m), 1.69–1.94 (2H, m), 2.10–2.30 (2H, m), 2.61–2.77 (1H, m), 3.81 (3H, s), 4.15–4.30 (1H, m), 4.99(2H, s), 7.11 (1H, d, J=8 Hz), 7.32 (1H, dd, J=8, 2 Hz), 7.46–7.59 (3H, m), 7.78 (1H, s-like).

(3) 3-(3-Chloro-4-methoxybenzyl)-5-cyano-1-(piperidin-4-yl)-2,3-dihydro-1H-benzimidazol-2-one NMR(DMSO-d$_6$, δ): 1.57–1.70 (2H, m), 2.09–2.30 (2H, m), 2.52–2.65 (2H, m), 3.00–3.11 (2H, m), 3.81 (3H, s), 4.26–4.41 (1H, m), 5.00 (2H, s), 7.11 (1H, d, J=8 Hz), 7.33 (1H, dd, J=8, 2 Hz), 7.48–7.60 (3H, m), 7.79 (1H, s).

(4) 1-(trans-4-Aminocyclohexyl)-3-(3-chloro-4-methoxybenzyl)-5-trifluoromethyl-2,3-dihydro-1H-benzimidazol-2-one mp. 167–168.5° C.

NMR(DMSO-d$_6$, δ): 1.22–1.40(2H, m), 1.67–1.79(2H, m), 1.87–1.98(2H, m), 2.15–2.31(2H, m), 2.76–2.90(1H, m), 3.81(3H, s), 4.17–4.33(1H, m), 5.06(2H, s), 7.11(1H, d, J=8.5 Hz), 7.28(1H, dd, J=8.5, 2.5 Hz), 7.38(1H, d, J=8.5 Hz), 7.46(1H, d, J=2.5 Hz), 7.57(1H, d, J=8.5 Hz), 7.61(1H, s).

MS m/z: 454(M$^+$+1).

EXAMPLE 9

A solution of 3-(3-chloro-4-methoxybenzyl)-5-cyano-1-[(S)-pyrrolidin-3-yl]-2,3-dihydro-1H-benzimidazol-2-one (80 mg) in ethyl formate (2 mL) was heated under reflux for 10 hours. After evaporation of the solvent, the residue was subjected to a preparative thin-layer chromatography eluting with a mixture of chloroform and methanol (15:1) to give 3-(3-chloro-4-methoxybenzyl)-5-cyano-1-[(S)-1-formylpyrrolidin-3-yl]-2,3-dihydro-1H-benzimidazol-2-one (52 mg) as amorphous powders.

NMR(CDCl$_3$, δ): 2.32–2.46 (1H, m), 2.50–2.71 (1H, m), 3.55–3.72 (1H, m), 3.84–4.16 (6H, m), 4.97 (2H, s), 5.03–5.24 (1H, m), 6.90 (1H, d, J=8 Hz), 7.00–7.10 (1H, m), 7.10–7.16 (1H, m), 7.16–7.24 (1H,m), 7.30–7.36 (1H, m), 7.38–7.45 (1H, m), 8.30–8.35 (1H, m).

EXAMPLE 10

The following compounds described in (1) and (2) were obtained in a manner similar to Example 9.

(1) 3-(3-Chloro-4-methoxybenzyl)-5-cyano-1-[(R)-1-formylpyrrolidin-3-yl]-2,3-dihydro-1H-benzimidazol-2-one NMR(CDCl$_3$, δ): 2.32–2.46 (1H, m), 2.51–2.71(1H, m), 3.55–3.73 (1H, m), 3.84–4.17 (6H, m), 4.97 (2H, s), 5.04–5.24 (1H, m), 6.90 (1H, d, J=8 Hz), 6.99–7.10 (1H, m), 7.10–7.15 (1H, m), 7.15–7.25 (1H, m), 7.30–7.35 (1H, m), 7.37–7.45 (1H, m), 8.30–8.35 (1H, m).

(2) 3-(3-Chloro-4-methoxybenzyl)-5-cyano-1-(1-formylpiperidin-4-yl)-2,3-dihydro-1H-benzimidazol-2-one NMR(DMSO-d$_6$, δ): 1.75–1.89 (2H, m), 2.04–2.35 (2H, m), 2.67–2.81 (1H, m), 3.14–3.25 (1H, m), 3.74–3.89 (4H, m), 4.30–4.40 (1H, m), 4.51–4.65 (1H, m), 5.00 (2H, s), 7.11 (1H, d, J=8 Hz), 7.34 (1H, dd, J=8, 2 Hz), 7.49 (1H, d, J=2 Hz), 7.50–7.60 (2H, m), 7.79 (1H, s), 8.04 (1H, s).

EXAMPLE 11

Methanesulfonyl chloride (27 mg) and triethylamine (24 mg) were added to a solution of 3-(3-chloro-4- methoxybenzyl)-5-cyano-1-[(S)-pyrrolidin-3-yl]-2,3-dihydro-1H-benzimidazol-2-one (75 mg) in dichloromethane (2 mL). The reaction mixture was stirred at 0° C. for 3 hours. The reaction mixture was poured into water and extracted with a mixture of chloroform and methanol (5:1). The organic layer was washed with an aqueous saturated sodium chloride solution, dried over magnesium sulfate, and concentrated in vacuo. The obtained crystals were suspended in hot ethyl acetate and then cooled with stirring. The resulting precipitate was collected by filtration and washed with ethyl acetate to give 3-(3-chloro-4-methoxybenzyl)-5-cyano-1-[(S)-1-methanesulfonylpyrrolidin-3-yl]-2,3-dihydro-1H-benzimidazol-2-one (76 mg) as colorless crystals.

NMR(DMSO-$d_6$, δ): 2.23–2.36 (1H, m), 2.36–2.54 (1H, m), 3.01 (3H, s), 3.29–3.41 (1H, m), 3.55–3.72 (3H, m), 3.82 (3H, s), 5.01 (2H, s), 5.13–5.26 (1H, m), 7.11 (1H, d, J=8 Hz), 7.35 (1H, dd, J=8, 2 Hz), 7.47–7.53 (2H, m), 7.60 (1H, d, J=8 Hz), 7.80 (1H, s).

EXAMPLE 12

The following compounds described in (1) to (3) were obtained in a manner similar to Example 11.
(1) 3-(3-Chloro-4-methoxybenzyl)-5-cyano-1-[(R)-1-methanesulfonylpyrrolidin-3-yl]-2,3-dihydro-1H-benzimidazol-2-one NMR(DMSO-$d_6$, δ): 2.23–2.37 (1H, m), 2.37–2.54 (1H, m), 3.01(3H, s), 3.26–3.40 (1H, m), 3.56–3.73 (1H, m), 3.82 (3H, s), 5.01 (2H, s), 5.13–5.17 (1H, m), 7.12 (1H, d, J=8 Hz), 7.35 (1H, dd, J=8, 2 Hz), 7.47–7.54 (2H, m), 7.60 (1H, d, J=8 Hz), 7.80 (1H, s).
(2) 3-(3-Chloro-4-methoxybenzyl)-5-cyano-1-(trans-4-methanesulfonylaminocyclohexyl)-2,3-dihydro-1H-benzimidazol-2-one NMR(CDCl$_3$, δ): 1.36–1.55 (2H, m), 1.69–1.81 (2H, m), 1.96–2.09 (2H, m), 2.95 (3H, s), 3.35 (1H, br), 3.81 (3H, s), 4.19–4.32 (1H, m), 5.00 (2H, s), 7.06–7.15 (2H, m), 7.33 (1H, dd, J=8, 2 Hz), 7.47–7.55 (2H, m), 7.65 (1H, d, J=8 Hz), 7.79 (1H, s).
(3) 3-(3-Chloro-4-methoxybenzyl)-5-cyano-1-(1-methanesulfonylpiperidin-4-yl)-2,3-dihydro-1H-benzimidazol-2-one NMR(CDCl$_3$, δ): 1.94–2.04 (2H, m), 2.41–2.60 (2H, m), 2.82–2.96 (5H, m), 3.90 (3H, s), 4.00–4.10 (2H, m), 4.48–4.64 (1H, m), 4.98 (2H, s), 6.90 (1H, d J=8 Hz), 7.13 (1H, d, J=2 Hz), 7.20 (1H, dd, J=8, 2Hz), 7.25 (1H, d, J=8 Hz), 7.32 (1H, d, J=2 Hz), 7.41 (1H, dd, J=8, 2 Hz).

EXAMPLE 13

A solution of potassium cyanate (40 mg) in water (1 mL) was added to a mixture of 1-(trans-4-aminocyclohexyl)-3-(3-chloro-4-methoxybenzyl)-5-cyano-2,3-dihydro-1H-benzimidazol-2-one (100 mg) and 1N-hydrochloric acid (0.25 mL) in 1,4-dioxane (1.4 mL). The reaction mixture was stirred at ambient temperature for 20 hours. The mixture was partitioned between ethyl acetate and water. The separated organic layer was washed with brine, dried over magnesium sulfate, and concentrated in vacuo. The resulting residue was triturated with diethyl ether and washed with isopropyl alcohol to give 1-(trans-4-ureidocyclohexyl)-3-(3-chloro-4-methoxybenzyl)-5-cyano-2,3-dihydro-1H-benzimidazol-2-one (71mg) as powders.

NMR(DMSO-$d_6$, δ): 1.21–1.40 (2H, m), 1.67–1.79 (2H, m), 1.89–2.01 (2H, m), 2.14–2.33 (2H, m), 3.50 (1H, br), 3.81(3H, s), 4.20–4.35 (1H, m), 5.00 (2H, s), 5.36 (2H, s), 5.89 (1H, d, J=8 Hz), 7.11(1H, d, J=8 Hz ), 7.32 (1H, dd, J=8, 2 Hz), 7.46–7.53 (2H, m), 7.64 (1H, d, J=8 Hz), 7.78 (1H, s).

EXAMPLE 14

The following compounds described in (1) and (2) were obtained in a manner similar to Example 13.
(1) 1-(1-carbamoylpiperidin-4-yl)-3-(3-chloro-4-methoxybenzyl)-5-cyano-2,3-dihydro-1H-benzimidazol-2-one NMR(DMSO-$d_6$, δ): 1.66–1.76 (2H, m), 2.09–2.30 (2H, m), 2.75–2.37 (2H, m), 3.81(3H, s), 4.05–4.15 (2H, m), 4.39–4.52 (1H, m), 4.99 (2H, s), 6.02 (2H, s), 7.11(1H, d, J=8 Hz), 7.34 (1H, dd, J=8, 2 Hz), 7.44–7.56 (3H, m, 7.79 (1H, d, J=2 Hz).
(2) 1-(trans-4-Ureidocyclohexyl)-3-(3-chloro-4-methoxybenzyl)-5-trifluoromethyl-2,3-dihydro-1H-benzimidazol-2-one
mp. 164–165.5° C.

NMR(DMSO-$d_6$, δ): 1.23–1.41(2H, m), 1.69–1.79(2H, m), 1.90–2.00(2H, m), 2.16–2.34(2H, m), 3.42–3.56(1H, m), 3.81(3H, s), 4.21–4.35(1H, m), 5.07(2H, s), 5.37(2H, s), 5.90(1H, d, J=7.5 Hz), 7.11(1H, d, J=8.5 Hz), 7.28(1H, dd, J=8.5, 2.0 Hz), 7.37(1H, dd, J=8.5, 2.0 Hz), 7.47(1H, d, J=2.0 Hz), 7.60(1H, d, J=2.0 Hz), 7.61(1H, d, J=8.5 Hz).

EXAMPLE 15

A mixture of 1-(trans-4-aminocyclohexyl)-3-(3-chloro-4-methoxybenzyl)-5-cyano-2,3-dihydro-1H-benzimidazol-2-one (90 mg) and sulfamide (42 mg) in ethylene glycol dimethyl ether (3 mL) was refluxed overnight. The mixture was concentrated in vacuo, and the residue was partitioned between chloroform and water. The separated organic layer was washed with an aqueous saturated sodium chloride solution, dried over magnesium sulfate, and concentrated in vacuo. The residue was subjected to a preparative thin-layer chromatography eluting with a mixture of chloroform and methanol (10:1). The obtained crystals were collected by filtration and washed with diethyl ether to give 1-(trans-4-aminosulfonamidocyclohexyl)-3-(3-chloro-4-methoxybenzyl)-5-cyano-2,3-dihydro-1H-benzimidazol-2-one (41 mg) as powders.

NMR(DMSO-$d_6$, δ): 1.32–1.50 (2H, m), 1.70–1.81 (2H, m), 2.04–2.16 (2H, m), 2.16–2.34 (2H, m), 3.25 (1H, br), 3.81 (3H, s), 4.15–4.30 (1H, m), 4.99 (2H, s), 6.50 (2H, s), 6.61 (1H, d, J=8 Hz), 7.11 (1H, d, J=8 Hz), 7.31 (1H, dd, J=8, 2 Hz), 7.46–7.54 (2H, m), 7.61 (1H, d, J=8 Hz), 7.78 (1H, s).

EXAMPLE 16

1-(1-Sulfamoylpiperidin-4-yl)-3-(3-chloro-4-methoxybenzyl)-5-cyano-2,3-dihydro-1H-benzimidazol-2-one was obtained in a manner similar to Example 15.

NMR(DMSO-$d_6$, δ): 1.80–1.91 (2H, m), 2.31–2.49 (2H, m), 2.66–2.81 (2H, m), 3.59–3.74 (2H, m), 3.82 (3H, s), 4.31–4.47 (1H, m), 5.01 (2H, s), 6.90 (2H, br s), 7.11 (1H, d, J=8 Hz), 7.32 (1H, dd, J=8, 2 Hz), 7.54 (2H, s-like), 7.77 (1H, s).

EXAMPLE 17

A mixture of 1-(trans-4-aminocyclohexyl)-3-(3-chloro-4-methoxybenzyl)-5-cyano-2,3-dihydro-1H-benzimidazol-2-one (100 mg) and methyl isocyanate (17 mg) in dichloromethane (3 mL) was stirred at 0° C. for 2 hours under nitrogen atmosphere. The mixture was partitioned between water and a mixture of chloroform and methanol (5:1). The separated organic layer was washed with water and dried over magnesium sulfate. After evaporation of the solvent, the residue was subjected to a preparative thin-layer chromatography eluting with a mixture of chloroform and methanol (10:1). The obtained substance was triturated with diethyl ether to give 3-(3-chloro-4-methoxybenzyl)-5-cyano-1-[trans-4-(3-methylureido)cyclohexyl]-2,3-dihydro-1H-benzimidazol-2-one (69 mg) as colorless powders.

NMR(DMSO-$d_6$, δ): 1.21–1.40 (2H, m), 1.67–1.77 (2H, m), 1.88–1.98 (2H, m), 2.16–2.34 (2H, m), 2.54 (3H, d, J=5 Hz), 3.45–3.60 (1H, m), 3.81 (3H, s), 4.20–4.34 (1H, m), 4.99 (2H, s), 5.56–5.64 (1H, m), 5.79 (1H, d, J=7.5 Hz), 7.11 (1H, d, J=8 Hz), 7.32 (1H, dd, J=8, 2 Hz), 7.46–7.82 (2H, m), 7.63 (1H, d, J=8 Hz), 7.77 (1H, d, J=2 Hz).

EXAMPLE 18

A mixture of 3-(trans-4-acetoxycyclohexyl)-1-(3,4-dimethoxybenzyl)-6-trifluoromethyl-2,3-dihydro-1H-imidazo[4,5-b]pyridin-2-one (125 mg) in a mixture of tetrahydrofuran (1 mL), methanol (0.5 mL) and 1N-sodium hydroxide (0.507 mL) was refluxed for an hour. After cooling to room temperature, the mixture was concentrated in vacuo. Water was added to the residue, and the resulting precipitate was collected by filtration. The obtained solid was washed with water and subjected to a preparative silica gel column chromatography eluting with 5% methanol in chloroform. The obtained solid was washed with a mixture of diethyl ether and diisopropyl ether to give 1-(3,4-dimethoxybenzyl)-3-(trans-4-hydroxycyclohexyl)-6-trifluoromethyl-2,3-dihydro-1H-imidazo[4,5-b]pyridin-2-one (62.9 mg) as a colorless solid.

mp. 128–130° C.

NMR(DMSO-$d_6$, δ): 1.22–1.41(2H, m), 1.67–1.77(2H, m), 1.90–2.00(2H, m), 2.25–2.47(2H, m), 3.43–3.56(1H, m), 3.70(3H, s), 3.71(3H, s), 4.25–4.39(1H, m), 4.69(1H, d, J=4.5 Hz), 5.04(2H, s), 6.86(1H, dd, J=8.5, 2.5 Hz), 6.89 (1H, d, J=8.5 Hz), 7.07(1H, d, J=2.5 Hz), 7.93(1H, d, J=2.5 Hz), 8.38(1H, d, J=2.5 Hz).

EXAMPLE 19

The following compounds described in (1) to (26) were obtained in a manner similar to Example 18.

(1) 3-(3,4-Dimethoxybenzyl)-1-(trans-2-hydroxycyclopentyl)-5-trifluoromethyl-2,3-dihydro-1H-benzimidazol-2-one NMR(DMSO-$d_6$, δ): 1.51–1.64(1H, m), 1.73–1.87(2H, m), 1.91–2.17(3H, m), 3.70(3H, s), 3.71(3H, s), 4.38–4.59 (2H, m), 5.05(1H, d, J=4.5 Hz), 5.05(2H, s), 6.84(1H, dd, J=8.0, 2.5 Hz), 6.90(1H, d, J=8.0 Hz), 7.08(1H, d, J=2.5 Hz), 7.37(1H, d, J=8.0 Hz), 7.40(1H, d, J=8.0 Hz), 7.57(1H, s).

(2) 1-(3-Chloro-4-methoxybenzyl)-3-(trans-4-hydroxycyclohexyl)-6-trifluoromethyl-2,3-dihydro-1H-imidazo[4,5-b]pyridin-2-one mp. 121–123° C.

NMR(DMSO-$d_6$, δ): 1.23–1.41(2H, m), 1.67–1.80(2H, m), 1.90–2.02(2H, m), 2.25–2.47(2H, m), 3.43–3.56(1H, m), 3.81(3H, s), 4.24–4.37(1H, m), 4.70(1H, brs), 5.05(2H, s), 7.12(1H, d, J=8.5 Hz), 7.32(1H, dd, J=8.5, 2.5 Hz), 7.51(1H, d, J=2.5 Hz), 7.99(1H, d, J=2.5 Hz), 8.39(1H, d, J=2.5 Hz).

(3) 1-(3,4-Dichlorobenzyl)-3-(trans-4-hydroxycyclohexyl)-6-trifluoromethyl-2,3-dihydro-1H-imidazo[4,5-b]pyridin-2-one mp. 170–171.5° C.

NMR(DMSO-$d_6$, δ): 1.25–1.40(2H, m), 1.70–1.80(2H, m), 1.90–1.99(2H, m), 2.26–2.47(2H, m), 3.43–3.56(1H, m), 4.22–4.36(1H, m), 4.69(1H, d, J=4.5 Hz), 5.13(2H, s), 7.31(1H, dd, J=8.0, 2.0 Hz), 7.61(1H, d, J=8.0 Hz), 7.70(1H, d, J=2.0 Hz), 8.00(1H, d, J=2.0 Hz), 8.41(1H, d, J=2.0 Hz).

(4) 3-(3,4-Dimethoxybenzyl)-1-(trans-4-hydroxycyclohexyl)-5-methyl-2,3-dihydro-1H-benzimidazol-2-one mp. 174–175° C.

NMR(DMSO-$d_6$, δ): 1.26–1.44(2H, m), 1.60–1.72(2H, m), 1.88–2.00(2H, m), 2.12–2.29(2H, m), 2.27(3H, s), 3.50–3.64(1H, m), 3.69(3H, s), 3.70(3H, s), 4.12–4.25(1H, m), 4.66(1H, d, J=4.5 Hz), 4.91(2H, s), 6.77(1H, dd, J=8.0, 2.0 Hz), 6.81(1H, d, J=8.0 Hz), 6.87(1H, d, J=8.0 Hz), 6.95(1H, s), 6.99(1H, d, J=2.0 Hz), 7.21(1H, d, J=8.0 Hz).

MS m/z: 397(M$^+$+1).

(5) 5-Carboxy-3-(3-chloro-4-methoxybenzyl)-1-(trans-4-hydroxycyclohexyl)-2,3-dihydro-1H-benzimidazol-2-one mp. 275–276° C.

NMR(DMSO-$d_6$, δ): 1.28–1.46(2H, m), 1.66–1.78(2H, m), 1.89–2.01(2H, m), 2.15–2.32(2H, m), 3.50–3.64(1H, m), 3.81(3H, s), 4.17–4.31(1H, m), 4.68(1H, d, J=4.5 Hz), 5.05(2H, s), 7.10(1H, d, J=8.5 Hz), 7.22(1H, dd, J=8.5, 2.5 Hz), 7.40(1H, d, J=2.5 Hz), 7.46(1H, d, J=8.5 Hz), 7.64(1H, s), 7.68(1H, d, J=8.5 Hz).

MS m/z: 429(M$^+$−1).

(6) 5-Cyano-3-(3,4-dimethoxybenzyl)-1-(1,1-dimethyl-2-hydroxyethyl)-2,3-dihydro-1H-benzimidazol-2-one NMR(DMSO-$d_6$, δ): 1.68 (6H, s), 3.70 (3H, s), 3.71(3H, s), 3.82 (2H, d, J=5 Hz), 4.97 (2H, s), 5.06 (1H, t, J=5 Hz), 6.82–6.93 (2H, m), 7.03 (1H, d, J=2 Hz), 7.41 (1H, dd, J=8, 2 Hz), 7.60–7.70 (2H, m).

(7) 3-(4-Chloro-3-methoxybenzyl)-5-cyano-1-(1,1-dimethyl-2-hydroxyethyl)-2,3-dihydro-1H-benzimidazol-2-one NMR(DMSO-$d_6$, δ): 1.69 (6H, s), 3.78–3.87 (5H, m), 5.01–5.09 (3H, m), 6.83 (1H, dd, J=8, 2 Hz), 7.22 (1H, d, J=2 Hz), 7.36 (1H, d, J=8 Hz), 7.44 (1H, dd, J=8, 2 Hz), 7.63–7.77 (2H, m).

(8) 3-(3-Chloro-4-methoxybenzyl)-5-cyano-1-(1,1-dimethyl-2-hydroxyethyl)-2,3-dihydro-1H-benzimidazol-2-one NMR(DMSO-$d_6$, δ): 1.68 (6H, s), 3.78–3.85 (5H, m), 4.98 (2H, s), 5.05 (1H, t, J=5 Hz), 7.11 (1H, d, J=8 Hz), 7.30 (1H, dd, J=8, 2 Hz), 7.42 (1H, dd, J=8, 2 Hz), 7.47 (1H, d, J=2 Hz), 7.65 (1H, d, J=8 Hz), 7.70 (1H, d, J=2 Hz).

(9) 3-(4-Chloro-3-methoxybenzyl)-5-cyano-1-[(R)-2-hydroxy-1-methylethyl]-2,3-dihydro-1H-benzimidazol-2-one NMR(CDCl$_3$, δ): 1.55 (3H, d, J=7.5 Hz), 3.05 (1H, dd, J=7, 4 Hz), 3.88 (3H, s), 3.99–4.16 (2H, m), 4.46–4.59 (1H, m), 5.03 (2H, s), 6.80 (1H, dd, J=8, 2 Hz), 6.90 (1H, d, J=2 Hz), 7.14 (1H, d, J=2 Hz), 7.16 (1H, d, J=8 Hz), 7.33 (1H, d, J=8 Hz), 7.42 (1H, dd, J=8, 2 Hz).

(10) 3-(3-Chloro-4-methoxybenzyl)-5-cyano-1-[(R)-2-hydroxy-1-methylethyl]-2,3-dihydro-1H-benzimidazol-2-one NMR(CDCl$_3$, δ): 1.55 (3H, d, J=7.5 Hz), 3.10 (1H, dd, J=7, 4 Hz), 3.90 (3H, s), 4.00–4.16 (2H, m), 4.45–4.58 (1H, m), 4.98 (2H, s), 6.90 (1H, d, J=8 Hz), 7.11 (1H, d, J=2 Hz), 7.14–7.24 (2H, m), 7.32 (1H, d, J=2 Hz), 7.41 (1H, dd, J=8, 2 Hz).

(11) 3-(4-Chloro-3-methoxybenzyl)-5-cyano-1-[(S)-2-hydroxy-1-methylethyl]-2,3-dihydro-1H-benzimidazol-2-one NMR(CDCl$_3$, δ): 1.55 (3H, d, J=7.5 Hz), 3.05 (1H, dd, J=7, 4 Hz), 3.88 (3H, s), 3.99–4.16 (2H, m), 4.46–4.59 (1H, m), 5.03 (2H, s), 6.81(1H, dd, J=8, 2 Hz), 6.90 (1H, d, J=2 Hz), 7.13 (1H, d, J=2 Hz), 7.16 (1H, d, J=8 Hz), 7.33 (1H, d, J=8 Hz), 7.42 (1H, dd, J=8, 2 Hz).

(12) 3-(3-Chloro-4-methoxybenzyl)-5-cyano-1-[(S)-2-hydroxy-1-methylethyl]-2,3-dihydro-1H-benzimidazol-2-one NMR(CDCl$_3$, δ): 1.55 (3H, d, J=7.5 Hz), 3.10 (1H, dd, J=7, 4 Hz), 3.90 (3H, s), 4.00–4.16 (2H, m), 4.45–4.58 (1H, m), 4.98 (2H, s), 6.90 (1H, d, J=8 Hz), 7.11 (1H, d, J=2 Hz), 7.14–7.23 (2H, m), 7.32 (1H, d, J=2 Hz), 7.41 (1H, dd, J=8, 2 Hz).

(13) 1-(1,1-Dimethyl-2-hydroxyethyl)-3-(3,4-dimethoxybenzyl)-5-trifluoromethyl-2,3-dihydro-1H-benzimidazol-2-one NMR(CDCl$_3$, δ): 1.65 (6H, s), 3.86 (6H, s), 4.04 (2H, d, J=7.5 Hz), 7.74 (1H, t, J=7.5 Hz), 5.01 (2H, s), 6.79–6.93 (3H, m), 7.21 (1H, s), 7.35 (1H, d, J=8 Hz), 7.43 (1H, d, J=8 Hz).

(14) 3-(4-Chloro-3-methoxybenzyl)-1-(1,1-dimethyl-2-hydroxyethyl)-5-trifluoromethyl-2,3-dihydro-1H-benzimidazol-2-one NMR(CDCl$_3$, δ): 1.65 (6H, s), 3.88 (3H, s), 4.05 (2H, d, J=7.5 Hz), 4.64 (1H, t, J=7.5 Hz), 5.04 (2H, s), 6.80 (1H, dd, J=8, 2 Hz), 6.92 (1H, d, J=2 Hz), 7.17 (1H, s), 7.30 (1H, d, J=8 Hz), 7.36 (1H, d, J=8 Hz), 7.44 (1H, d, J=8 Hz).

(15) 3-(3-Chloro-4-methoxybenzyl)-1-(1,1-dimethyl-2-hydroxyethyl)-5-trifluoromethyl-2,3-dihydro-1H-benzimidazol-2-one NMR(CDCl$_3$, δ): 1.65 (8H, s), 3.89 (3H, s), 4.05 (2H, d, J=7.5 Hz), 4.67 (1H, t, J=7.5 Hz), 4.99 (2H, s), 6.89 (1H, d, J=8 Hz), 7.15 (1H, s), 7.18 (1H, dd, J=8, 2 Hz), 7.33–7.40 (2H, m), 7.45 (1H, d, J=8 Hz).

(16) 3-(3-Chloro-4-methoxybenzyl)-1-(cis-4-hydroxycyclohexyl)-5-cyano-2,3-dihydro-1H-benzimidazol-2-one ( NMR(CDCl$_3$, δ): 1.64–1.80 (4H, m), 1.94–2.05 (2H, m), 2.46–2.64 (2H, m), 3.89 (3H, s), 4.20 (1H, br s), 4.40–4.54 (1H, m), 4.98 (2H, s), 6.90 (1H, d, J=8 Hz), 7.09 (1H, s), 7.20 (1H, dd, J=8, 2 Hz), 7.30–7.40 (3H, m).

(17) 5-Cyano-1-(trans-4-hydroxycyclohexyl)-3-piperonyl-2,3-dihydro-1H-benzimidazol-2-one NMR(CDCl$_3$, δ): 1.45–1.61 (2H, m), 1.86–1.98 (2H, m), 2.10–2.39 (4H, m), 3.72–3.86 (1H, m), 4.24–4.38 (1H, m), 4.95 (2H, s), 5.95 (2H, s), 6.75–6.84 (3H, m), 7.11 (1H, d, J=2 Hz), 7.14 (1H, d, J=8 Hz), 7.36 (1H, dd, J=8, 2 Hz).

(18) 3-(2-Chlorobenzyl)-1-(trans-4-hydroxycyclohexyl)-5-cyano-2,3-dihydro-1H-benzimidazol-2-one NMR(DMSO-d$_6$, δ): 1.29–1.45 (2H, m), 1.67–1.79 (2H, m), 1.89–2.01 (2H, m), 2.14–2.32 (2H, m), 3.51–3.64 (1H, m), 4.19–4.34 (1H, m), 4.68 (1H, d, J=4 Hz), 5.15 (2H, s), 6.94 (1H, d, J=8 Hz), 7.25–7.38 (2H, m), 7.49–7.60 (3H, m), 7.64 (d, J=8 Hz, 1H).

(19) 3-(3-Chlorobenzyl)-1-(trans-4-hydroxycyclohexyl)-5-cyano-2,3-dihydro-1H-benzimidazol-2-one NMR(DMSO-d$_6$, δ): 1.27–1.45 (2H, m), 1.66–1.76 (2H, m), 1.89–1.99 (2H, m), 2.12–2.30 (2H, m), 3.50–3.64 (1H, m), 4.17–4.32 (1H, m), 4.67 (1H, d, J=4 Hz), 5.07 (2H, s), 7.25–7.32 (1H, m), 7.32–7.41(2H, m), 7.45 (1H, s), 7.51 (1H, dd, J=8, 2 Hz), 7.59 (1H, d, J=8 Hz), 7.76 (1H, d, J=2 Hz).

(20) 3-(4-Chlorobenzyl)-1-(trans-4-hydroxycyclohexyl)-5-cyano-2,3-dihydro-1H-benzimidazol-2-one NMR(DMSO-d$_6$, δ): 1.45–1.61 (2H, m), 1.86–1.98 (2H, m), 2.11–2.39 (4H, m), 3.73–3.87 (1H, m), 4.24–4.38 (1H, m), 5.01 (2H, s), 7.08 (1H, d, J=2 Hz), 7.15 (1H, d, J=8 Hz), 7.24 (2H, d, J=8 Hz), 7.32 (2H, d, J=8 Hz), 7.38 (1H, d, J=8 Hz).

(21) 3-(3-Chloro-4-methoxybenzyl)-5-cyano-1-[1-(hydroxymethyl)cyclopentyl]-2,3-dihydro-1H-benzimidazol-2-one NMR(DMSO-d$_6$, δ): 1.71–1.88 (2H, m), 1.88–2.04 (2H, m), 2.21–2.36 (2H, m), 2.36–2.49 (2H, m), 3.28 (1H, t, J=7.5 Hz), 3.84–3.94 (5H, m), 4.95 (2H, s), 6.90 (1H, d, J=8 Hz), 7.10 (1H, d, J=2 Hz), 7.19 (1H, d, J=8 Hz), 7.26–7.37 (3H, m).

(22) 3-(3,4-Dimethoxybenzyl)-1-(cis-4-hydroxycyclohexyl)-5-cyano-2,3-dihydro-1H-benzimidazol-2-one NMR(DMSO-d$_6$, δ): 1.43–1.66 (4H, m), 1.75–1.86 (2H, m), 3.70 (3H, s), 3.72 (3H, s), 3.90 (1H, br), 4.24–4.38 (1H, m), 4.58 (1H, d, J=4 Hz), 4.99 (2H, s), 6.84–6.93 (2H, m), 7.05 (1H, s-like), 7.41(1H, d, J=8 Hz), 7.55 (1H, dd, J=8, 2 Hz), 7.73 (1H, d, J=2 Hz).

(23) 3-(3-Chloro-4-methoxybenzyl)-5-cyano-1-[(S)-1-ethyl-2-hydroxyethyl]-2,3-dihydro-1H-benzimidazol-2-one NMR(CDCl$_3$, δ): 0.944 (3H, t, J=7.5 Hz), 1.93–2.14 (2H, m), 2.96–3.08 (1H, m), 3.89 (3H, s), 3.94–4.06 (1H, m), 4.06–4.21 (1H, m), 4.21–4.34 (1H, m), 4.99 (2H, s), 6.90 (1H, d, J=8 Hz), 7.10 (1H, d, J=2 Hz), 7.13–7.20 (2H, m), 7.30 (1H, d, J=2 Hz), 7.40 (1H, dd, J=8, 2 Hz).

(24) 3-(3-Chloro-4-methoxybenzyl)-5-cyano-1-[(R)-1-ethyl-2-hydroxyethyl]-2,3-dihydro-1H-benzimidazol-2-one NMR(CDCl$_3$, δ): 0.94 (3H, t, J=7.5 Hz), 1.94–2.14 (2H, m), 2.98–3.06 (1H, m), 3.89 (1H, s), 3.97–4.07 (1H, m), 4.10–4.21(1H, m), 4.22–4.34 (1H, m), 4.99 (2H, s), 6.90 (1H, d, J=8 Hz), 7.11 (1H, d, J=2 Hz), 7.14–7.20 (2H, m), 7.30 (1H, d, J=2 Hz), 7.40 (1H, dd, J=8, 2 Hz).

(25) 6-Carboxy-1-(3-chloro-4-methoxybenzyl)-3-(trans-4-hydroxycyclohexyl)-2,3-dihydro-1H-imidazo[4,5-b]pyridin-2-one mp. 262–262.5° C.

NMR(DMSO-d$_6$, δ): 1.23–1.41(2H, m), 1.68–1.80(2H, m), 1.90–2.01(2H, m), 2.32–2.48(2H, m), 3.44–3.58(1H, m), 3.81(3H, s), 4.25–4.39(1H, m), 4.69(1H, d, J=4.5 Hz), 5.07(2H, s), 7.12(1H, d, J=8.5 Hz), 7.27(1H, dd, J=8.5, 2.0 Hz), 7.47(1H, d, J=2.0 Hz), 7.90(1H, d, J=2.0 Hz), 8.58(1H, d, J=2.0 Hz).

MS m/z: 430(M$^+$–1).

(26) 3-(3-Chloro-4-methoxybenzyl)-1-(3-hydroxypropyl)-5-cyano-2,3-dihydro-1H-benzimidazole-2-one NMR(DMSO-d$_6$, δ): 1.80 (2H, m), 3.36–3.55 (2H, m), 3.82 (3H, s), 3.96 (2H, t, J=7 Hz), 4.66 (1H, t, J=4 Hz), 5.02 (2H, s), 7.10 (1H, d, J=8 Hz), 7.32 (1H, dd, J=8,2 Hz), 7.40 (1H, d, J=8 Hz), 7.48 (1H, d, J=2 Hz), 7.56 (1H, dd, J=8,2 Hz), 7.75 (1H, d, J=2 Hz).

EXAMPLE 20

A mixture of 5-carboxy-3-(3-chloro-4-methoxybenzyl)-1-(trans-4-hydroxycyclohexyl)-2,3-dihydro-1H-benzimidazol-2-one (72 mg), ammonium hydroxide (0.1 mL, 28% NH$_3$ in water), 1-(3-dimethylaminopropyl)-3-ethylcarbodiimide hydrochloride (35.2 mg) and 1-hydroxybenzotriazole (27.1 mg) in anhydrous dimethylformamide (1 mL) was stirred at ambient temperature for 4 hours. The mixture was partitioned between water and ethyl acetate. The separated organic layer was washed successively with an aqueous saturated sodium bicarbonate solution, water, 1N-hydrochloric acid and brine. The organic layer was dried over magnesium sulfate and evaporated in vacuo. The residue was subjected to a preparative silica gel column chromatography eluting with 5% methanol in chloroform. The obtained solid was washed with acetonitrile to give 5-carbamoyl-3-(3-chloro-4-methoxybenzyl)-1-(trans-4-hydroxycyclohexyl)-2,3-dihydro-1H-benzimidazol-2-one (217.9 mg) as a colorless solid.

mp. 291.5–292° C.

NMR(DMSO-d$_6$, δ): 1.26–1.46(2H, m), 1.67–1.78(2H, m), 1.90–2.02(2H, m), 2.15–2.35(2H, m), 3.52–3.65(1H, m), 3.81(3H, s), 4.19–4.31(1H, m), 4.69(1H, brs), 5.05(2H, s), 7.11(1H, d, J=8.5 Hz), 7.23(1H, dd, J=8.5, 2.0 Hz), 7.40(1H, d, J=2.0 Hz), 7.47(1H, d, J=8.5 Hz), 7.65(1H, s), 7.68(1H, d, J=8.5 Hz).

MS m/z: 429(M$^+$–1).

EXAMPLE 21

The following compounds described in (1) and (2) were obtained in a manner similar to Example 20.

(1) 1-(3-Chloro-4-methoxybenzyl)-6-furfurylcarbamoyl-3-(trans-4-hydroxycyclohexyl)-2,3-dihydro-1H-imidazol[4,5-b]pyridin-2-one mp. 193–194.5° C.

NMR(DMSO-$d_6$, δ): 1.24–1.42(2H, m), 1.67–1.79(2H, m), 1.90–2.01(2H, m), 2.32–2.48(2H, m), 3.44–3.58(1H, m), 3.82(3H, s), 4.23–4.37(1H, m), 4.49(2H, d, J=5.5 Hz), 4.70(1H,br s), 5.02(2H, s), 6.28(1H, m), 6.40(1H, m), 7.1 1 (1H, d, J=8.5 Hz), 7.27(1H, dd, J=8.5, 2.0 Hz), 7.46(1H, s), 7.59(1H, m), 7.91(1H, d, J=2.0 Hz), 8.53(1H, s), 8.99(1H, t, J=5.5 Hz).

(2) 1-(3-Chloro-4-methoxybenzyl)-6-(3-picolylcarbamoyl)-3-(trans-4-hydroxycyclohexyl)-2,3-dihydro-1H-imidazo[4,5-b]pyridin-2-one mp. 134–135° C.

NMR(DMSO-$d_6$, δ): 1.26–1.42(2H, m), 1.68–1.79(2H, m), 1.90–2.01(2H, m), 2.32–2.52(2H, m), 3.45–3.58(1H, m), 3.82(3H, s), 4.24–4.37(1H, m), 4.51(2H, d, J=5.5 Hz), 4.70(1H,brs), 5.03(2H, s), 7.11(1H, d, J=8.5 Hz), 7.27(1H, dd, J=8.5, 2.0 Hz), 7.37(1H, dd, J=7.5, 5.5 Hz), 7.46(1H, s), 7.72(1H, m), 7.93(1H, d, J=2.0 Hz), 8.47(1H, d, J=5.5 Hz), 8.56(2H, s), 9.13(1H, t, J=5.5 Hz).

MS m/z: 522($M^+$+1).

EXAMPLE 22

The following compounds described in (1) to (3) were obtained in a manner similar to Preparation 16.

(1) 1-(trans-4-Acetoxycyclohexyl)-3-(3,4-dimethoxybenzyl)-5-nitro-2,3-dihydro-1H-benzimidazol-2-one mp. 207–207.5° C.

NMR(DMSO-$d_6$, δ): 1.49–1.66(2H, m), 1.75–1.87(2H, m), 1.98–2.10(2H, m), 2.02(3H, s), 2.23–2.42(2H, m), 3.70 (3H, s), 3.72(3H, s), 4.33–4.46(1H, m), 4.75–4.88(1H, m), 5.09(2H, s), 6.83(1H, dd, J=8.5, 2.5 Hz), 6.90(1H, d, J=8.5 Hz), 7.05(1H, d, J=2.5 Hz), 7.70(1H, d, J=9.0 Hz), 7.99(1H, dd, J=9.0, 2.0 Hz), 8.06(1H, d, J=2.0 Hz).

(2) 1-(trans-4-Acetamidocyclohexyl)-3-(3-chloro-4-methoxybenzyl)-5-cyano-2,3-dihydro-1H-benzimidazol-2-one NMR(CDCl$_3$, δ): 1.32–1.49 (2H, m), 1.89–2.03 (5H, m), 2.15–2.38 (4H, m), 3.84–4.01 (4H, m), 4.35–4.49 (1H, m), 4.97 (2H, s), 5.36 (1H, d, J=8 Hz), 6.89 (1H, d, J=8 Hz), 7.10 (1H, d, J=2 Hz), 7.16–7.24 (2H, m), 7.31 (1H, d, J=2 Hz), 7.38 (1H, dd, J=8, 2 Hz).

(3) 1-(1-Acetylpiperidin-4-yl)-3-(3-chloro-4-methoxybenzyl)-5-cyano-2,3-dihydro-1H-benzimidazol-2-one NMR(CDCl$_3$, δ): 1.86–2.01 (2H, m), 2.18 (3H, s), 2.20–2.41(2H, m), 2.60–2.75 (1H, m), 3.17–3.31 (1H, m), 3.90 (3H, s), 3.96–4.09 (1H, m), 4.50–4.65 (1H, m), 4.84–5.03 (3H, m), 6.90 (1H, d, J=8 Hz), 7.07 (1H, s), 7.15 (1H, d, J=8 Hz), 7.20 (1H, dd, J=8, 2 Hz), 7.32 (1H, d, J=2 Hz), 7.37 (1H, dd, J=8, 2 Hz).

EXAMPLE 23

To a mixture of 1-(3-chloro-4-methoxybenzyl)-6-cyano-3-(trans-4-hydroxycyclohexyl)-2,3-dihydro-1H-imidazo[4,5-b]pyridin-2-one (500 mg), acetic acid (76.9 mg) and diethyl azodicarboxylate (221 mg) in anhydrous tetrahydrofuran (5 mL) was added triphenylphosphine (334 mg). The mixture was stirred at ambient temperature for overnight. The mixture was evaporated in vacuo, and the residue was purified by a silica gel column chromatography eluting with a mixture of n-hexane and ethyl acetate (3:1) to give 3-(cis-4-acetoxycyclohexyl)-1-(3-chloro-4-methoxybenzyl)-6-cyano-2,3-dihydro-1H-imidazo[4,5-b]pyridin-2-one (150 mg) as a pale yellow gum.

NMR(CDCl$_3$, δ): 1.62–1.78(4H, m), 2.06–2.19(5H, m), 2.68–2.84(2H, m), 3.89(3H, s), 4.50(1H, m), 4.95(2H, s), 5.08(1H, br s), 6.40(1H, br s), 6.90(1H, d, J=7 Hz), 7.14(1H, d, J=1 Hz), 7.19(1H, dd, J=8, 1 Hz), 7.31(1H, d, J=1 Hz), 8.31(1H, s).

EXAMPLE 24

To a suspension of 3-(cis-4-acetoxycyclohexyl)-1-(3-chloro-4-methoxybenzyl)-6-cyano-2,3-dihydro-1H-imidazo[4,5-b]pyridin-2-one (150 mg) in methanol (3 ml) was added potassium carbonate (180 mg). The mixture was stirred at ambient temperature for 2 hours, then potassium carbonate (180 mg) was added thereto. After stirring for 2 hours, the mixture was added with potassium carbonate (180 mg). After stirring overnight, the mixture was added with water and extracted with chloroform. The extracts were dried over magnesium sulfate and evaporated in vacuo. The residue was purified by a preparative thin-layer chromatography on silica gel developing with a mixture of ethyl acetate and n-hexane (2:1) to give 1-(3-chloro-4-methoxybenzyl)-6-cyano-3-(cis-4-hydroxycyclohexyl)-2,3-dihydro-1H-imidazo[4,5-b]pyridin-2-one (50 mg) as an oil.

mp 197–198° C.

NMR(CDCl$_3$, δ): 1.61–1.78(4H, m), 1.94–2.06(2H, m), 2.75–2.94(2H, m), 3.90(3H, s), 4.15(1H, br s), 4.46(1H, m), 4.97(2H, s), 6.91(1H, d, J=8 Hz), 7.15(1H, d, J=1 Hz), 7.19(1H, dd, J=8, 1 Hz), 7.33(1H, d, J=1 Hz), 8.32 (1H, d, J=1 Hz).

EXAMPLE 25

To a solution of 5-cyano-3-(3-formyl-4-methoxybenzyl)-1-(trans-4-hydroxycyclohexyl)-1,3-dihydro-2H-benzimidazol-2-one (35.0 mg) in a mixture of ethanol (2 mL) and tetrahydrofuran (1 mL) was added sodium borohydride (3.27 mg) under ice cooling, and the mixture was stirred at 0° C. for 2 hours. The mixture was partitioned between ethyl acetate and water. The separated organic layer was washed with 1N-hydrochloric acid, water, saturated sodium bicarbonate solution and brine, successively, dried over magnesium sulfate, and evaporated in vacuo. The residue was purified by a preparative silica gel column chromatography eluting with a mixture of chloroform and methanol (10:1). The crude product was triturated with diisopropyl ether to give 5-cyano-1-(trans-4-hydroxycyclohexyl)-3-(3-hydroxymethyl-4-methoxybenzyl)-1,3-dihydro-2H-benzimidazol-2-one as a colorless powder (20.0 mg).

NMR(DMSO-$d_6$, δ): 1.28–1.48 (2H, br), 1.65–1.78 (2H, br), 1.88–2.03 (2H, br), 2.14–2.35 (2H, br), 3.53–3.66 (1H, br), 3.73 (3H, s), 4.18–4.35 (1H, br), 4.42 (2H, d, J=7 Hz), 4.68 (1H, d, J=4 Hz), 5.00 (2H, s), 5.01 (1H, br), 6.90 (1H, d, J=8 Hz), 7.24 (1H, d, J=8 Hz), 7.37 (1H, s), 7.49 (1H, d, J=8 Hz), 7.55 (1H, d, J=8 Hz), 7.65 (1H, s).

MS (m/z) 406.

EXAMPLE 26

To a solution of 1-(trans-4-hydroxycyclohexyl)-3-(4-methoxy-3-methoxycarbonylbenzyl)-5-cyano-2,3-dihydro- 1H-benzimidazole-2-one (120 mg) in methanol (10 mL) and tetrahydrofuran (2 mL) was added 1N-aqueous sodium hydroxide solution (3 mL) and the mixture was stirred at 600° C. for an hour. After the solution was acidified with 1N-hydrochloric acid, the organic solvent of the solution was removed by evaporation. The aqueous layer was diluted with water and extracted with a mixture of chloroform and methanol (4:1). The separated organic layer was washed with water and brine, dried over magnesium sulfate, and evaporated in vacuo. The residue was triturated with diisopropyl ether to give 3-(3-carboxy-4-methoxybenzyl)-1-(trans-4-hydroxycyclohexyl)-5-cyano-2,3-dihydro-1H-benzimidazole-2-one as a colorless powder (88.8 mg).

NMR(DMSO-$d_6$, δ): 1.28–1.47 (2H, br), 1.66–1.78 (2H, br), 1.88–2.03 (2H, br), 2.14–2.33 (2H, br), 3.52–3.66 (1H, br), 3.78 (3H, s), 4.18–4.33 (1H, br), 4.68 (1H, br), 5.02 (2H, s), 7.08 (1H, d, J=8 Hz), 7.46–7.58 (3H, m), 7.66 (1H, s), 7.77 (1H, s).

MS (m/z) 420.

EXAMPLE 27

A solution of 3-(3-carboxy-4-methoxybenzyl)-1-(trans-4-hydroxycyclohexyl)-5-cyano-2,3-dihydro-1H-benzimidazole-2-one (51.0 mg), 1-ethyl-3-(3'-dimethylaminopropyl) carbodiimide hydrochloride (34.8 mg), 1-hydroxybenotriazole (24.5 mg) in anhydrous dimethylformamide (2 mL) was stirred at ambient temperature for 2 hours. After adding 28% ammonium solution (7 drops), the mixture was stirred at ambient temperature for 2 hours. The mixture was partitioned between ethyl acetate and water. The separated organic layer was washed with 1N-hydrochloric acid, water, saturated sodium bicarbonate solution and brine, successively, dried over magnesium sulfate, and evaporated in vacuo. The residue was triturated with diisopropyl ether to give 3-(3-carbamoyl-4-methoxybenzyl)-1-(trans-4-hydroxycyclohexyl)-5-cyano-2,3-dihydro-1H-benzimidazole-2-one as a colorless powder (28.6 mg).

NMR(CDCl$_3$, δ): 1.29–1.47 (2H, br), 1.65–1.78 (2H, br), 1.88–2.03 (2H, br), 2.13–2.32 (2H, br), 3.50–3.66 (1H, br), 3.85 (3H, s), 4.17–4.35 (1H, br), 4.68 (1H, d, J=7 Hz), 5.03 (2H, s), 7.09 (1H, d, J=8 Hz), 7.44–7.58 (4H, br), 7.62 (1H, br), 7.73 (1H, s), 7.79 (1H, s).

EXAMPLE 28

To a suspension of 3-(3-chloro-4-methoxybenzyl)-1-(piperidin-4-yl)-5-cyano-2,3-dihydro-1H-benzimidazole-2-one (91 mg) in methanol (5 mL) were added 37% formaldehyde aqueous solution (220 mg), sodium cyanotrihydroborate (43.2 mg) and acetic acid (5 drops) under nitrogen at ambient temperature. After stirring for 2 hours at same temperature, the reaction mixture was poured into saturated sodium bicarbonate solution and extracted with chloroform. The organic layer was washed with brine, dried over magnesium sulfate and evaporated in vacuo. The residue was triturated with diethyl ether to give 3-(3-chloro-4-methoxybenzyl)-5-cyano-1-(1-methylpiperidin-4-yl)-2,3-dihydro-1H-benzimidazole-2-one (75 mg) as an amorphous powder.

NMR(CDCl$_3$, δ): 1.78–1.90 (2H, m), 2.10–2.24 (2H, m), 2.32–2.52 (5H, m), 2.98–3.09 (2H, m), 3.89 (3H, s), 4.37–4.51(1H, m), 4.99 (2H, s), 6.90 (1H, d, J=8 Hz), 7.10 (1H, d, J=2 Hz), 7.20 (1H, dd, J=8,2 Hz),7.30–7.39 (3H, m).

EXAMPLE 29

A solution of methyl chloroformate (25.7 mg) in chloroform (1 ml) was added dropwise to a mixture of 3-(3-chloro-4-methoxybenzyl)-5-cyano-1-[(S)-pyrrolidin-3-yl]-2,3-dihydro-1H-benzimidazole-2-one (80 mg) and triethylamine (31.7 mg) in a mixture of chloroform (1.6 ml) and 1,3-dimethyl-2-imidazolidinone (0.8 ml) under cooling on an ice bath. The reaction mixture was stirred at same temperature for 2 hours and quenched by addition of 3-(N,N-diethylamino)propylamine (0.1 ml). The mixture was poured into water and extracted with chloroform. The organic layer was washed with 1N-hydrochloric acid, water, an aqueous saturated sodium bicarbonate solution and brine, dried over magnesium sulfate, and concentrated in vacuo. The residue was purified by a preparative thin layer chromatography (10% methanol in chloroform) to give 3-(3-chloro-4-methoxybenzyl)-5-cyano-1-[(S)-1-methoxycarbonylpyrrolidin-3-yl]-2,3-dihydro-1H-benzimidazole-2-one (55 mg).

NMR(CDCl$_3$, δ): 2.26–2.40 (1H, m), 2.49–2.65 (1H, m), 3.45–3.60 (1H, m), 3.75 (3H, s), 3.79–3.92 (6H, m), 4.97 (2H, s), 5.09–5.24 (1H, m), 6.90 (1H, d, J=8 Hz), 7.05–7.14 (2H, m), 7.21 (1H, dd, J=8, 2 Hz), 7.32 (1H, d, J=2 Hz), 7.40 (1H, d, J=8 Hz).

EXAMPLE 30

To a mixture of 3-(3-chloro-4-methoxybenzyl)-1-(3-hyoxypropyl)-5-cyano-2,3-dihydro-1H-benzimidazole-2-one (320 mg) and triethylamine (435 mg) in a mixture of dimethyl sulfoxide (3 mL) and dichloromethane (3 mL) was added portionwise sulfur trioxide pyridine complex (342 mg) at ambient temperature. After stirring at the same temperature for 3 hours, the reaction mixture was poured into water and extracted with chloroform. The organic layer was washed with water and brine, dried over magnesium sulfate and evaporated in vacuo. The residue was purified by a silica gel chromatography eluting with chloroform to give 3-(3-chloro-4-methoxybenzyl)-5-cyano-1-(2-formylethyl)-2,3-dihydro-1H-benzimidazole-2-one (258 mg) as a powder.

NMR(CDCl$_3$, δ): 3.06 (2H, t, J=8 Hz), 3.89 (3H, s), 4.24 (2H, t, J=8 Hz), 4.97 (2H, s), 6.90 (1H, d, J=8 Hz), 7.10 (1H, d, J=8 Hz), 7.15–7.24 (2H, m), 7.31 (1H, d, J=2 Hz), 7.44 (1H, d, J=8 Hz), 9.85 (1H, s).

EXAMPLE 31

To a suspension of 3-(3-chloro-4-methoxybenzyl)-5-cyano-1-(2-formylethyl)-2,3-dihydro-1H-benzimidazole-2-one (220 mg, 0.56 mmol) in a mixture of water (1 mL) and tert-butyl alcohol (4 mL) were added 2-methyl-2-butene (185 mg, 2.64 mmol) and sodium dihydrogenphosphate (78.5 mg, 0.654 mmol) at ambient temperature. To the mixture was added portionwise sodium chlorite (238 mg, 2.63 mmol), and the resulting mixture was stirred for 2 hours at ambient temperature. The reaction mixture was cooled in an ice bath, adjusted to pH 3 with 1N-hydrochloric acid. The resulting precipitate was collected by vacuum filtration and washed with ethyl acetate to give 3-[3-(3-chloro-4-methoxybenzyl)-5-cyano-2-one-2,3-dihydro-1H-benzimidazole-1-yl]propionic acid (167 mg) as a solid.

NMR(DMSO-$d_6$, δ): 2.68 (2H, t, J=7 Hz), 3.81(3H, s), 4.12 (2H, t, J=7 Hz), 5.01 (2H, s), 7.10 (1H, d, J=8 Hz), 7.31(1H, dd, J=8,2 Hz), 7.41–7.50 (2H, m), 7.54 (1H, dd, J=8,2 Hz), 7.74 (1H, d, J=2 Hz).

EXAMPLE 32

A mixture of 3-[3-(3-chloro-4-methoxybenzyl)-5-cyano-2-one-2,3-dihydro-1H-benzimidazole-1-yl]propionic acid (45 mg), N-methylamine hydrochloride (9.5 mg), 1-hydroxybenzotriazole (22 mg), and 1-(3-dimethylaminopropyl)-3-ethylcarbodiimide (24 mg) in anhydrous N,N-dimethylformamide (3 mL) was stirred at ambient temperature for 18 hours. The mixture was partitioned between water and ethyl acetate. The separated organic layer was washed with 1N-hydrochloric acid, water, saturated sodium bicarbonate solution and brine, successively, and dried over magnesium sulfate. After evaporation of the solvent, the residue was triturated with diethyl ether to give 3-[3-(3-chloro-4-methoxybenzyl)-5-cyano-2-one-2,3-dihydro-1H-benzimidazole-1-yl]-N-methylpropionamide (33 mg) as a pale yellow powder.

NMR(CDCl$_3$, δ): 2.70 (2H, t, J=6 Hz), 2.74 (3H, d, J=5 Hz), 3.89 (3H, s), 4.26 (2H, t, J=6 Hz), 4.97 (2H, s), 5.74 (1H, br peak), 6.90 (1H, d, J=8 Hz), 7.08 (1H, d, J=2 Hz), 7.19 (1H, dd, J=8, 2 Hz), 7.26–7.32 (2H, m), 7.43 (1H, dd, J=8, 2 Hz).

EXAMPLE 33

Sodium hydride (60% dispersion in mineral oil, 3.58g) was added portionwise to a solution 6-cyano-3-(trans-4-hydroxycyclohexyl)-2,3-dihydro-1H-imidazo[4,5-b]pyridin-2-one (21 g) in N,N-dimethylformamide (210 ml) at 0° C., and the mixture was stirred at ambient temperature for an hour. After adding 3-chloro-4-methoxybenzyl bromide (20.1 g) at ambient temperature, the reaction mixture was stirred at same temperature for 3 hours and partitioned between ethyl acetate and water. The aqueous layer was extracted with ethyl acetate (twice). The combined organic layer was washed with water (twice) and brine, and dried over magnesium sulfate. After evaporation of the solvent, the residue was purified by a silica gel column chromatography eluting with 5% methanol in chloroform and crystallization from ethanol. The crude crystals were suspended in water (400 ml) and stirred at 65° C. for 14 hours to give 1-(3-chloro-4-methoxybenzyl)-6-cyano-3-(trans-4-hydroxycyclohexyl)-2,3-dihydro-1H-imidazo[4,5-b]pyridin-2-one (19.9 g) as a colorless solid.

NMR(DMSO-d$_6$, δ): 1.25–1.40 (2H, m), 1.68–1.77 (2h, m), 1.90–2.00 (2H, m), 2.26–2.44 (2H, m), 3.42–3.55 (1H, m), 3.82 (3H, s), 4.22–4.35 (1H, m), 4.68 (1H, d, J=5.5 Hz), 4.98 (2H, s), 7.12 (1H, d, J=8.5 Hz), 7.35 (1H, dd, J=8.5, 2.0 Hz), 7.52 (1H, d, J=2.0 Hz), 8.10 (1H,d,J=2.0Hz), 8.48(1H, d, J=2.0 Hz).

What is claimed is:

1. A compound of the formula (Ia):

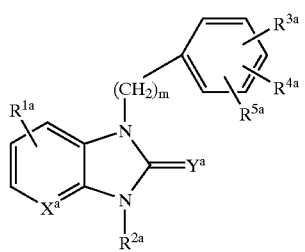

(Ia)

wherein
X$^a$ is nitrogen atom;
Y$^a$ is oxygen atom;
R$^{1a}$ is cyano group; nitro group; carbamoyl group; a lower alkylcarbamoyl group which may be substituted with a heterocyclic group; carboxy group; a lower alkoxycarbonyl group; a lower alkyl group; a halo(lower)alkyl group; a lower alkanoyl group; an aroyl group; or a lower alkanesulfonyl group, R$^{2a}$ is a cycloalkyl group which has one to three substituents selected from the group consisting of hydroxy, acyloxy, acyl, lower-alkoxy-substituted aralkyloxy, amino, acylamino, lower alkoxycarbonylamino, lower alkanesulfonylamino, ureido, lower alkylureido, sulfamoylamino, lower alkoxycarbonyl, lower alkanesulfonyl, lower alkyl, hydroxy(lower)alkyl, acyloxy(lower)alkyl, lower alkylenedioxy, carbamoyl, and sulfamoyl;

R$^{3a}$, R$^{4a}$ and R$^{5a}$ are, the same or different, hydrogen atom, a halogen atom, a lower alkanoyl group, carboxy group, a protected carboxy group, carbamoyl group, nitro group, cyano group, a lower alkyl group optionally substituted by hydroxy, a lower alkoxy group or a lower-alkoxy-substituted aralkyl group; or two of R$^{3a}$, R$^{4a}$ and R$^{5a}$ may combine together to form a lower alkylenedioxy group, and m is an integer of 1 or 2, its prodrug or a pharmaceutically acceptable salt thereof.

2. A compound of claim 1, wherein
R$^{2a}$ is a cyclohexyl group which has one to three substituents selected from the group consisting of hydroxy, lower alkanoyloxy, acyl, lower-alkoxy-substituted aralkyloxy, amino, lower alkenylamino, lower alkoxycarbonylamino, lower alkanesulfonylamino, ureido, lower alkylureido, sulfamoylamino, lower alkoxycarbonyl, lower alkanesulfonyl, lower alkyl, hydroxy(lower)alkyl, lower alkanoyloxy(lower)alkyl, lower alkylenedioxy, carbamoyl and sulfamoyl;

its prodrug or a pharmaceutically acceptable salt thereof.

3. A compound of claim 2, wherein
R$^{1a}$ is cyano group,
R$^{2a}$ is a cyclohexyl group which has hydroxy or lower alkanoyloxy,
R$^{3a}$ is a hydrogen atom,
R$^{4a}$ is a halogen atom,
R$^{5a}$ is a lower alkoxy group,
its prodrug or a pharmaceutically acceptable salt thereof.

4. A compound of claim 3 which is selected from the group consisting of 1-(3-chloro-4-methoxybenzyl)-6-cyano-3-(trans-4-hydroxycyclohexyl)-2,3-dihydro-1H-imidazo[4,5-b]pyridin-2-one, 1-(3-bromo-4-methoxybenzyl)-6-cyano-3-(trans-4-hydroxycyclohexyl)-2,3-dihydro-1H-imidazo[4,5-b]pyridin-2-one and
1-(3-chloro-4-methoxybenzyl)-6-cyano-3-(cis-4-hydroxycyclohexyl)-2,3-dihydro-1H-imidazo[4,5-b]pyridin-2-one.

5. A process for preparing a compound of the formula (Ia):

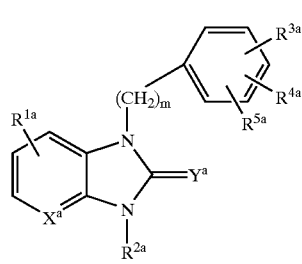

(Ia)

wherein
X$^a$ is nitrogen atom;
Y$^a$ is oxygen atom;

$R^{1a}$ is cyano group; nitro group; carbamoyl group; a lower alkylcarbamoyl group which may be substituted with a heterocyclic group; carboxy group; a lower alkoxycarbonyl group; a lower alkyl group; a halo(lower)alkyl group; a lower alkanoyl group; an aroyl group; or a lower alkanesulfonyl group, $R^{2a}$ is a cycloalkyl group which has one to three substituents selected from the group consisting of hydroxy, acyloxy, acyl, lower-alkoxy-substituted aralkyloxy, amino, acylamino, lower alkoxycarbonylamino, lower alkanesulfonylamino, ureido, lower alkylureido, sulfamoylamino, lower alkoxycarbonyl, lower alkanesulfonyl, lower alkyl, hydroxy(lower)alkyl, acyloxy(lower)alkyl, lower alkylenedioxy, carbamoyl, and sulfamoyl;

$R^{3a}$, $R^{4a}$ and $R^{5a}$ are, the same or different, hydrogen atom, a halogen atom, a lower alkanoyl group, carboxy group, a protected carboxy group, carbamoyl group, nitro group, cyano group, a lower alkyl group optionally substituted by hydroxy, a lower alkoxy group or a lower-alkoxy-substituted aralkyl group; or two of $R^{3a}$, $R^{4a}$ and $R^{5a}$ may combine together to form a lower alkylenedioxy group, and m is an integer of 1 or 2, its prodrug or a pharmaceutically acceptable salt thereof, which comprises reacting a compound of the formula (IIa):

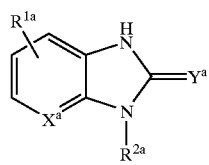

(IIa)

wherein $R^{1a}$, $R^{2a}$, $X^a$ and $Y^a$ are as defined above, or its salt with a compound of the formula (IIIa):

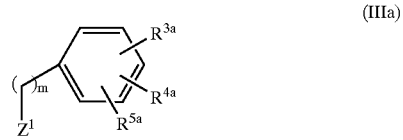

(IIIa)

wherein $R^{3a}$, $R^{4a}$, $R^{5a}$ and m are as defined above, and $Z^1$ is a halogen atom, in the presence of a base.

6. A method for treatment and/or prevention of angina, hypertension, pulmonary hypertension, congestive heart failure, glomerular diseases, renal tubulo-intestinal diseases, renal failure, atherosclerosis, conditions of reduced blood vessel patency, peripheral vascular disease, stroke, bronchitis, asthma, allergic rhinitis, urticaria, glaucoma, diseases characterized by disorders of gut motility, erectile dysfunction, female sexual dysfunction, impotence, diabetic complications, micturition disorder, or incontinence or storage of urine disorder, by administering a compound of claim 1.

7. A pharmaceutical composition containing a compound of claim 1, its prodrug or its salt in admixture with a pharmaceutical acceptable carrier or diluent.

* * * * *